(12) United States Patent
Chiku et al.

(10) Patent No.: US 12,235,263 B2
(45) Date of Patent: Feb. 25, 2025

(54) PROGESTERONE MEASURING KIT, PROGESTERONE MEASURING METHOD, AND PROGESTERONE MEASURING REAGENT

(71) Applicant: FUJIFILM Corporation, Tokyo (JP)

(72) Inventors: Hiroyuki Chiku, Ashigarakami-gun (JP); Takeru Shigemura, Ashigarakami-gun (JP); Kousuke Watanabe, Ashigarakami-gun (JP); Yoshinori Kanazawa, Ashigarakami-gun (JP); Kouitsu Sasaki, Ashigarakami-gun (JP); Kazuhei Kaneko, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1093 days.

(21) Appl. No.: 16/999,138

(22) Filed: Aug. 21, 2020

(65) Prior Publication Data
US 2020/0378962 A1   Dec. 3, 2020

Related U.S. Application Data

(63) Continuation of application No. PCT/JP2019/006705, filed on Feb. 22, 2019.

(30) Foreign Application Priority Data

Feb. 22, 2018   (JP) ................................. 2018-029328

(51) Int. Cl.
*G01N 33/543*   (2006.01)
*G01N 21/64*    (2006.01)
*G01N 33/547*   (2006.01)

(52) U.S. Cl.
CPC ... *G01N 33/54353* (2013.01); *G01N 21/6428* (2013.01); *G01N 33/54313* (2013.01); *G01N 33/547* (2013.01); *G01N 2021/6439* (2013.01)

(58) Field of Classification Search
CPC ... G01N 2021/6439; G01N 2021/7763; G01N 21/6428; G01N 21/648; G01N 2333/723; G01N 33/54313; G01N 33/54353; G01N 33/547; G01N 33/553
See application file for complete search history.

(56) References Cited

U.S. PATENT DOCUMENTS

| | | |
|---|---|---|
| 4,680,274 A | 7/1987 | Sakai et al. |
| 5,326,692 A | 7/1994 | Brinkley et al. |
| 5,433,896 A | 7/1995 | Kang et al. |
| 5,573,909 A | 11/1996 | Singer et al. |
| 5,670,381 A | 9/1997 | Jou et al. |
| 5,723,218 A | 3/1998 | Haugland et al. |
| 5,948,593 A | 9/1999 | Misawa et al. |
| 6,005,113 A | 12/1999 | Wu et al. |
| 10,816,469 B2 | 10/2020 | Kasagi et al. |
| 11,091,692 B2 | 8/2021 | Kanazawa et al. |

(Continued)

FOREIGN PATENT DOCUMENTS

| | | |
|---|---|---|
| CN | 1902490 A | 1/2007 |
| CN | 1944540 A | 4/2007 |

(Continued)

OTHER PUBLICATIONS

Yamada et al., "Size Determination of Latex Particles by Electron Microscopy," Aerosol Sci. Technol., 1985, vol. 4, No. 2, pp. 227-232.*

(Continued)

*Primary Examiner* — Galina M. Yakovleva
(74) *Attorney, Agent, or Firm* — Birch, Stewart, Kolasch & Birch, LLP

(57) ABSTRACT

An object of the present invention is to provide a kit, a method, and a reagent which prevent the problem of false positive due to nonspecific adsorption, suppress the increase in noise to be generated, and are capable of achieving high-precision measurement of progesterone in a wide concentration range from a low concentration to a high concentration, in the measurement of progesterone in a biological sample. The present invention provides a progesterone measuring kit including a first particle having a label and modified with a first binding substance, a second particle having no label and modified with a second binding substance, a flow channel, and a substrate, in which the first particle contains a compound represented by Formula (1) and a particle, and an average particle diameter of the first particles is 50 to 250 nm, an average particle diameter of the second particles is 70 to 500 nm, and the average particle diameter of the second particles is larger than the average particle diameter of the first particles.

(1)

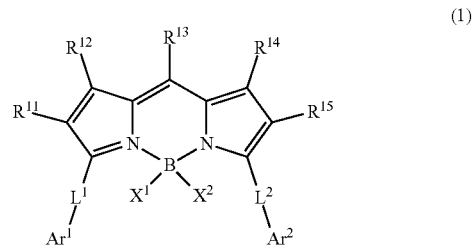

Each symbol in the formula has the meaning described in the present specification.

12 Claims, 2 Drawing Sheets

(56) References Cited

U.S. PATENT DOCUMENTS

| | | | |
|---|---|---|---|
| 11,136,500 B2 | 10/2021 | Watanabe et al. | |
| 11,519,860 B2* | 12/2022 | Chiku | G01N 33/54313 |
| 11,674,954 B2* | 6/2023 | Chiku | G01N 33/54313 |
| | | | 436/501 |
| 11,733,244 B2* | 8/2023 | Chiku | G01N 33/582 |
| | | | 435/7.1 |
| 11,821,896 B2* | 11/2023 | Chiku | G01N 33/54313 |
| 2006/0172357 A1 | 8/2006 | Yang et al. | |
| 2007/0154890 A1 | 7/2007 | Isobe | |
| 2009/0261269 A1 | 10/2009 | Horii et al. | |
| 2011/0054187 A1 | 3/2011 | Rurack et al. | |
| 2013/0078738 A1 | 3/2013 | Watanabe et al. | |
| 2014/0295468 A1 | 10/2014 | Kasagi et al. | |
| 2015/0051101 A1 | 2/2015 | Hoshino et al. | |
| 2015/0171328 A1 | 6/2015 | Bura et al. | |
| 2016/0069909 A1 | 3/2016 | Nakamura et al. | |
| 2016/0370289 A1 | 12/2016 | Hikage et al. | |
| 2018/0372638 A1 | 12/2018 | Kasagi et al. | |
| 2019/0185745 A1 | 6/2019 | Watanabe et al. | |
| 2020/0018765 A1 | 1/2020 | Chiku et al. | |
| 2020/0025748 A1 | 1/2020 | Chiku et al. | |
| 2020/0025770 A1 | 1/2020 | Chiku et al. | |
| 2020/0025771 A1* | 1/2020 | Chiku | C07D 209/56 |
| 2020/0033334 A1 | 1/2020 | Chiku et al. | |
| 2020/0096445 A1 | 3/2020 | Chiku et al. | |
| 2020/0378962 A1 | 12/2020 | Chiku et al. | |
| 2021/0364524 A1 | 11/2021 | Kanazawa et al. | |
| 2021/0380881 A1 | 12/2021 | Watanabe et al. | |

FOREIGN PATENT DOCUMENTS

| | | |
|---|---|---|
| CN | 102174144 A | 9/2011 |
| CN | 103033492 A | 4/2013 |
| CN | 105143234 A | 12/2015 |
| CN | 105462576 A | 4/2016 |
| CN | 106008581 A | 10/2016 |
| EP | 2 966 080 A1 | 1/2016 |
| EP | 2 995 952 A1 | 3/2016 |
| JP | 60-256057 A | 12/1985 |
| JP | 4-72564 A | 3/1992 |
| JP | 7-508309 A | 9/1995 |
| JP | 8-503547 A | 4/1996 |
| JP | 10-153599 A | 6/1998 |
| JP | 10-226172 A | 8/1998 |
| JP | 10-508897 A | 9/1998 |
| JP | 11-337551 A | 12/1999 |
| JP | 2000-206115 A | 7/2000 |
| JP | 2000-221196 A | 8/2000 |
| JP | 2001-21563 A | 1/2001 |
| JP | 3442777 B2 | 9/2003 |
| JP | 2007-127438 A | 5/2007 |
| JP | 2008-527332 A | 7/2008 |
| JP | 2008-190946 A | 8/2008 |
| JP | 2008-249361 A | 10/2008 |
| JP | 2010-19553 A | 1/2010 |
| JP | 2010-112748 A | 5/2010 |
| JP | 2010-190880 A | 9/2010 |
| JP | 2012-47684 A | 3/2012 |
| JP | 2012-199541 A | 10/2012 |
| JP | 2014-196283 A | 10/2014 |
| JP | 2014-235081 A | 12/2014 |
| JP | 2015-72249 A | 4/2015 |
| JP | 2016-57145 A | 4/2018 |
| KR | 10-2014-0137676 A | 12/2014 |
| WO | WO 92/21769 A1 | 12/1992 |
| WO | WO 93/23492 A1 | 11/1993 |
| WO | WO 96/29367 A1 | 9/1996 |
| WO | WO 2013/146694 A1 | 10/2013 |
| WO | WO 2014/013205 A1 | 1/2014 |
| WO | WO 2015/129361 A1 | 9/2015 |
| WO | WO 2017/150516 A1 | 9/2017 |
| WO | WO 2018/021376 A1 | 2/2018 |
| WO | WO 2018/021377 A1 | 2/2018 |
| WO | WO 2018/038137 A1 | 3/2018 |
| WO | WO 2018/038138 A1 | 3/2018 |
| WO | WO 2018/181796 A1 | 10/2018 |
| WO | WO 2018/181798 A1 | 10/2018 |
| WO | WO 2018/181800 A1 | 10/2018 |

OTHER PUBLICATIONS

"Theorie der Farbigkeit," Brands Chemie, Feb. 18, 2008, XP093129041, pp. 1-7, URL: http://www.bhbrand.de/downloads/1farbigkeit.pdf.*
Chinese Office Action for Chinese Application No. 201780051809.9, dated Jun. 13, 2022, with English translation.
Chinese Office Action for Chinese Application No. 201880022543.X, dated Aug. 5, 2022, with English translation.
Japanese Office Action for Japanese Application No. 2020-571226, dated Aug. 2, 2022, with English translation.
Chinese Office Action for Chinese Application No. 201780051809.9, dated Mar. 3, 2022, with English translation.
Extended European Search Report for European Application No. 20752374.7, dated Apr. 11, 2022.
Galangau et al., "Electrochromic and electrofluorochromic properties of a new boron dipyrromethene-ferrocene conjugate," Electrochimica Acta, vol. 87, 2013 (Available online Sep. 24, 2012), pp. 809-815.
Extended European Search Report, dated Mar. 19, 2021, for corresponding European Application No. 19756950.2.
Hecht et al., "Fluorinaled Boron-Dipyrromethene (BODIPY) Dyes: Bright and Versatile Probes for Surface Analysis," ChemistryOpen, vol. 2, No. 1, 2013 (Published online Jan. 9, 2013), pp. 25-38, XP055486484.
U.S. Office Action (Final) for U.S. Appl. No. 16/585,758, dated Apr. 22, 2022.
Japanese Office Action, dated Apr. 13, 2021, for corresponding Japanese Application No. 2020-501053, with an English translation.
Chinese Office Action and Search Report for Chinese Application No. 201880022538.9, dated May 13, 2022, with an English translation.
Chinese Office Action and Search Report for Chinese Application No. 201880022541.0, dated May 11, 2022, with an English translation.
Chinese Office Action and Search Report for Chinese Application No. 201880022543.X, dated Apr. 25, 2022, with an English translation.
U.S. Office Action for U.S. Appl. No. 16/585,306, dated Jun. 6, 2022.
U.S. Office Action for U.S. Appl. No. 16/585,306, dated Mar. 6, 2023.
Bartelmess et al., "Synthesis and Characterization of Far-Red/NIR-Fluorescent BODIPY Dyes, Solid-State Fluorescence, and Application as Fluorescent Tags Attached to Carbon Nano-onions," Chemistry—A European Journal, vol. 21, 2015, pp. 9727-9732, 6 pages total.
Brzeczek et al., "Systematic elongation of thienyl linkers and their effect on optical and electrochemical properties in carbazole-BODIPY donor-acceptor systems," RSC Advances, vol. 6, 2016, pp. 36500-36509, 10 pages total.
Chen et al., "Water-soluble, membrane-permeable organic fluorescent nanoparticles with large tunability in emission wavelengths and Stokes shifts," Chemistry Communications, vol. 49, 2013, pp. 5877-5879, 3 pages total.
Chinese Office Action and Search Report for Chinese Application No. 201780051809.9, dated May 31, 2021, with a partial English translation.
English translation of the International Preliminary Report on Patentability and Written Opinion of the International Searching Authority for International Application No. PCT/JP2018/013408, dated Oct. 1, 2019.
English translation of the International Preliminary Report on Patentability and Written Opinion of the International Searching Authority for International Application No. PCT/JP2018/013410, dated Oct. 1, 2019.
European Communication pursuant to Article 94(3) EPC for European Application No. 17843616.8, dated Nov. 19, 2020.

(56) References Cited

OTHER PUBLICATIONS

European Communication pursuant to Article 94(3) EPC for European Application No. 18774345.5, dated Feb. 15, 2021.
European Communication pursuant to Article 94(3) EPC for European Application No. 18774346.3, dated Feb. 15, 2021.
European Communication pursuant to Article 94(3) EPC for European Application No. 18775758.8, dated Feb. 16, 2021.
Extended European Search Report for European Application No. 17843616.8, dated Jun. 14, 2019.
Extended European Search Report for European Application No. 18774345.5, dated Feb. 10, 2020.
Extended European Search Report for European Application No. 18774346.3, dated Feb. 10, 2020.
Extended European Search Report for European Application No. 18775758.8, dated Feb. 10, 2020.
Feng et al., "Regioselective and Stepwise Syntheses of Functionalized BODIPY Dyes through Palladium-Catalyzed Cross-Coupling Reactions and Direct C—H Arylations," The Journal of Organic Chemistry, vol. 81, 2016, pp. 6281-6291, 11 pages total.
Gómez-Durán et al.,"Near-IR BODIPY Dyes à la Carte—Programmed Orthogonal Functionalization of Rationally Designed Building Blocks," Chemistry—A European Journal, vol. 22, 2016, pp. 1048-1061, 14 pages total.
Hu et al., "Engineering Lysosome-Targeting BODIPY Nanoparticles for Photoacoustic Imaging and Photodynamic Therapy under Near-Infrared Light," ACS Applied Materials & Interfaces, vol. 8, 2016, pp. 12039-12047, 9 pages total.
International Preliminary Report on Patentability (Form PCT/IPEA/409) for International Application No. PCT/JP2020/004222, dated Feb. 22, 2021, with an English translation.
International Preliminary Report on Patentability and Written Opinion of the International Searching Authority (Forms PCT/IB/373 and PCT/ISA/237) for International Application No. PCT/JP2017/030054, dated Feb. 26, 2019, with an English translation.
International Preliminary Report on Patentability and Written Opinion of the International Searching Authority (Forms PCT/IB/373 and PCT/ISA/237) for International Application No. PCT/JP2018/013406, dated Oct. 1, 2019, with an English translation.
International Search Report (Form PCT/ISA/210) for International Application No. PCT/JP2017/030054, dated Oct. 10, 2017, with an English translation.
International Search Report (Form PCT/ISA/210) for International Application No. PCT/JP2018/013410. dated Jun. 26, 2018, with an English translation.
International Search Report (Form PCT/ISA/210) for International Application No. PCT/JP2020/004222, dated Apr. 21, 2020, with an English translation.
International Search Report and Written Opinion of the International Searching Authority (Forms PCT/ISA/210 and PCT/ISA/237) for International Application No. PCT/JP2019/006705, dated May 21, 2019, with an English translation.
Japanese Notice of Reasons for Refusal for Japanese Application No. 2018-524075, dated Feb. 4, 2020, with an English translation.
Japanese Notice of Reasons for Refusal for Japanese Application No. 2018-535725, dated Jan. 7, 2020, with an English translation.
Japanese Notice of Reasons for Refusal for Japanese Application No. 2019-510171, dated Jul. 21, 2020, with an English translation.
Japanese Notice of Reasons for Refusal for Japanese Application No. 2019-510173, dated Jul. 21, 2020, with an English translation.
Japanese Notice of Reasons for Refusal for Japanese Application No. 2019-510175, dated Jul. 21, 2020, with an English translation.
Jiao et al., "Long wavelength red fluorescent dyes from 3,5-diiodo-BODIPYs," Organic & Biomolecular Chemistry, vol. 8, 2010, pp. 2517-2519, 3 pages total.
Korean Notification of Reason for Refusal for Korean Application No. 10-2019-7005239, dated Jan. 12, 2021, with an English translation.
Korean Notification of Reason for Refusal for Korean Application No. 10-2019-7005239, dated Jul. 15, 2020, with an English translation.
Korean Notification of Reason for Refusal for Korean Application No. 10-2019-7028398, dated Jan. 29, 2021, with an English translation.
Korean Notification of Reason for Refusal for Korean Application No. 10-2019-7028409, dated Jan. 14, 2021, with an English translation.
Küçüköz et al., "Enhancement of two photon absorption properties and intersystem crossing by charge transfer in pentaaryl borondipyrromethene (BODIPY) derivatives," Physical Chemistry Chemical Physics, vol. 18, 2016, pp. 13546-13553, 8 pages total.
Posthuma-Trumpie et al., "Development of a competitive lateral flow immunoassay for progesterone: influence of coating conjugates and buffer components," Analytical and Bioanalytical Chemistry, vol. 392, 2008, pp. 1215-1223, 9 pages total.
Rong et al., "Multicolor Fluorescent Semiconducting Polymer Dots with Narrow Emissions and High Brightness," ACS Nano, vol. 7, No. 1, 2013, pp. 376-384, 9 pages total.
Shi et al., "Tumor-targeting, enzyme-activated nanoparticles for simultaneous cancer diagnosis and photodynamic therapy," Journal of Materials Chemistry B, vol. 4, 2016, pp. 113-120, 8 pages total.
Sobenina et al., "Synthesis and Optical Properties of Difluorobora-s-diazaindacene Dyes with Trifluoromethyl meso-Substituents," European Journal of Organic Chemistry, 2013, pp. 4107-4118, 12 pages total.
Suda et al., "Multi-thiophene-substituted NIR boron-dibenzopyrromethene dyes: synthesis and their spectral properties," Tetrahedron, vol. 71, 2015, pp. 4174-4182, 9 pages total.
U.S. Office Action for U.S. Appl. No. 16/282,327, dated Feb. 8, 2021.
U.S. Office Action for U.S. Appl. No. 16/585,306, dated Jan. 18, 2022.
U.S. Office Action for U.S. Appl. No. 16/585,758, dated Dec. 7, 2021.
Wang et al., "Dihydronaphthalene-Fused Boron-Dipyrromethene (BODIPY) Dyes: Insight into the Electronic and Conformational Tuning Modes of BODIPY Fluorophores," Chemistry—A European Journal, vol. 16, 2010, pp. 2887-2903, 17 pages total.
Zhao et al., "Stepwise Polychlorination of 8-Chloro-BODIPY and Regioselective Functionalization of 2,3,5,6,8-Pentachloro-BODIPY," The Journal of Organic Chemistry, vol. 80, 2015, pp. 8377-8383, 7 pages total.
Zhu et al., "Highly water-soluble neutral near-infrared emissive BODIPY polymeric dyes," Journal of Materials Chemistry, vol. 22, 2012, pp. 2781-2790, 10 pages total.
Chinese Office Action for Chinese Application No. 201880022538.9, dated Sep. 15, 2022, with English translation.
Chinese Office Action for Chinese Application No. 201880022541.0, dated Aug. 26, 2022, with English translation.
European Communication pursuant to Article 94(3) EPC for corresponding European Application No. 19756950.2, dated Oct. 24, 2022.
U.S. Office Action for U.S. Appl. No. 16/585,231, dated Oct. 19, 2022.
U.S. Office Action for U.S. Appl. No. 16/585,306, dated Oct. 19, 2022.
U.S. Office Action for U.S. Appl. No. 16/585,758, dated Sep. 23, 2022.
Chinese Office Action for corresponding Chinese Application No. 201980014801.4, dated Apr. 15, 2023, with an English translation.
Chinese Office Action and Search Report for corresponding Chinese Application No. 201980014801.4, dated Dec. 16, 2022, with English translation.
Chinese Office Action for Chinese Application No. 201880022538.9, dated Jan. 9, 2023, with English translation.
Chinese Office Action for Chinese Application No. 201880022541.0, dated Jan. 5, 2023, with English translation.
Chinese Office Action for Chinese Application No. 201880022543.X, dated Jan. 9, 2023, with English translation.
Japanese Office Action for Japanese Application No. 2020-571226, dated Jan. 24, 2023, with English translation.
Galangau et al., "Rational design of visible and NIR distryryl-BODIPY dyes from a novel fluorinated platform," Org. Biomol. Chem., vol. 8, 2010, pp. 4546-4553.

(56) References Cited

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2019/006705, dated Sep. 3, 2020, with English translation.
International Search Report (Form PCT/ISA/210) for International Application No. PCT/JP2019/006705, dated May 21, 2019, with English translation.
Nagai et al., "Aromatic Ring-Fused BODIPY-Based Conjugated Polymers Exhibiting Narrow Near-Infrared Emission Bands," Macromolecules, vol. 43, No. 1, 2010 (published online Dec. 4, 2009), pp. 193-200.
Wild, "Logit-Log and Four-Parameter Log-Logistic Methods," The Immunassay Handbook, Third Edition, 2005, pp. 238-240 (4 pages).
Xu et al., "meso-C6F5 substituted BODIPYs with distinctive spectroscopic properties and their application for bioimaging in living cells," Tetrahedron, vol. 70, 2014 (published online Jun. 17, 2014), pp. 5800-5805.
European Communication pursuant to Article 94(3) EPC for European Application No. 17843616.8, dated Jun. 12, 2023.
Chinese Office Action and Search Report for Chinese Application No. 201880022481.2, dated Jun. 1, 2022, with English translation.
Chinese Office Action and Search Report for Chinese Application No. 201880022530.2, dated Jul. 6, 2022, with English translation.
Chinese Office Action and Search Report for Chinese Application No. 201880022600.4, dated Jun. 13, 2022, with English translation.
European Communication pursuant to Article 94(3) EPC for corresponding European Application No. 17843616.8, dated Feb. 22, 2024.
European Office Action for European Application No. 18774205.1, dated Feb. 16, 2021.
European Office Action for European Application No. 18774876.9, dated Feb. 15, 2021.
European Office Action for European Application No. 18777743.8, dated Feb. 16, 2021.
Extended European Search Report for corresponding European Application No. 23204869.4, dated Mar. 7, 2024.
Extended European Search Report for European Application No. 18774205.1, dated Feb. 10, 2020.
Extended European Search Report for European Application No. 18774876.9, dated Feb. 10, 2020:.
Extended European Search Report for European Application No. 18777743.8, dated Feb. 12, 2020.
Grazon et al., "Ultrabright BODIPY-Tagged Polystyrene Nanoparticles: Study of Concentration Effect on Photophysical Properties," The Journal of Physical Chemistry, vol. 118, Jun. 4, 2014, pp. 13495-13952.
International Preliminary Report on Patentability and English translation of the Written Opinion of the International Searching Authority (Forms PCT/IB/373 and PCT/ISA/237) for International Application No. PCT/JP2018/013405, dated Oct. 1, 2019:.
International Preliminary Report on Patentability and English translation of the Written Opinion of the International Searching Authority (Forms PCT/IB/373 and PCT/ISA/237) for International Application No. PCT/JP2018/013407, dated Oct. 1, 2019.
International Preliminary Report on Patentability and English translation of the Written Opinion of the International Searching Authority (Forms PCT/IB/373 and PCT/ISA/237) for International Application No. PCT/JP2018/013409, dated Oct. 1, 2019.
International Search Report and Written Opinion of the International Searching Authority (Forms PCT/ISA/210 and PCT/ISA/237) for International Application No. PCT/JP2018/013405, dated Jun. 26, 2018, with English translation.
International Search Report and Written Opinion of the International Searching Authority (Forms PCT/ISA/210 and PCT/ISA/237) for International Application No. PCT/JP2018/013407, dated Jul. 3, 2018, with English translation.
International Search Report and Written Opinion of the International Searching Authority (Forms PCT/ISA/210 and PCT/ISA/237) for International Application No. PCT/JP2018/013409, dated Jul. 3, 2018, with English translation.
Japanese Office Action for Japanese Application No. 2019-510170, dated Jul. 21, 2020, with English translation.
Japanese Office Action for Japanese Application No. 2019-510172, dated Jul. 21, 2020, with English translation.
Japanese Office Action for Japanese Application No. 2019-510174, dated Jul. 21, 2020, with English translation.
Korean Office Action for Korean Application No. 10-2019-7028399, dated Jan. 2, 2021, with English translation.
Korean Office Action for Korean Application No. 10-2019-7028408, dated Jan. 14, 2021, with English translation,.
Machine translation of JP-2008-190946-A, published on Aug. 21, 2008.
U.S. Notice of Allowance for U.S. Appl. No. 16/583,870, dated Jun. 2, 2022.
U.S. Notice of Allowance for U.S. Appl. No. 16/585,406, dated Aug. 24, 2022.
U.S. Notice of Allowance for U. S. U.S. Appl. No. 16/585,406, dated Mar. 17, 2022.
U.S. Office Action for U.S. Appl. No. 16/583,870, dated Feb. 8, 2022.
U.S. Office Action for U.S. Appl. No. 16/583,870, dated Sep. 23, 2021.
U.S. Office Action for U.S. Appl. No. 16/584,079, dated Apr. 22, 2022.
U.S. Office Action for U.S. Appl. No. 16/584,079, dated Sep. 19, 2022.
U.S. Office Action for U.S. Appl. No. 16/585,406, dated Oct. 14, 2021.
U.S. Office Action for U.S. Appl. No. 17/393,578, dated May 22, 2024.
Wang et al., "Synthesis, structure and photophysical properties of near-infrared 3,5-diarylbenzoBODIPY fluorophores," RSC Advances, vol. 6, 2016, pp. 52180-52188.
Yamaguchi et al., "How the π Conjugation Length Affects the Fluorescence Emission Efficiency," J. Am. Chem. Soc., vol. 130, 2008, pp. 13867-13869.
U.S. Office Action for U.S. Appl. No. 17/393,578, dated Oct. 24, 2024.
European Communication pursuant to Article 94(3) EPC for European Application No. 20752374.7, dated Sep. 3, 2024.
U.S. Office Action for U.S. Appl. No. 17/393,578, dated Aug. 8, 2024.

* cited by examiner

PROGESTERONE MEASURING KIT, PROGESTERONE MEASURING METHOD, AND PROGESTERONE MEASURING REAGENT

CROSS-REFERENCE TO RELATED APPLICATIONS

This application is a Continuation of PCT International Application No. PCT/JP2019/006705 filed on Feb. 22, 2019, which claims priority under 35 U.S.C § 119(a) to Japanese Patent Application No. 2018-029328 filed on Feb. 22, 2018. Each of the above application(s) is hereby expressly incorporated by reference, in its entirety, into the present application.

BACKGROUND OF THE INVENTION

1. Field of the Invention

The present invention relates to a progesterone measuring kit, a progesterone measuring method, and a progesterone measuring reagent.

2. Description of the Related Art

A fluorescence detection method is widely used as a highly sensitive and easy measurement method for quantifying a protein, an enzyme, an inorganic compound, or the like. The fluorescence detection method is a method for confirming the presence of a measurement target substance by detecting the fluorescence emitted in a case where excitation light of a specific wavelength is applied to a sample considered to contain a measurement target substance which is excited by the light of a specific wavelength to emit fluorescence. In a case where the measurement target substance is not a phosphor, for example, the presence of the measurement target substance can be confirmed by bring a substance in which a substance specifically binding to the measurement target substance is labeled with a fluorescent dye into contact with a sample, and then detecting the fluorescence emitted in a case where excitation light is applied in the same manner as described above.

In the fluorescence detection method as described above, there is known a method for utilizing the effect of electric field enhancement by plasmon resonance to improve sensitivity for detecting a measurement target substance present in a small amount. In this method, in order to generate plasmon resonance, a sensor chip having a metal layer in a predetermined area on a transparent support is prepared, and excitation light is incident from a surface side of the support opposite to a surface on which metal layer is formed, with respect to an interface between the support and the metal layer, at a predetermined angle equal to or more than the total reflection angle. The surface plasmon is generated in the metal layer by the irradiation with the excitation light, and the signal/noise ratio (S/N ratio) is improved by fluorescence enhancement, which is induced by the electric field enhancement effect caused by generation of the surface plasmon, and thus high-sensitive measurement can be achieved. The fluorescence detection method by surface plasmon excitation (hereinafter, also referred to as "SPF method") is about 10 times stronger in a signal enhancement degree than the fluorescence detection method by epi-excitation (also referred to as epi-fluorescence method), and thus high-sensitive measurement can be achieved.

JP3442777B discloses fluorescent microparticles produced by blending an initial donor dye having a preferable excitation peak and a final receptor dye having a preferred luminescence peak in polymer microparticles. In JP3442777B, it is described that a polyazaindacene dye is used as the dye.

Olivier Galangau et al., Org. Biomol. Chem., 2010, Vol. 8, pp. 4546 to 4553 discloses that a novel distyryl BODIPY (registered trademark, abbreviation of boron-dipyrromethene) dye is designed and synthesized, and the synthesized distyryl BODIPY (registered trademark) dye has been analyzed for absorption and emission spectra in a chloromethane solution.

In addition, in the immunoassay method, not only a positive test sample which contains a test substance but also a test sample which becomes positive by reacting to even negative test sample which does not contain the test substance are present, and thus the problem of false positive has been recognized in the related art. The causes of the false positive are not clear, but one of the causes is considered to be the presence of some factors contained in a serum, which causes a nonspecific reaction.

As a technique for suppressing the nonspecific reaction, JP1985-256057A (JP-S60-256057A) describes that in an immunological measurement method, in particular, an immunological measurement method utilizing aggregation, in order to prevent a nonspecific immune reaction of a sensitized particle having a size of 0.3 to 2.0 µm, an ultrafine particle having a size of 0.2 µm or less, to which a substance capable of reacting to a substance causing the nonspecific immune reaction is bound, is used. JP2000-221196A describes that in a method for detecting a test substance by an immunoagglutination reaction utilizing a sensitized particle having a size of 0.4 µm or more, in which an insoluble carrier particle having a size of 0.01 µm to 0.5 µm is used as a particle used in blocking. In addition, JP1999-337551A (JP-H11-337551A) describes a method in which a substance obtained by immobilizing an antigen or an antibody that does not immunologically react with a substance to be measured to a particle smaller than a particle reacting specifically is added, for the purpose of suppressing the nonspecific reaction. Furthermore, JP2007-127438A describes a nonspecific reaction inhibitor which is used in an immunoassay method in which an immunoassay particle obtained by supporting an antigen or an antibody that immunologically reacts with a substance to be measured on a carrier having an average particle diameter of 0.05 to 0.5 µm is used, and also describes that the nonspecific reaction inhibitor includes an insoluble carrier supporting an antigen or an antibody that does not immunologically react with a substance to be measured in the presence of an organic solvent and an average particle diameter of the insoluble carriers are smaller than an average particle diameter of the carriers. JP2010-019553A describes that in an immunodetection method using a fluorescence spectroscopy technique, influence of a nonspecific reaction is suppressed by a particle having an outer diameter of 1 µm or less.

JP2010-112748A describes a detection method for detecting the amount of a substance to be detected using a sensor chip including a sensor unit having a laminated structure including a metal layer adjacent to the dielectric plate on one surface of the dielectric plate. Specifically, by bringing a sample into contact with the sensor unit, coupling an amount of a fluorescent label binding substance formed of a fluorescent label and a binding substance labeled with the fluorescent label, the amount corresponding to an amount of the substance to be detected contained in the sample, to the sensor unit, and irradiating the sensor unit with excitation light, an enhanced optical electric field is generated on the sensor unit, the enhanced optical electric field excites the fluorescence label, and the amount of the substance to be detected is measured based on the amount of light generated due to the excitation.

In JP2010-112748A, a fluorescent substance constituted of a plurality of first fluorescent dye molecules as the fluorescence label and a first particle formed of a light-transmitting material that transmits fluorescence generated from the plurality of first fluorescent dye molecules and containing the plurality of first fluorescent dye molecules is used. Further, as a blocking agent for preventing the fluorescent label binding substance from adsorbing to the sensor unit due to the non-specific adsorption property of the fluorescent label binding substance to the sensor unit, a blocking agent that does not include the first fluorescent dye molecule, does not nonspecifically bind to a binding substance, and has a nonspecific adsorption property equivalent to the nonspecific adsorption property of the fluorescent label binding substance is used.

JP2015-072249A discloses an immunoassay method in which nonspecific adsorption is suppressed using a dry particle having a defined particle size.

JP1996-503547A (JP-H8-503547) describes the importance of measuring progesterone which is corpus luteum hormone in an early pregnancy test. Progesterone measurements allow conclusions to be made regarding ovulation cycle, estrus, pregnancy or atrophy in various mammalian species.

SUMMARY OF THE INVENTION

As described above, although the SPF method is known as a method capable of high-sensitive measurement by a simple measurement method, the SPF method is not sufficiently satisfactory for the measurement of a very small amount of a measurement target substance. Among the detection methods, in a competition method for measuring small molecules, such as progesterone, that cannot be sandwiched by antibodies, it has been necessary to lower a concentration of fluorescence labels in the reaction system in order to raise the detection sensitivity in a region where a concentration of a measurement target substance is low.

In addition, as described in JP1985-256057A (JP-S60-256057A), JP2000-221196A, JP1999-337551A (JP-H11-337551A), JP2007-127438A, and JP2010-019553A, there are a specific sample in which false positive due to a nonspecific immune reaction-causing substance present in the sample is a problem, fine particles provided with a substance interacting with the nonspecific immune reaction-causing substance are used, and thus technique request can be avoided. However, the methods described in JP1985-256057A (JP-S60-256057A), JP2000-221196A, JP1999-337551A (JP-H11-337551A), and JP2007-127438A, there has been a problem that the measurement by the agglutination method has low sensitivity and cannot be used for detecting a very small amount of a measurement target substance. The immunoassay method disclosed in JP1985-256057A (JP-S60-256057A) has a disadvantage that a washing step or a centrifugation operation is required, and thus the method is not a simple measurement method.

JP2010-019553A describes that in an immunodetection method using a fluorescence spectroscopy technique, influence of a nonspecific reaction is suppressed by a particle having an outer diameter of 1 μm or less, but the method is not very simple measurement. In addition, in both JP2010-112748A and JP2015-072249A, simple immunoassay methods using a flow channel are disclosed, a specimen is measured by a measurement method using a fluorescence method, but a technique for raising detection sensitivity in a range where a concentration of a measurement target substance is low is not disclosed.

Furthermore, in a case of increasing the sensitivity so that a small amount of a detection substance can be detected, there is a problem of not only false positive due to nonspecific adsorption but also noise increase.

An object of the present invention is to provide a kit, a method, and a reagent which prevent the problem of false positive due to nonspecific adsorption, suppress the increase in noise to be generated, and are capable of achieving high-precision measurement of progesterone in a wide concentration range from a low concentration to a high concentration, in the measurement of progesterone in a biological sample.

The present inventors, in order to solve the above problem, have eagerly studied configurations for a kit for measuring progesterone, which includes a first particle having a label and modified with a first binding substance capable of specifically binding to progesterone, a second particle having no label and modified with a second binding substance capable of not specifically binding to the progesterone, a flow channel for flowing the first particle and the second particle, and a substrate having a substance capable of binding to the first binding substance. As a result, the present inventors have found that the above problem can be solved by satisfying the conditions in which the first particle having a label has an emission maximum wavelength in a long wavelength region of 680 nm or more, a labeled particle exhibiting a high quantum yield is used, the average particle diameter of the first particles is 50 to 250 nm, the average particle diameter of the second particles is 70 to 500 nm, and the average particle diameter of the second particles is larger than the average particle diameter of the first particles. The present invention has been completed based on these findings.

That is, according to the present invention, the following inventions are provided.

[1] A progesterone measuring kit, comprising:

a first particle having a label and modified with a first binding substance capable of specifically binding to progesterone;

a second particle having no label and modified with a second binding substance incapable of specifically binding to progesterone;

a flow channel for flowing the first particle and the second particle; and a substrate having a substance capable of binding to the first binding substance, wherein the first particle having a label contains at least one compound represented by Formula (1) and a particle, and an average particle diameter of the first particles is 50 to 250 nm, an average particle diameter of the second particles is 70 to 500 nm, and the average particle diameter of the second particles is larger than the average particle diameter of the first particles,

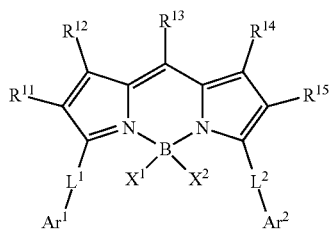

(1)

In the formula, $R^{11}$ to $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent, and at least three of $R^{11}$, . . . , or $R^{15}$ represent atoms or groups other than hydrogen atoms. $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $X^1$ and $X^2$ may be linked to each other to form a ring. $Ar^1$ and $Ar^2$ each independently represent an aryl group or a heterocyclic group, each of which may have a substituent. $L^1$ and $L^2$ each independently represent any one of Formulae (L-1) to (L-4).

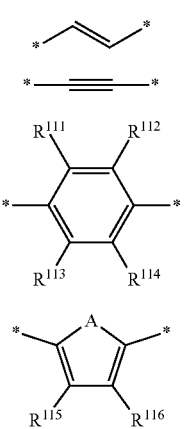

Formula (L-1)

Formula (L-2)

Formula (L-3)

Formula (L-4)

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. A represents —O—, —S—, or —NH—.

[2] The kit according to [1], in which the first particle and the second particle are latex particles.

[3] The kit according to [1] or [2], in which the first particle having a label is a luminescent particle containing at least one kind of energy donor compound, at least one kind of energy acceptor compound, and a particle, and at least one kind of the energy donor compound or the energy acceptor compound is the compound represented by Formula (1).

[4] The kit according to [3], in which at least one kind of compound represented by Formula (1) is contained as the energy donor compound, and at least one kind of compound represented by Formula (1) is contained as the energy acceptor compound.

[5] The kit according to [3] or [4], in which a molar ratio of the energy donor compound to the energy acceptor compound is 1:10 to 10:1.

[6] The kit according to any one of [1] to [5], in which a mass ratio of the second particle to the first particle is 1 to 20.

[7] The kit according to any one of [1] to [6], in which the first binding substance capable of specifically binding to progesterone is an antibody.

[8] A progesterone measuring method comprising:
a step (i) of mixing a first particle (a) having a label and modified with a first binding substance capable of specifically binding to progesterone, a second particle (b) having no label and modified with a second binding substance incapable of specifically binding to progesterone, and a test sample (c) containing progesterone to obtain a mixture;
a step (Ii) of applying the mixture obtained in the step (i) onto a substrate;
a step (Iii) of capturing the first binding substance at a reaction site on the substrate having a substance capable of binding to the first binding substance; and
a step (iv) of detecting the first particle having a label and modified with the first binding substance captured on the reaction site,
wherein the first particle having a label contains at least one compound represented by Formula (1) and a particle,
an average particle diameter of the first particles is 50 to 250 nm, an average particle diameter of the second particles is 70 to 500 nm, and the average particle diameter of the second particles is larger than the average particle diameter of the first particles.

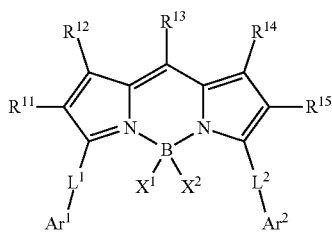

(1)

In the formula, $R^{11}$ to $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent, and at least three of $R^{11}$, . . . , or $R^{15}$ represent atoms or groups other than hydrogen atoms. $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $X^1$ and $X^2$ may be linked to each other to form a ring. $Ar^1$ and $Ar^2$ each independently represent an aryl group or a heterocyclic group, each of which may have a substituent. $L^1$ and $L^2$ each independently represent any one of Formulae (L-1) to (L-4).

Formula (L-1)

Formula (L-2)

Formula (L-3)

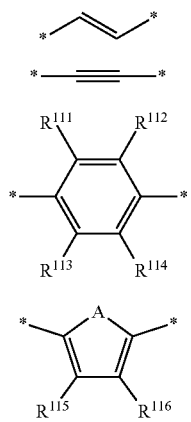

Formula (L-4)

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. A represents —O—, —S—, or —NH—.

[9] The method according to [8], in which the first particle and the second particle are latex particles.

[10] The method according to [8] or [9], in which the first particle having a label is a luminescent particle containing at least one kind of energy donor compound, at least one kind of energy acceptor compound, and a particle, and at least one kind of the energy donor compound or the energy acceptor compound is the compound represented by Formula (1).

[11] The method according to [10], in which at least one kind of compound represented by Formula (1) is contained as the energy donor compound, and at least one kind of compound represented by Formula (1) is contained as the energy acceptor compound.

[12] The method according to any one of [8] to [11], in which a mass ratio of the second particle to the first particle is 1 to 20.

[13] The method according to any one of [8] to [12], in which, in the step (iv), the first particle having a label and modified with the first binding substance captured on the reaction site is detected by a surface plasmon fluorescence method.

[14] A progesterone measuring reagent comprising:
a first particle (a) having a label and modified with a first binding substance capable of specifically binding to progesterone; and
a second particle (b) having no label and modified with a second binding substance incapable of specifically binding to progesterone,
wherein the first particle having a label contains at least one compound represented by Formula (1) and a particle, and
an average particle diameter of the first particles is 50 to 250 nm, an average particle diameter of the second particles is 70 to 500 nm, and the average particle diameter of the second particles is larger than the average particle diameter of the first particles.

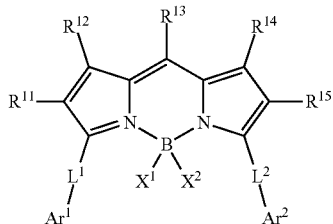

(1)

In the formula, $R^{11}$ to $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent, and at least three of $R^{11}$, . . . , or $R^1$ represent atoms or groups other than hydrogen atoms. $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $X^1$ and $X^2$ may be linked to each other to form a ring. $Ar^1$ and $Ar^2$ each independently represent an aryl group or a heterocyclic group, each of which may have a substituent. $L^1$ and $L^2$ each independently represent any one of Formulae (L-1) to (L-4).

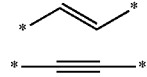

Formula (L-1)

Formula (L-2)

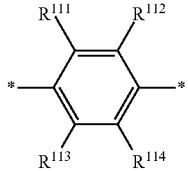

Formula (L-3)

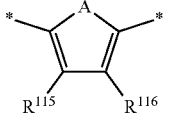

Formula (L-4)

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. A represents —O—, —S—, or —NH—.

[15] The progesterone measuring reagent according to [14], in which the compound represented by Formula (1) is a compound represented by Formula (3),

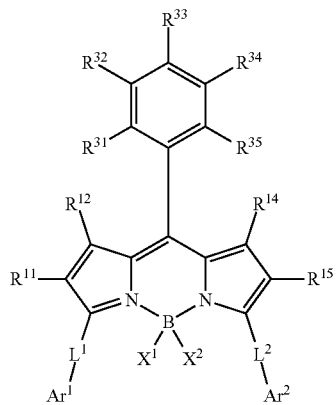

(3)

In the formula, $R^{11}$, $R^{12}$, $R^{14}$, $R^{15}$, $X^1$, $X^2$, $Ar^1$, $Ar^2$, $L^1$, and $L^2$ are as defined in Formula (1), provided that at least two of $R^{11}$, $R^{12}$, $R^{14}$, or $R^{15}$ are atoms or groups other than hydrogen atoms. $R^{31}$ to $R^{35}$ each independently represent a hydrogen atom, a halogen atom, an alkyl group, an aryl group, a heterocyclic group, an ethenyl group, an ethynyl group, an amino group, an acyl group, a cyano group, an alkoxy group, an aryloxy group, an alkylthio group, or an arylthio group, each of which may have a substituent, and any one of $R^{31}$, $R^{32}$, $R^{34}$, or $R^{35}$ is a group consisting of two or more atoms.

[16] The progesterone measuring reagent according to [14], in which the compound represented by Formula (1) is a compound represented by Formula (4).

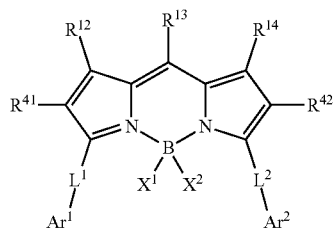

(4)

In the formula, $R^{12}$, $R^{13}$, $R^{14}$, $X^1$, $X^2$, $Ar^1$, $Ar^2$, $L^1$, and $L^2$ are as defined in Formula (1), provided that at least one of $R^{12}$, $R^{13}$, or $R^{14}$ is an atom or group other than a hydrogen atom. $R^{41}$ and $R^{42}$ each independently represent an aryl group, a heterocyclic group, an ethenyl group, or an ethynyl group, each of which may have a substituent.

[17] The progesterone measuring reagent according to [14], in which the compound represented by Formula (1) is a compound represented by Formula (5).

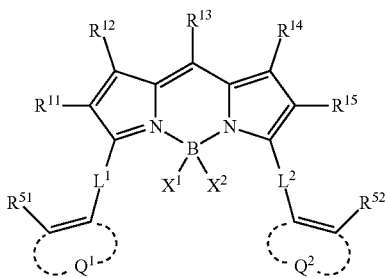

(5)

In the formula, $R^{11}$ to $R^{15}$, $X^1$, $X^2$, $L^1$, and $L^2$ are as defined in Formula (1). $R^{51}$ and $R^{52}$ each independently represent an alkyl group, an aryl group, a heteroaryl group, an amino group, an acyl group, an alkoxy group, an aryloxy group, an alkylthio group, or an arylthio group, each of which may have a substituent. $Q^1$ and $Q^2$ each independently represent an aromatic hydrocarbon ring or an aromatic heterocyclic ring, each of which may have a substituent.

[18] The progesterone measuring reagent according to any one of [14] to [17], in which a mass ratio of the second particle to the first particle is 1 to 20.

[19] The progesterone measuring reagent according to any one of [14] to [18], in which the first binding substance capable of specifically binding to the progesterone is an antibody.

[20] The progesterone measuring reagent according to any one of [14] to [19], in which the first particle having a label is a fluorescent latex particle and the second particle is a latex particle.

According to the progesterone measuring kit, progesterone measuring method, and progesterone measuring reagent of the embodiment of the present invention, the problem of false positive due to nonspecific adsorption is prevented, the increase in noise to be generated is suppressed, and thus high-precision measurement of progesterone can be achieved in a wide concentration range from a low concentration to a high concentration, in the measurement of progesterone in a biological sample.

DESCRIPTION OF THE PREFERRED EMBODIMENTS

Figure 1:
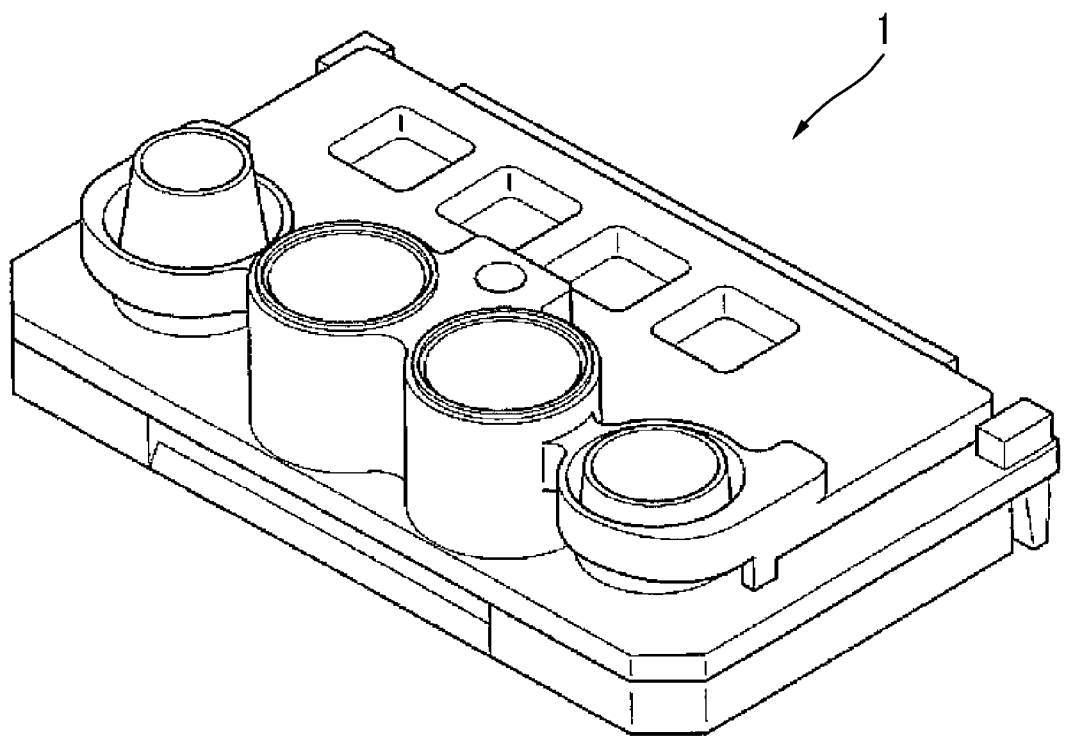
FIG. 1 shows a schematic view of a sensor chip.

Hereinafter, embodiments of the present invention will be described in detail.

In the present specification, the numerical range indicated by using "to" means a range including numerical values described before and after "to" as a minimum value and a maximum value, respectively.

[Progesterone Measuring Kit]

The progesterone measuring kit according to the embodiment of the present invention includes a first particle having a label and modified with a first binding substance capable of specifically binding to progesterone, a second particle having no label and modified with a second binding substance incapable of specifically binding to progesterone, a flow channel for flowing the first particle and the second particle, and a substrate having a substance capable of binding to the first binding substance, in which the first particle having a label contains at least one compound represented by Formula (1) that is defined in the present specification and a particle, and an average particle diameter of the first particles is 50 to 250 nm, an average particle diameter of the second particles is 70 to 500 nm, and the average particle diameter of the second particles is larger than the average particle diameter of the first particles.

(Biological Sample)

In the present invention, progesterone in a biological sample can be measured.

The biological sample is not particularly limited as long as the sample is a sample that may contain progesterone. For example, biologic samples, particularly body fluids (for example, blood, serums, plasma, spinal fluid, tears, sweat, urine, pus, runny nose, or sputum) or excrements (for example, feces), organs, tissues, mucous membranes, skin, or the like of animals (for example, humans, dogs, cats, horses, or the like) can be mentioned.

(Progesterone)

Progesterone is a sex hormone that is secreted from ovaries and placenta and is involved in luteal function and pregnancy. Progesterone is used to diagnose menstrual cycle abnormality and infertility. Progesterone is also used to check the mating timing of dogs and ovarian remnants of cats.

(Particle)

The material and form of the particles (a first particle and a second particle) in the present invention are not particularly limited, and for example, organic polymer particles such as polystyrene beads or inorganic particles such as glass beads can be used. Specific examples of the material of the particles include a homopolymer obtained by polymerizing a monomer such as styrene, methacrylic acid, glycidyl (meth)acrylate, butadiene, vinyl chloride, vinyl acetate acrylate, methyl methacrylate, ethyl methacrylate, phenyl methacrylate, or butyl methacrylate, and a copolymer obtained by polymerizing two or more monomers. Examples of the particles include other organic polymer powders, inorganic substance powders, microorganisms, blood cells, cell membrane fragments, liposomes, and microcapsules. Latex particles are preferable as the first particle and the second particle.

In a case where latex particles are used, specific examples of the material of the latex include polystyrene, a styrene-acrylic acid copolymer, a styrene-methacrylic acid copolymer, a styrene-glycidyl (meth)acrylate copolymer, a styrene-styrene sulfonate copolymer, a methacrylic acid polymer, an acrylic acid polymer, an acrylonitrile-butadiene-styrene copolymer, a vinyl chloride-acrylic acid ester copolymer, and polyvinyl acetate acrylate. As the latex, a copolymer containing at least styrene as a monomer is preferable, and a copolymer of styrene and acrylic acid or methacrylic acid is particularly preferable. The method for preparing the latex is not particularly limited, and the latex can be prepared by any polymerization method. However, in a case where the luminescent particle of the embodiment of the present invention is used by labeling with an antibody, the presence of a surfactant makes it difficult to immobilize the antibody.

(First Binding Substance)

The first binding substance used in the present invention is a substance capable of specifically binding to progesterone. As the first binding substance, an antibody can be used, but the first binding substance is not limited thereto. Preferably, the first binding substance is an antibody. In a case where the first binding substance is an antibody, an antiserum prepared from a serum of an animal immunized with progesterone, an immunoglobulin fraction purified from the antiserum, a monoclonal antibody obtained by cell fusion using spleen cells of an animal immunized with progesterone, or a fragment thereof [for example, F(ab')$_2$, Fab, Fab', or Fv] can be used. Preparation of these antibodies can be performed by a conventional method. Furthermore, the antibody may be modified as in the case of a chimeric antibody or the like, or a commercially available antibody or an antibody prepared from an animal serum or culture supernatant by known methods can be used.

In the present invention, an anti-progesterone antibody capable of specifically binding to progesterone (preferably, specifically recognizing progesterone) is preferably used as the first binding substance.

A method for preparing an anti-progesterone antibody is described below as an example.

A progesterone-BSA conjugate can be prepared by mixing progesterone, bovine serum albumin (hereinafter referred to as BSA), and a condensing agent. Using the conjugate as a mouse immunization antigen, mice are subcutaneously immunized at the back several times. In this case, the incomplete Freund's adjuvant (CFA) and/or the incomplete Freund's adjuvant (IFA) can be appropriately selected and then used as a mixture with the immunization antigen. The incomplete Freund's adjuvant is a substance that stimulates immunity and is a mixture of paraffin and ARLACEL. The complete Freund's adjuvant is an adjuvant in which dead mycobacteria or dead bacteria of *Mycobacterium tuberculosis* are added to the incomplete Freund's adjuvant to further enhance the antigenicity. After several immunizations are performed as appropriate for several weeks, a blood sample is collected from the mice and antibody titers are measured. The antigen is administered intraperitoneally in a case where a sufficient rise in the antibody titers is observed, and the spleen is isolated several days later. By fusing the spleen cells isolated from the immunized mice with mutant myeloma cells (myeloma), it is possible to prepare fused cells having an antibody-producing ability. Only cells producing antibody against a target antigen are selected from the fused cells, and limiting dilution is performed to proliferate only the cell line producing the antibody. Culture (cloning) of the cells after dilution can be performed. The fusion cell line obtained as described above is injected into the abdominal cavity of a mouse, monoclonal antibodies can be produced in ascites fluid by proliferating ascites-type antibody-producing cells, and thus a target antibody can be obtained by recovering these antibodies.

(First Particle Having Label)

A first particle having a label used in the present invention is a particle containing at least one kind of compound represented by Formula (1) and a particle, and is also described as a labeled particle or a fluorescence-labeled particle. The first particle having a label is preferably a latex particle and more preferably a fluorescent latex particle.

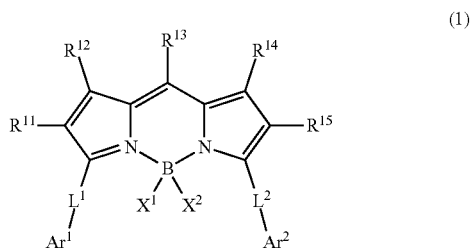

(1)

The meaning of each symbol in Formula (1) is as defined in the present specification.

It is known that an ordinary dye compound is influenced by association in a case where the amount of incorporation into particles is increased, and thus the quantum yield decreases (this is also referred to as concentration quenching). In particular, in a case of being incorporated into particles, a fluorescent dye compound having a long absorption wavelength of 650 nm or longer tends to exhibit concentration quenching, whereby it is difficult to maintain a quantum yield.

Inclusion of a conjugated substituent in the compound represented by Formula (1) used in the present invention makes it possible to emit light of long wavelength and inclusion of a plurality of substituents in the dipyrromethene skeleton makes it also possible to suppress a decrease in the quantum yield in the polymer particle. As a factor of suppressing a decrease in the quantum yield, suppression of intermolecular interaction (for example, 7-7 interaction) by a plurality of substituents projecting in a direction perpendicular to the dipyrromethene skeleton is considered. According to the compound represented by Formula (1), it is possible to produce a first particle (preferably a fluorescent particle, and more preferably a fluorescent nanoparticle) having a label having high luminance, particularly in the long wavelength range. In a case where the particle having a label is a fluorescent particle, the luminance is the fluorescence intensity. According to the present invention, since the luminescence quantum yield is high in the region of the window of a living body (in the vicinity of 650 to 900 nm which is a near-infrared wavelength range which is easy to transmit through the living body), the sensitivity of sensing using luminescence can be improved.

In the present specification, the alkyl group may be any of linear, branched, cyclic, or a combination thereof, and the number of carbon atoms in the linear or branched alkyl group is preferably 1 to 36, more preferably 1 to 18, still more preferably 1 to 12, and particularly preferably 1 to 6. The cyclic alkyl group may be, for example, a cycloalkyl group having 3 to 8 carbon atoms. Specific examples of the alkyl group include a methyl group, an ethyl group, an n-propyl group, an isopropyl group, an n-butyl group, an iso-butyl group, a sec-butyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, and a cyclohexyl group.

In the present specification, the aryl group is preferably an aryl group having 6 to 48 carbon atoms, more preferably an aryl group having 6 to 24 carbon atoms, and still more preferably an aryl group having 6 to 14 carbon atoms, and examples thereof include a phenyl group, a naphthyl group, an anthryl group, a pyrenyl group, a phenanthrenyl group, a biphenyl group, and a fluorenyl group.

In the present specification, the heterocyclic group is preferably any one of 5- to 7-membered substituted or unsubstituted, saturated or unsaturated, aromatic or non-aromatic, or monocyclic or fused heterocyclic groups. The heterocyclic group is preferably a heterocyclic group having a ring-constituting atom selected from a carbon atom, a nitrogen atom, an oxygen atom and a sulfur atom and having at least one hetero atom selected from a nitrogen atom, an oxygen atom, or a sulfur atom, and more preferably a 5- or 6-membered aromatic heterocyclic group having 3 to 30 carbon atoms. Examples of the heterocyclic group include a furyl group, a benzofuryl group, a dibenzofuryl group, a thienyl group, a benzothienyl group, a dibenzothienyl group, a pyridyl group, a pyrimidinyl group, a quinolyl group, an isoquinolyl group, an acridinyl group, a phenanthridinyl group, a pteridinyl group, a pyrazinyl group, a quinoxalinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a pyrrolyl group, an indolyl group, an imidazopyridinyl group, and a carbazolyl group.

In the present specification, the acyl group is preferably a linear or branched alkanoyl group having 2 to 15 carbon atoms, and examples thereof include an acetyl group, a propionyl group, a butyryl group, an isobutyryl group, a valeryl group, an isovaleryl group, a pivaloyl group, a hexanoyl group, a heptanoyl group, and a benzoyl group.

In the present specification, the alkoxy group is preferably an alkoxy group having 1 to 20 carbon atoms, and examples thereof include a methoxy group, an ethoxy group, a propoxy group, an n-butoxy group, a pentyloxy group, a hexyloxy group, and a heptyloxy group.

In the present specification, the aryloxy group is preferably an aryloxy group having 6 to 14 carbon atoms, and examples thereof include a phenoxy group, a naphthoxy group, and an anthryloxy group.

The alkylthio group is preferably an alkylthio group having 1 to 30 carbon atoms, and examples thereof include a methylthio group, an ethylthio group, and an n-hexadecylthio group.

The arylthio group is preferably an arylthio group having 6 to 30 carbon atoms, and examples thereof include a phenylthio group, a p-chlorophenylthio group, and an m-methoxyphenylthio group.

In the present specification, examples of the halogen atom include a fluorine atom, a chlorine atom, a bromine atom, and and an iodine atom.

In the present specification, examples of the aromatic ring include aromatic hydrocarbon rings such as a benzene ring, a naphthalene ring, an anthracene ring, a phenanthrene ring, a pyrene ring, a perylene ring, and a terylene ring; aromatic heterocyclic rings such as an indene ring, an azulene ring, a pyridine ring, a pyrazine ring, a pyrimidine ring, a pyrazole ring, a pyrazolidine ring, a thiazolidine ring, an oxazolidine ring, a pyran ring, a chromene ring, a pyrrole ring, a pyrrolidine ring, a benzimidazole ring, an imidazoline ring, an imidazolidine ring, an imidazole ring, a pyrazole ring, a triazole ring, a triazine ring, a diazole ring, an indoline ring, a thiophene ring, a thienothiophene ring, a furan ring, an oxazole ring, an oxadiazole ring, a thiazine ring, a thiazole ring, an indole ring, a benzothiazole ring, a benzothiadiazole ring, a naphthothiazole ring, a benzoxazole ring, a naphthoxazole ring, an indolenine ring, a benzindolenine ring, a quinoline ring, and a quinazoline ring; and fused aromatic rings such as a fluorene ring and a carbazole ring; among which aromatic rings having 5 to 16 carbon atoms (aromatic rings and fused rings containing aromatic rings) are preferable.

In addition, the aromatic ring may have a substituent, and the term "aromatic ring" means both an aromatic ring having a substituent and an aromatic ring having no substituent. As the substituent of the aromatic ring, the substituents described in Substituent group A to be mentioned later can be mentioned.

In the present specification, examples of the amino group include an amino group; an alkyl-substituted amino group such as a mono- or dimethylamino group, a mono- or diethylamino group, or a mono or di(n-propyl)amino group; an amino group substituted with an aromatic residue such as a mono- or diphenylamino group or a mono- or a dinaphthylamino group; an amino group substituted with one alkyl group and one aromatic residue, such as a monoalkylmonophenylamino group; a benzylamino group, an acetylamino group, and a phenylacetylamino group. Here, the aromatic residue means a group in which one hydrogen atom is removed from an aromatic ring, and the aromatic ring is as described above in the present specification.

The alkyl group, aryl group, heterocyclic group, ethenyl group, ethynyl group, amino group, acyl group, alkoxy group, aryloxy group, alkylthio group, or arylthio group represented by $R^{11}$ to $R^{15}$ may have a substituent.

Substituent group A:
a sulfamoyl group, a cyano group, an isocyano group, a thiocyanato group, an isothiocyanato group, a nitro group, a nitrosyl group, a halogen atom, a hydroxy group, an amino group, a mercapto group, an amido group, an alkoxy group, an aryloxy group, an alkylthio group, an arylthio group, a carbamoyl group, an acyl group, an aldehyde group, a carbonyl group, an aryl group, an alkyl group, an alkyl group substituted with a halogen atom, an ethenyl group, an ethynyl group, a silyl group, and a trialkylsilyl group (such as a trimethylsilyl group).

The alkyl group, aryl group, heterocyclic group, hydroxy group, alkoxy group, aryloxy group, alkylthio group, arylthio group, ethenyl group, or ethynyl group represented by $X^1$ and $X^2$ may have a substituent. Examples of the substituent include the substituents described in the Substituent group A.

The aryl group or heterocyclic group represented by $Ar^1$ and $Ar^2$ may have a substituent. Examples of the substituent include the substituents described in the Substituent group A.

The alkyl group, aryl group, heterocyclic group, ethenyl group, ethynyl group, amino group, acyl group, alkoxy group, aryloxy group, alkylthio group, or arylthio group represented by $R^{111}$ to $R^{116}$ may have a substituent. Examples of the substituent include the substituents described in the Substituent group A.

<Compound Represented by Formula (1)>

In Formula (1), $R^{11}$ to $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. At least three of $R^{11}, \ldots,$ or $R^{15}$ represent atoms or groups other than hydrogen atoms, preferably at least four of $R^{11}, \ldots,$ or $R^{15}$ represent atoms or groups other than hydrogen atoms, and more preferably all of $R^{11}$ to $R^{15}$ represent atoms or groups other than hydrogen atoms.

$R^{11}$ and $R^{15}$ may be the same or different atoms or groups, but are preferably the same atoms or groups. $R^{12}$ and $R^{14}$ may be the same or different atoms or groups, but are preferably the same atoms or groups.

$R^{12}$ and $R^{15}$ preferably represent a hydrogen atom, a halogen atom, an alkyl group, an aryl group, a heterocyclic group, an ethenyl group or an ethynyl group, each of which may have a substituent.

$R^{12}$ and $R^{14}$ preferably represent an alkyl group which may have a substituent.

$R^{13}$ preferably represents an aryl group which may have a substituent.

In Formula (1), $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and X and $X^2$ may be linked to each other to form a ring.

$X^1$ and $X^2$ preferably represent a halogen atom or an alkoxy group. $X^1$ and $X^2$ are more preferably a fluorine atom, a methoxy group, an ethoxy group, an isopropyloxy group, or a t-butyloxy group, each of which is also preferably substituted with a fluorine atom or an alkoxy group.

In Formula (1), $Ar^1$ and $Ar^2$ each independently represent an aryl group or a heterocyclic group, each of which may have a substituent.

In Formula (1), $L^1$ and $L^2$ each independently represent any one of Formulae (L-1) to (L-4).

Formula (L-1)

Formula (L-2)

Formula (L-3)

Formula (L-4)

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. A represents —O—, —S—, or —NH—.

$L^1$ and $L^2$ preferably represent any one of Formula (L-1) or Formula (L-2) and more preferably Formula (L-1).

$R^{111}$ to $R^{116}$ are preferably hydrogen atoms.

<As to Compound Represented by Formula (2)>

A preferred example of the compound represented by Formula (1) is a compound represented by Formula (2).

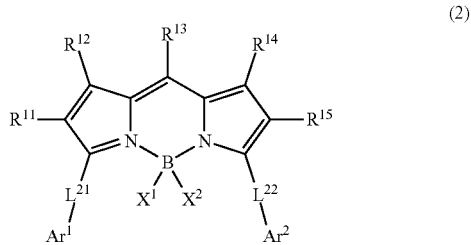

(2)

In the formula, $R^{11}$ to $R^{15}$, $X^1$, $X^2$, $Ar^1$, and $Ar^2$ are as defined in Formula (1), and the preferred ranges thereof are also the same as the preferred ranges in Formula (1). $L^{21}$ and $L^{22}$ each independently represent a group represented by Formula (L-1) or Formula (L-2). $L^{21}$ and $L^{22}$ preferably represent a group represented by the formula (L-1).

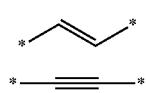

Formula (L-1)

Formula (L-2)

<As to Compound Represented by Formula (3)>

A preferred example of the compound represented by Formula (1) is a compound represented by Formula (3).

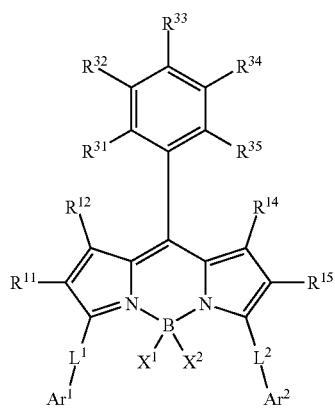

(3)

In Formula (3), $R^{11}$, $R^{12}$, $R^{14}$, $R^{15}$, $X^1$, $X^2$, $Ar^1$, $Ar^2$, $L^1$, and $L^2$ are as defined in Formula (1), and preferred ranges thereof are also the same as the preferred ranges in Formula (1). Here, at least two of $R^{11}$, $R^{12}$, $R^{14}$, or $R^{15}$ are atoms or groups other than hydrogen atoms, preferably at least three of $R^{11}$, $R^{12}$, $R^{14}$, or $R^{15}$ are atoms or groups other than hydrogen atoms, and more preferably $R^{11}$, $R^{12}$, $R^{14}$, and $R^{15}$ are atoms or groups other than hydrogen atoms.

In Formula (3), $R^{31}$ to $R^{35}$ each independently represent a hydrogen atom, a halogen atom, an alkyl group, an aryl group, a heterocyclic group, an ethenyl group, an ethynyl group, an amino group, a cyano group, an acyl group, an alkoxy group, an aryloxy group, an alkylthio group, or an arylthio group, each of which may have a substituent (examples of the substituent include the substituents described in the Substituent group A), and any one of $R^{31}$, $R^{32}$, $R^{34}$, or $R^{35}$ is a group consisting of two or more atoms. The group consisting of two or more atoms is preferably an alkyl group, an aryl group, an ethenyl group, an ethynyl group, an amino group, a cyano group, or an alkoxy group and more preferably an alkyl group. Among the alkyl groups, an alkyl group consisting only of carbon atoms and hydrogen atoms or an alkyl group substituted with a halogen atom is preferable; an alkyl group consisting only of 1 to 6 carbon atoms and hydrogen atoms or an alkyl group substituted with a fluorine atom is more preferable; a methyl group, an isopropyl group, a t-butyl group, or a trifluoromethyl group is still more preferable; and a methyl group is particularly preferable.

<As to Compound Represented by Formula (4)>

A preferred example of the compound represented by Formula (1) is a compound represented by Formula (4).

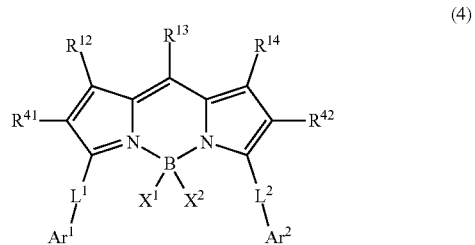

(4)

In Formula (4), $R^{12}$, $R^{13}$, $R^{14}$, $X^1$, $X^2$, $Ar^1$, $Ar^2$, $L^1$, and $L^2$ are as defined in Formula (1), and the preferred ranges thereof are also the same as the preferred ranges in Formula (1). Here, at least one of $R^{12}$, $R^{13}$, or $R^{14}$ is an atom or group other than a hydrogen atom, preferably at least two of $R^{12}$, $R^{13}$, or $R^{14}$ are atoms or groups other than hydrogen atoms, and more preferably $R^{12}$, $R^{13}$, and $R^{14}$ are atoms or groups other than hydrogen atoms.

In Formula (4), $R^{41}$ and $R^{42}$ each independently represent an aryl group, a heterocyclic group, an ethenyl group, or an ethynyl group, each of which may have a substituent. Examples of the substituent include the substituents described in the Substituent group A. $R^{41}$ and $R^{42}$ are each independently preferably an aryl group, an ethenyl group, or an ethynyl group, from the viewpoint of improving a quantum yield, an aryl group is preferable, and from the viewpoint of increasing a wavelength, an ethenyl group or an ethynyl group is preferable. In a case of an aryl group, it is preferable to have at least one substituent at the ortho or meta position of the aryl group, and it is more preferred to have at least one substituent at the ortho position of the aryl group. The number of the substituent substituted in the aryl group is preferably 1 to 3 and more preferably 2 or 3. The substituent substituted in the aryl group is preferably an alkyl group, more preferably a methyl group, an isopropyl group, or a t-butyl group, and still more preferably a methyl group.

<As to Compound Represented by Formula (5)>

A preferred example of the compound represented by Formula (1) is a compound represented by Formula (5).

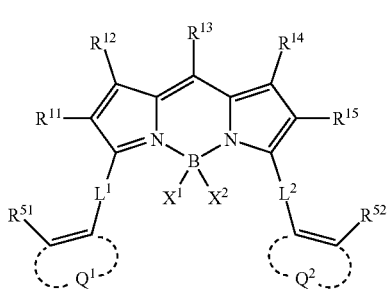

(5)

In Formula (5), $R^{11}$ to $R^{15}$, $X^1$, $X^2$, $L^1$, and $L^2$ are as defined in Formula (1), and the preferred ranges thereof are also the same as the preferred ranges in Formula (1).

In Formula (5), $R^{51}$ and $R^{52}$ each independently represent an alkyl group, an aryl group, a heteroaryl group, an amino group, an acyl group, an alkoxy group, an aryloxy group, an alkylthio group, or an arylthio group, each of which may have a substituent. Examples of the substituent include the substituents described in the Substituent group A. $R^{51}$ and $R^{52}$ each independently are preferably an alkyl group or an alkoxy group, and from the viewpoint of improving a quantum yield, more preferably an alkyl group, still more preferably a methyl group, an ethyl group, an isopropyl group, or a t-butyl group, and particularly preferably a methyl group. From the viewpoint of increasing a wavelength, $R^{51}$ and $R^{52}$ each independently are more preferably an alkoxy group, still more preferably a methoxy group, an ethoxy group, an isopropyloxy group, or a t-butyloxy group, and particularly preferably a methoxy group.

$Q^1$ and $Q^2$ each independently represent an aromatic hydrocarbon ring or an aromatic heterocyclic ring, each of which may have a substituent. Examples of the substituent include the substituents described in the Substituent group A. $Q^1$ and $Q^2$ are each preferably an aromatic hydrocarbon ring, more preferably a benzene ring, a naphthalene ring, an anthracene ring, a phenanthrene ring, or a pyrene ring, still more preferably a benzene ring or a naphthalene ring, and particularly preferably a benzene ring. As the group containing $R^{51}$ and forming $Q^1$ and the group containing $R^{52}$ and forming $Q^2$, a tolyl group, a xylyl group, or a mesityl group is preferable; a xylyl group or a mesityl group is more preferable; a xylyl group having methyl groups at both ends of the ortho position relative to the bonding position with $L^1$ or $L^2$, or a mesityl group having methyl groups at both ends of the ortho position and at the para position relative to the bonding position with $L^1$ or $L^2$ is still more preferable; and a mesityl group having methyl groups at both ends of the ortho position and at the para position relative to the bonding position with $L^1$ or $L^2$ is particularly preferable.

<As to Compound Represented by Formula (6)>

The compound represented by Formula (5) is more preferably a compound represented by Formula (6).

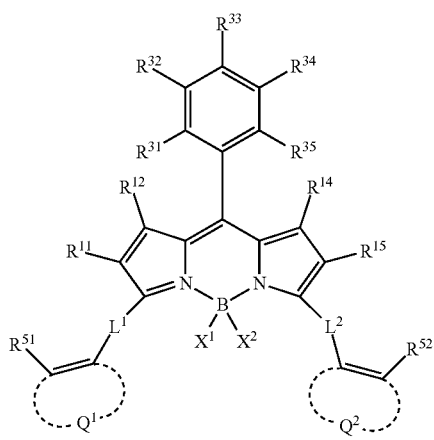

(6)

In the formula, $R^{11}$, $R^{12}$, $R^{14}$, and $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent, and at least two of $R^{11}$, $R^{12}$, $R^{14}$, or $R^1$ are atoms or groups other than hydrogen atoms.

$X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $X^1$ and $X^2$ may be linked to each other to form a ring.

$R^{31}$ to $R^{35}$ each independently represent a hydrogen atom, a halogen atom, an alkyl group, an aryl group, a heterocyclic group, an ethenyl group, an ethynyl group, an amino group, an acyl group, a cyano group, an alkoxy group, an aryloxy group, an alkylthio group, or an arylthio group, each of which may have a substituent, and any one of $R^{31}, \ldots,$ or $R^{35}$ is a hydrogen atom.

$R^{51}$ and $R^{52}$ each independently represent an alkyl group, an aryl group, a heteroaryl group, an amino group, an acyl group, an alkoxy group, an aryloxy group, an alkylthio group, or an arylthio group, each of which may have a substituent.

$Q^1$ and $Q^2$ each independently represent an aromatic hydrocarbon ring or an aromatic heterocyclic ring, each of which may have a substituent.

$L^1$ and $L^2$ each independently represent any one of Formulae (L-1) to (L-4).

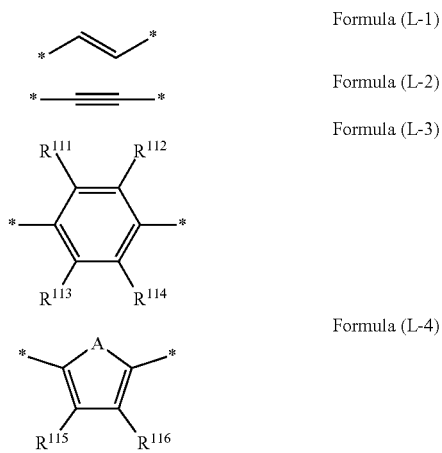

Formula (L-1)

Formula (L-2)

Formula (L-3)

Formula (L-4)

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. A represents —O—, —S—, or —NH—.

$R^{11}$ and $R^{15}$ are each independently preferably an alkyl group, an aryl group, a heterocyclic group, an ethenyl group, an ethynyl group, or an amino group, more preferably that as defined in $R^{41}$ and $R^{42}$, that is, an aryl group, a heterocyclic group, an ethenyl group, or an ethynyl group, and still more preferably an aryl group, an ethenyl group, or an ethynyl group. From the viewpoint of improving a quantum yield, an aryl group is more preferable, and from the viewpoint of increasing a wavelength, an ethenyl group or an ethynyl group is more preferable. In a case of an aryl group, it is preferable to have at least one substituent at the ortho or meta position of the aryl group, and it is more preferred to have at least one substituent at the ortho position of the aryl group. The number of the substituent substituted in the aryl group is preferably 1 to 3 and more preferably 2 or 3. The substituent substituted in the aryl group is preferably an alkyl group, more preferably a methyl group, an isopropyl group, or a t-butyl group, and still more preferably a methyl group.

<Specific Examples of Compounds Represented by Formulae (1) to (6)>
Specific examples of the compounds represented by Formulae (1) to (6) are shown below. Me represents a methyl group, Et represents an ethyl group, and iPr represents an isopropyl group.
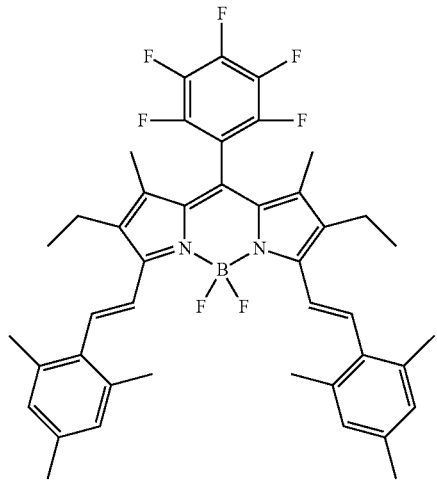
F-1
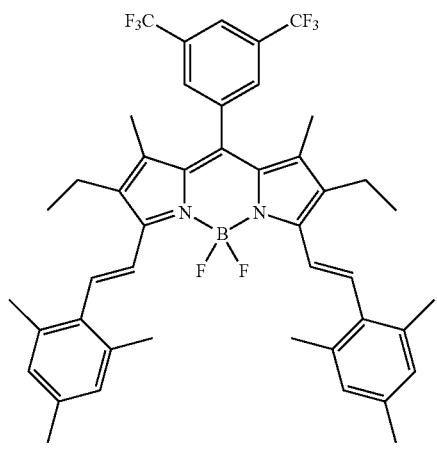
F-2
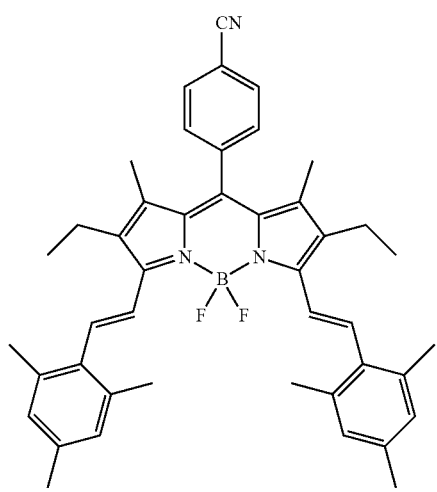
F-3
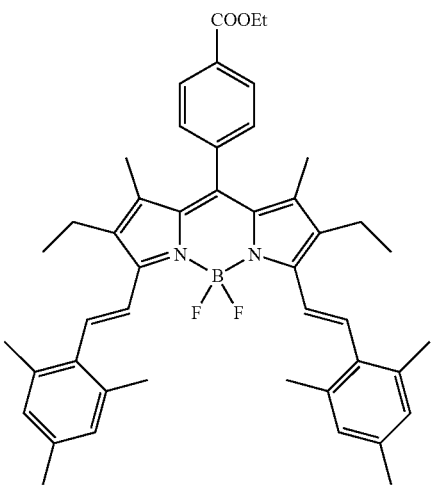
F-4
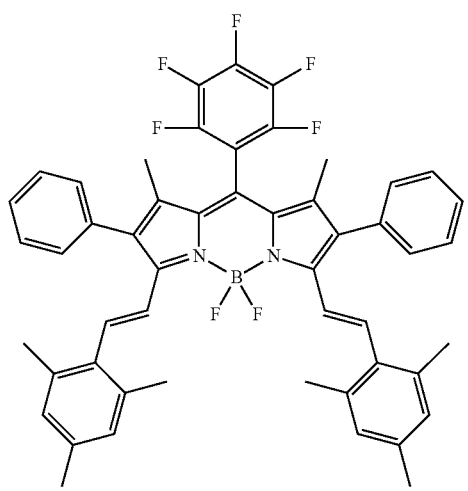
F-5
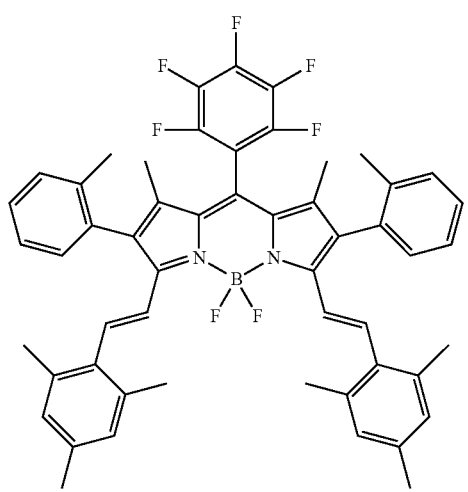
F-6

F-7
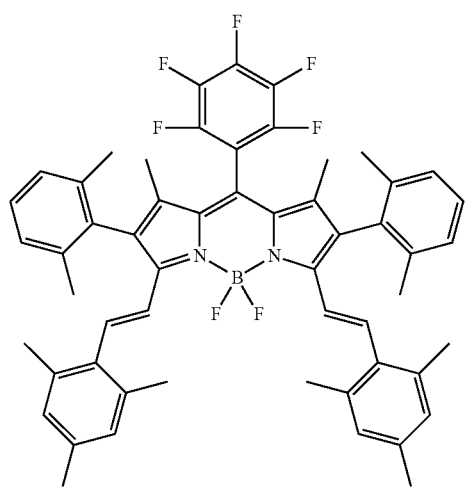
F-8
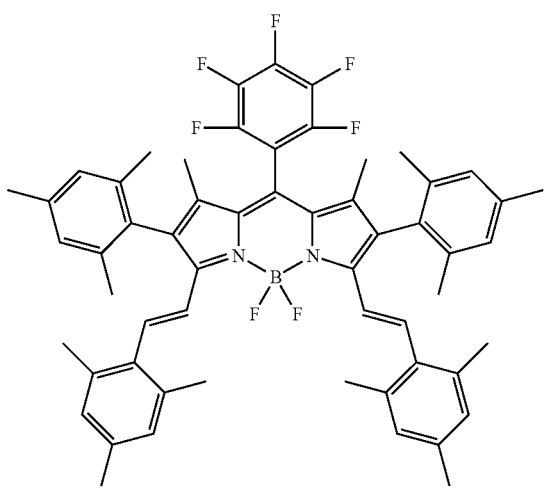
F-9
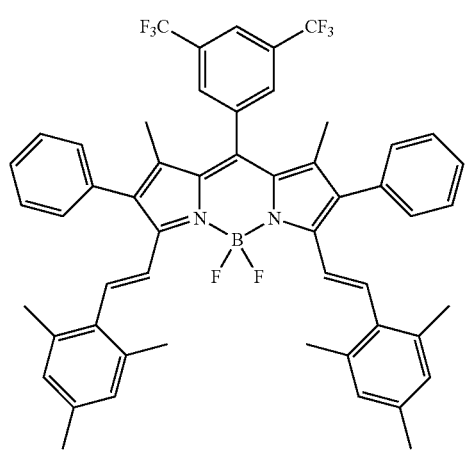
F-10
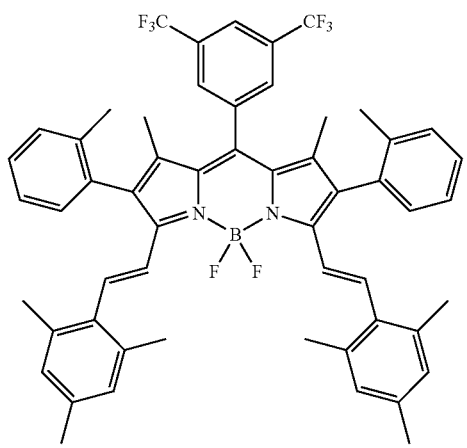
F-11
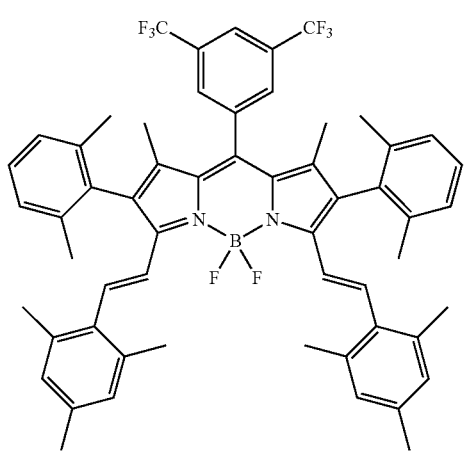
F-12
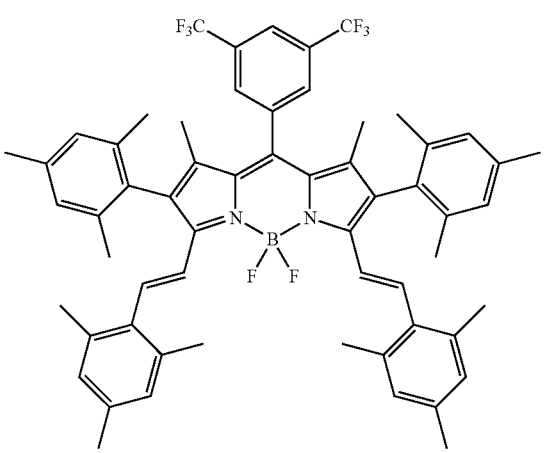

-continued
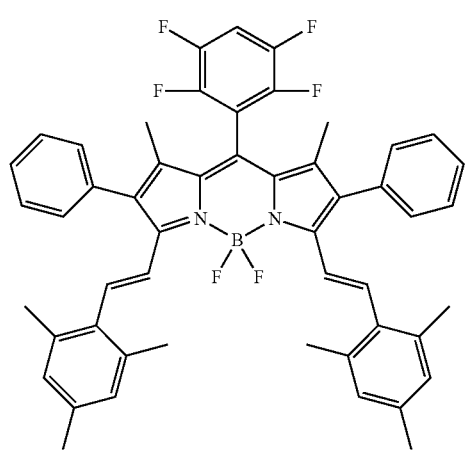
F-13
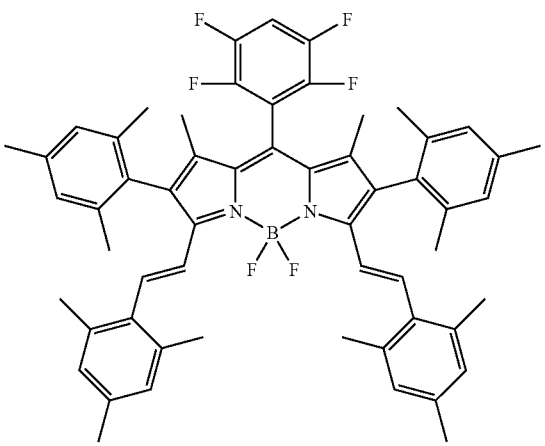
F-16
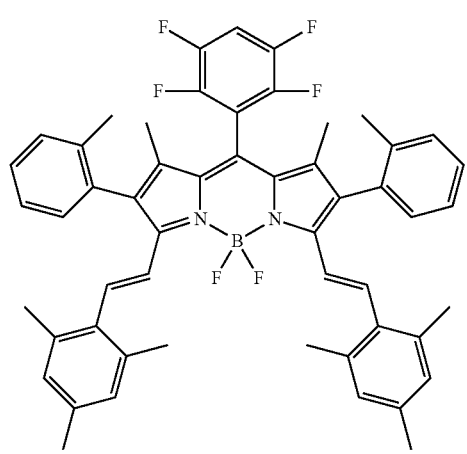
F-14
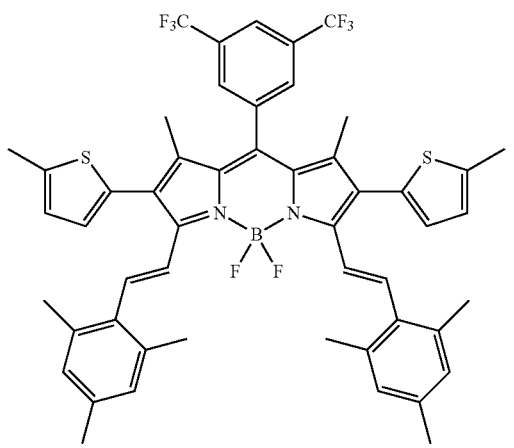
F-17
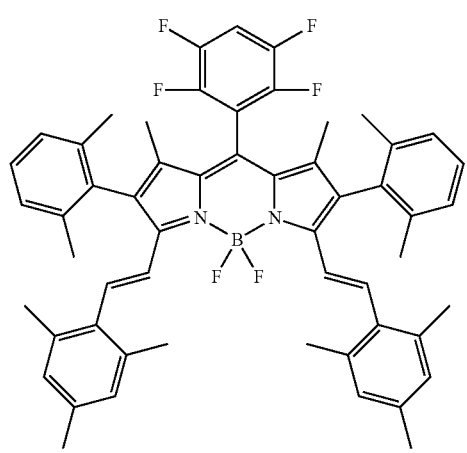
F-15
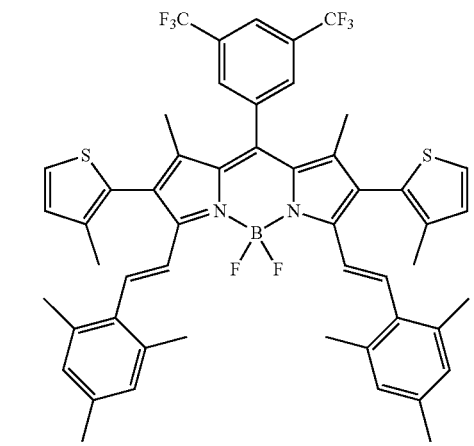
F-18

-continued
F-19
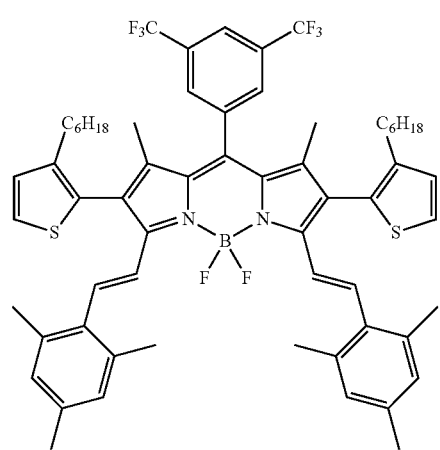
F-20
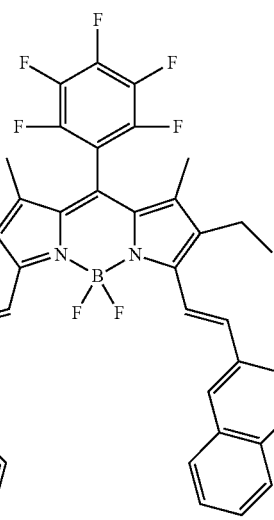
F-21
F-22
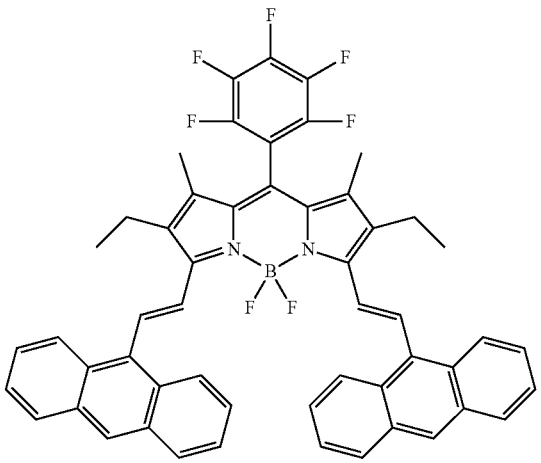
F-23
F-24
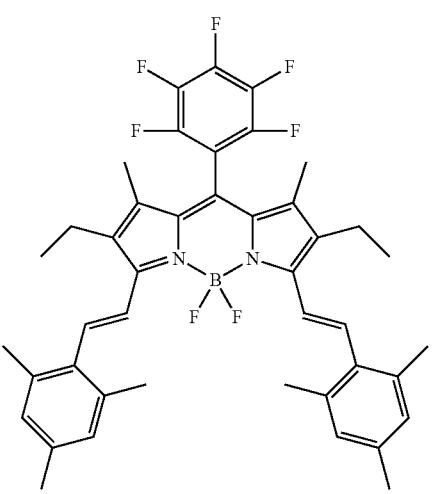

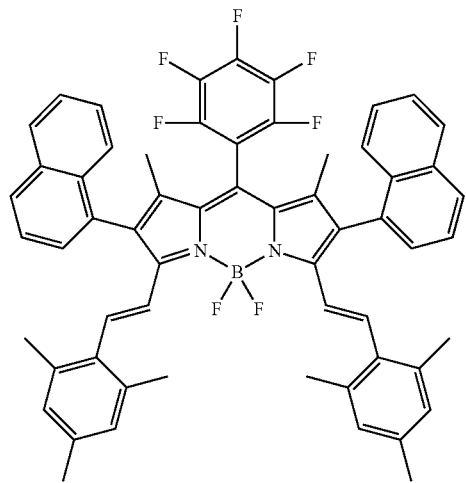
F-25
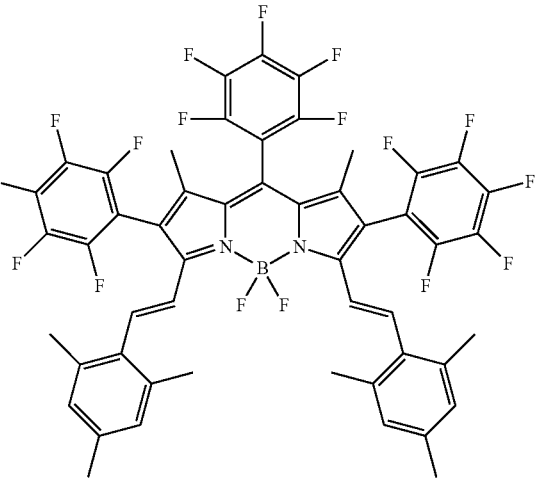
F-28
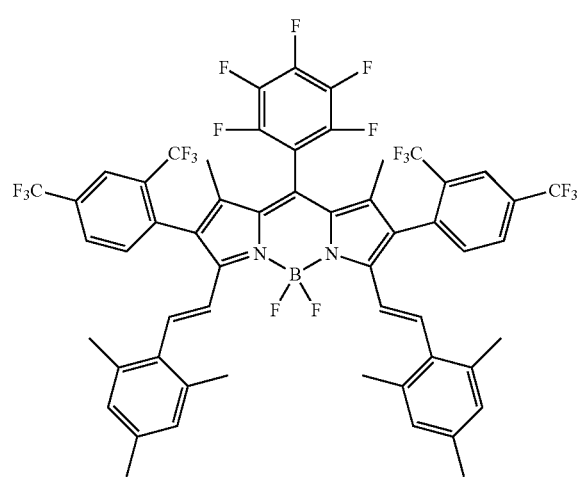
F-26
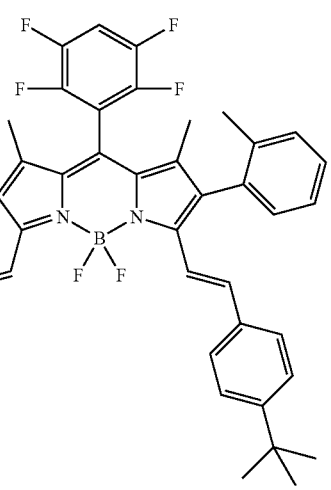
F-29
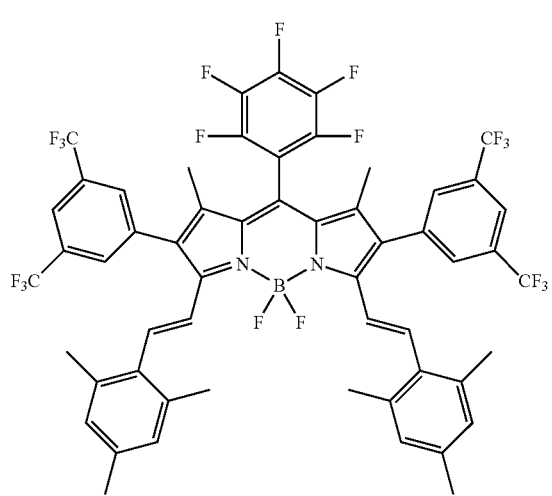
F-27
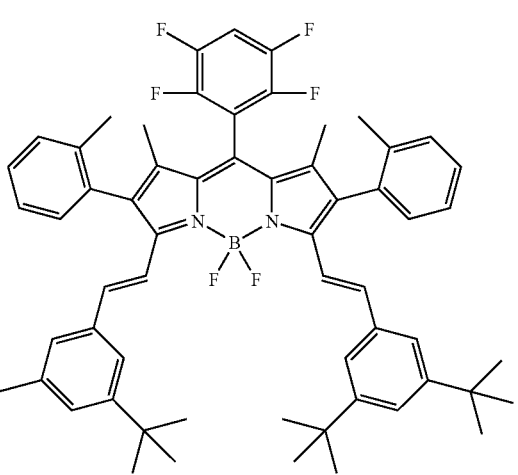
F-30

-continued
F-31
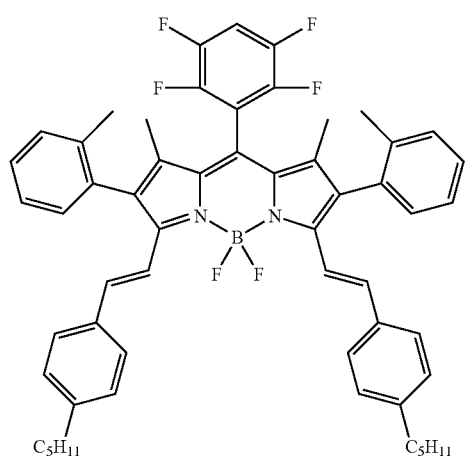
F-34
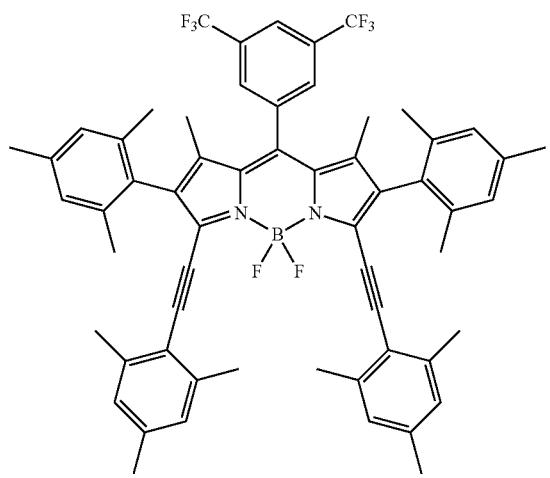
F-32
F-35
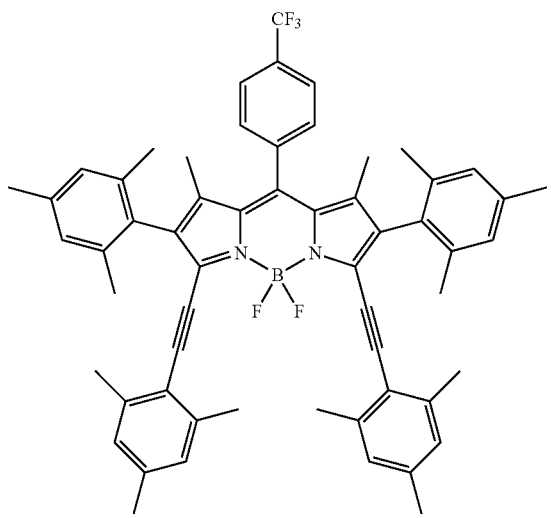
F-33
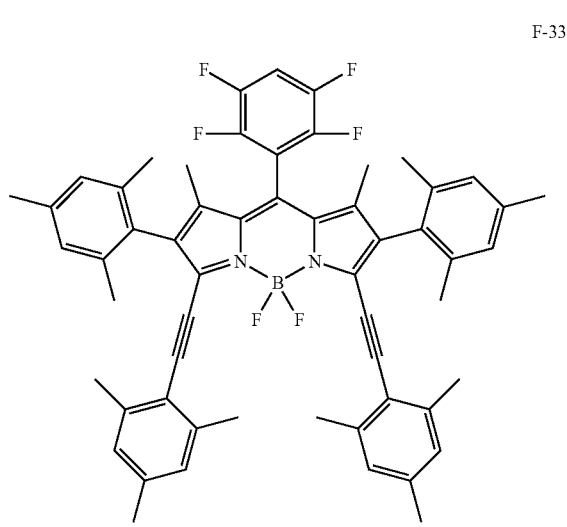
F-36
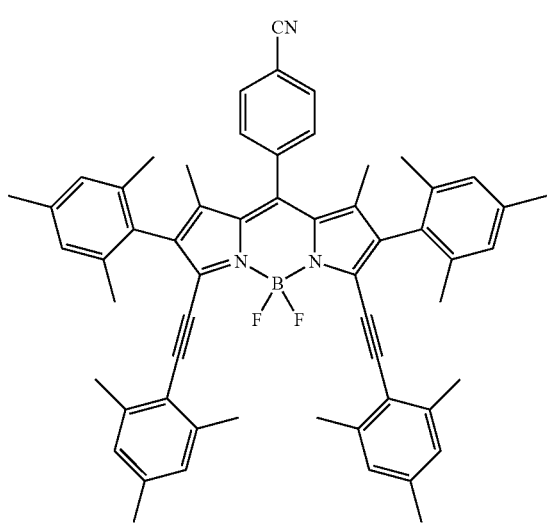

-continued
F-37
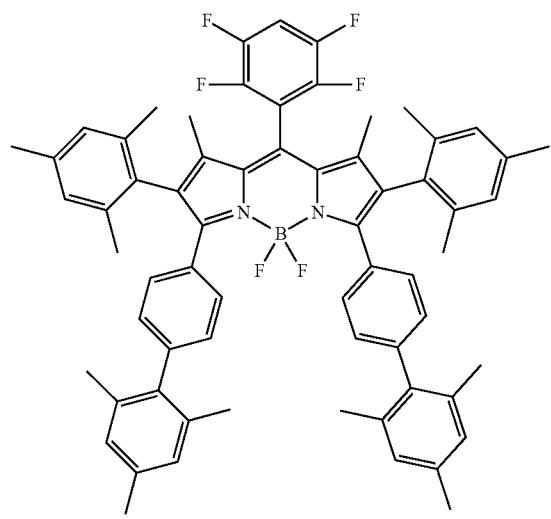
F-38
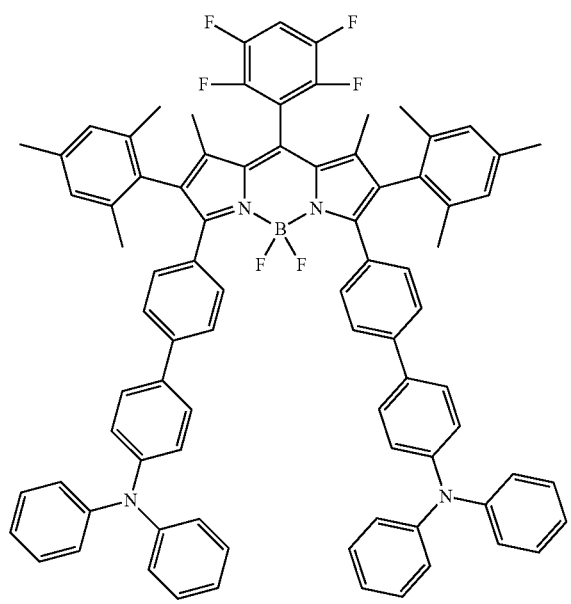
F-39
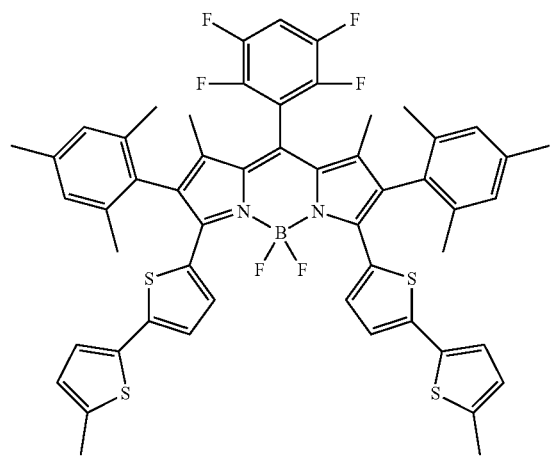
-continued
F-40
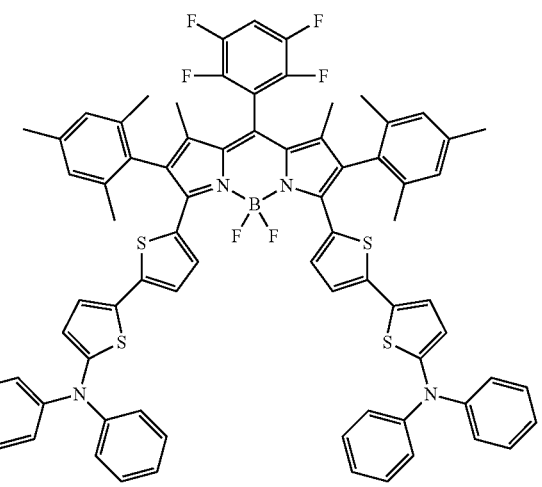
F-41
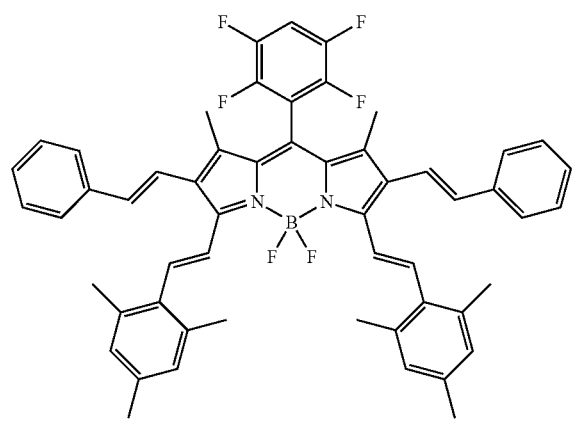
F-42
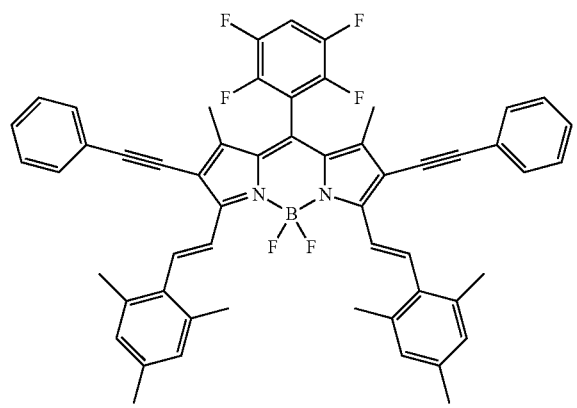

-continued
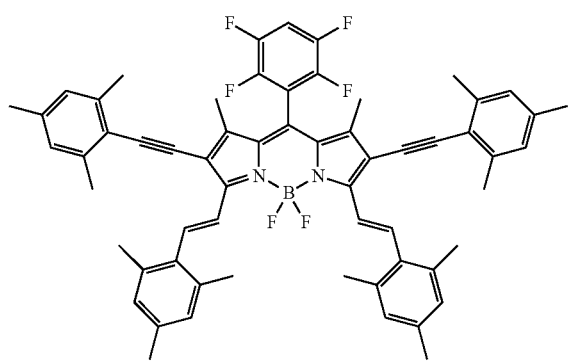
F-43
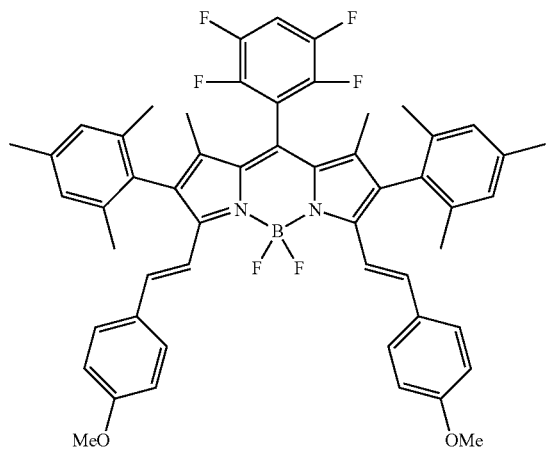
F-46
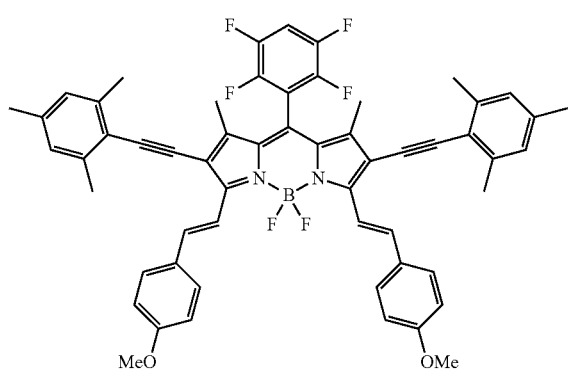
F-44
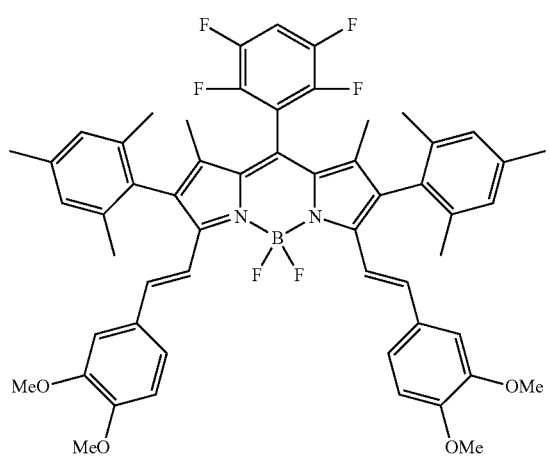
F-47
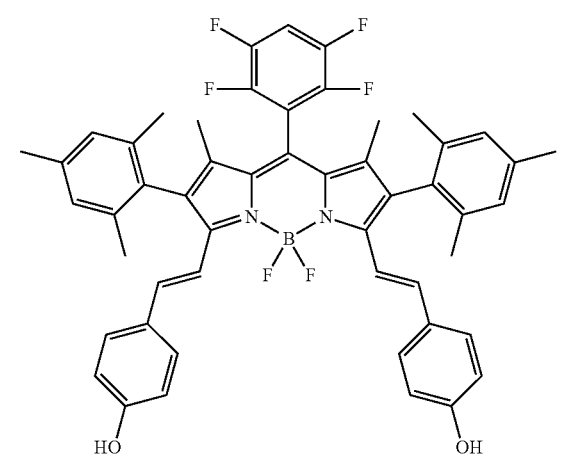
F-45
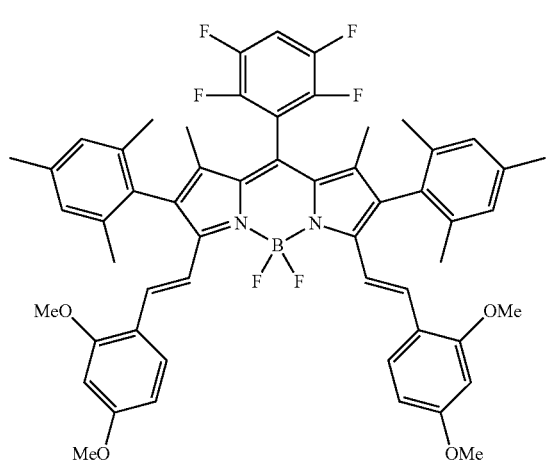
F-48

-continued
F-49
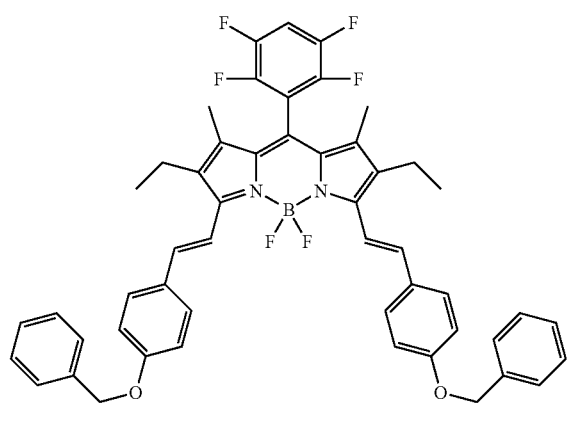
F-50
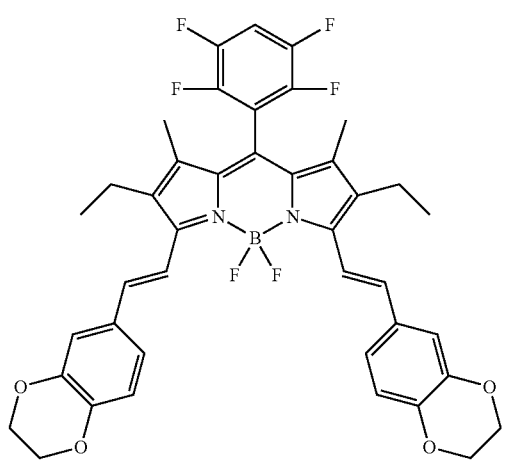
F-51
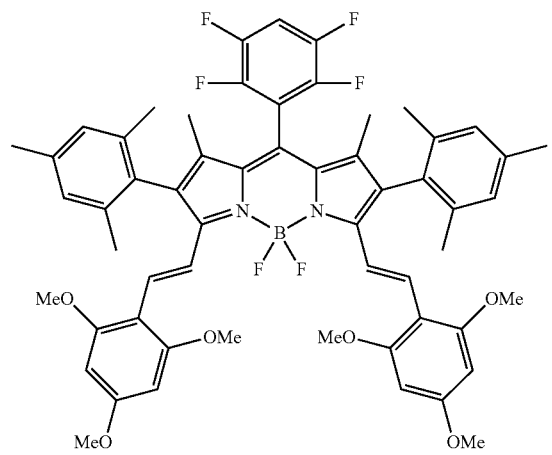
-continued
F-52
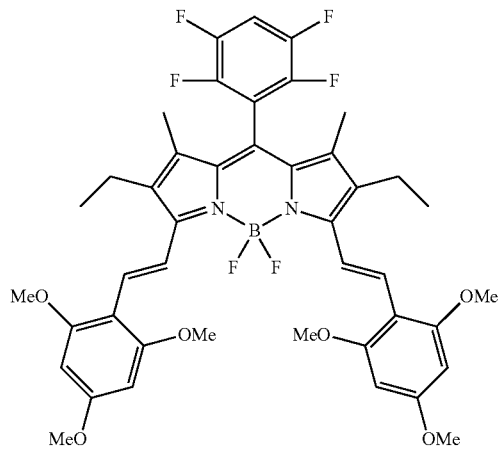
F-53
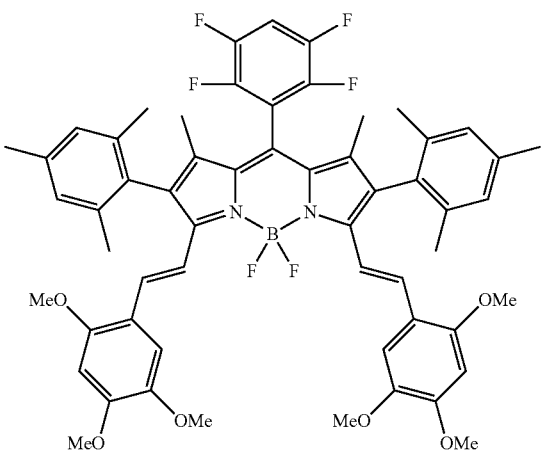
F-54
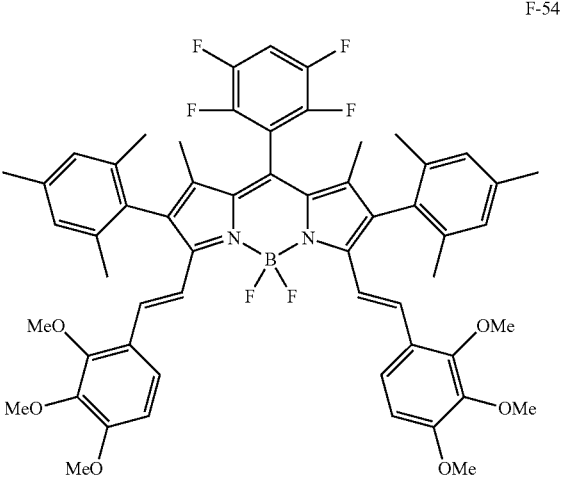

F-55
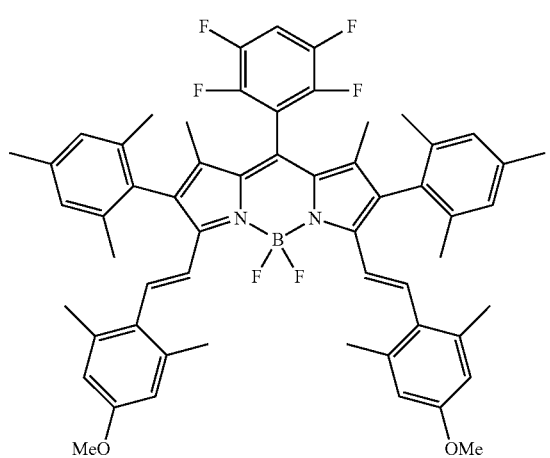
F-56
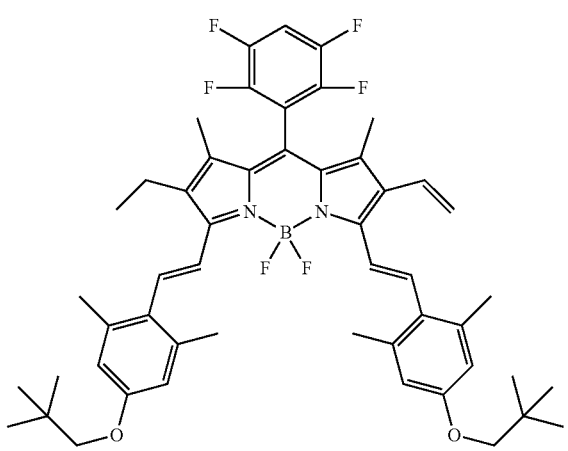
F-57
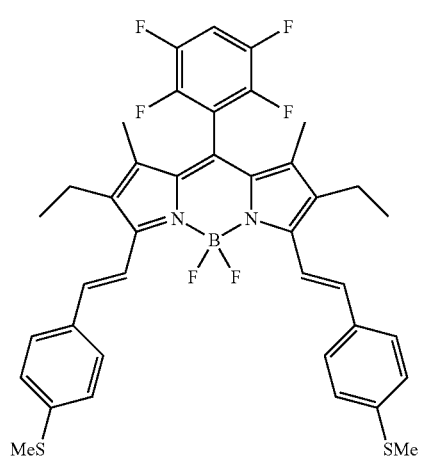
F-58
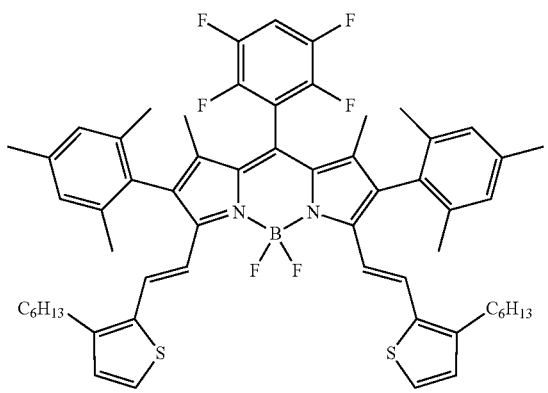
F-59
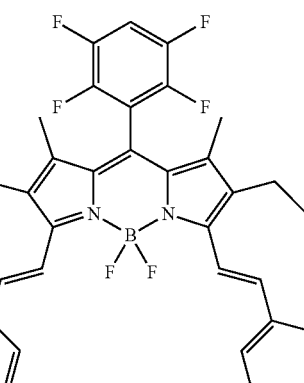
F-60
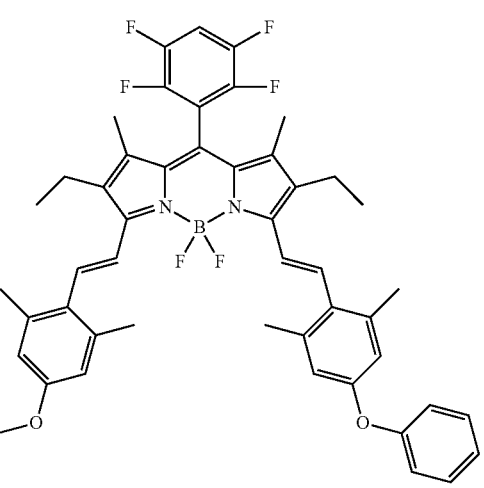

-continued
F-61
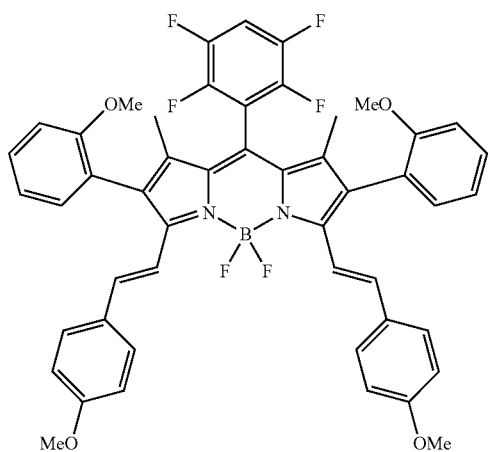
F-64
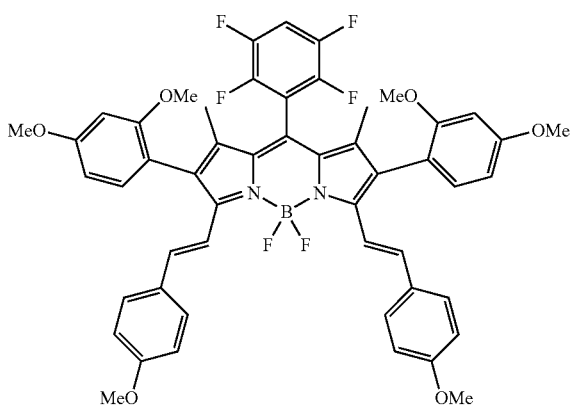
F-62
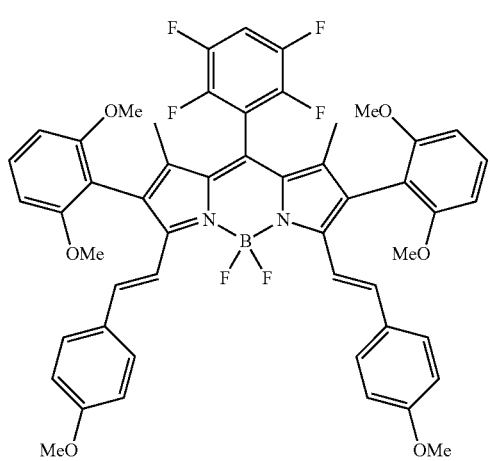
F-65
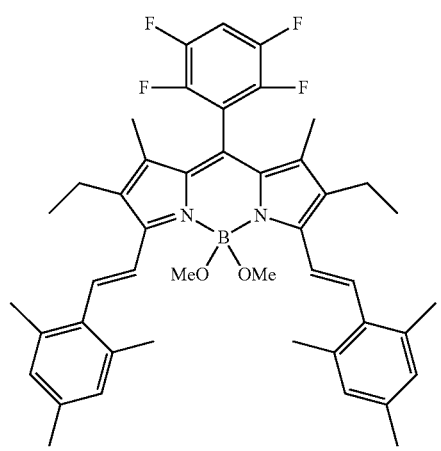
F-63
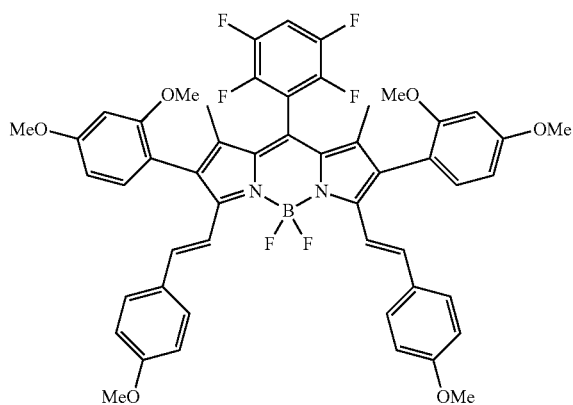
F-66
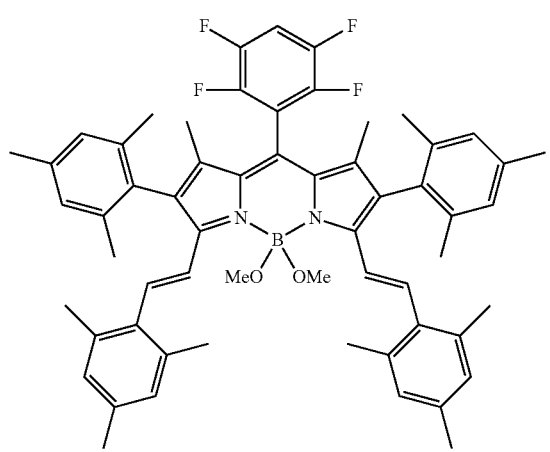

-continued
F-67
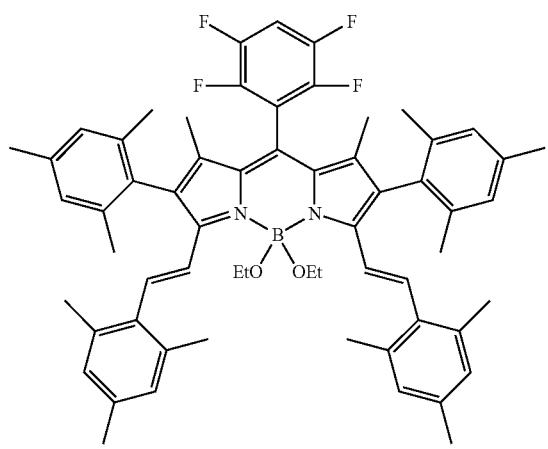
F-70
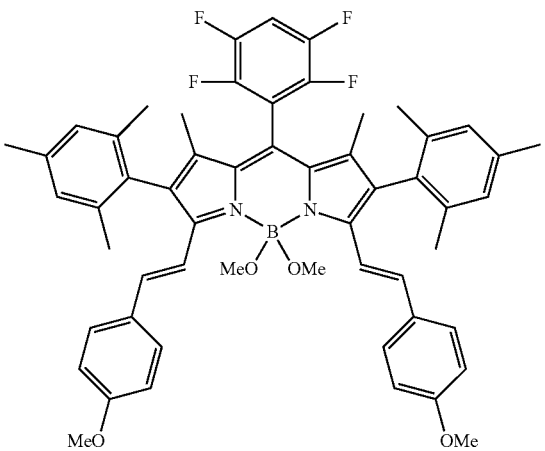
F-68
F-71
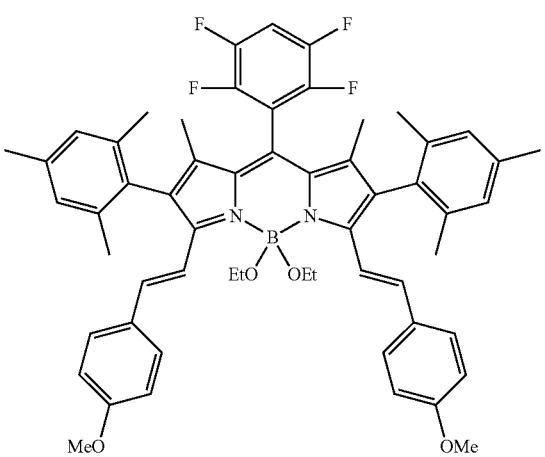
F-69
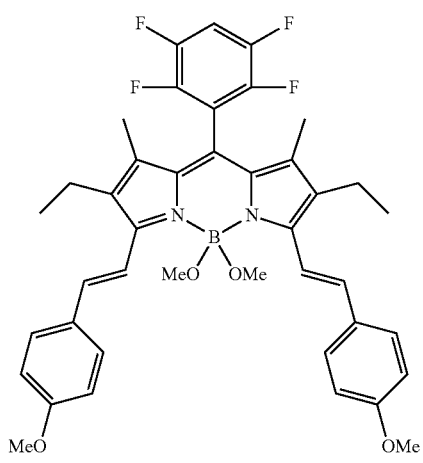
F-72
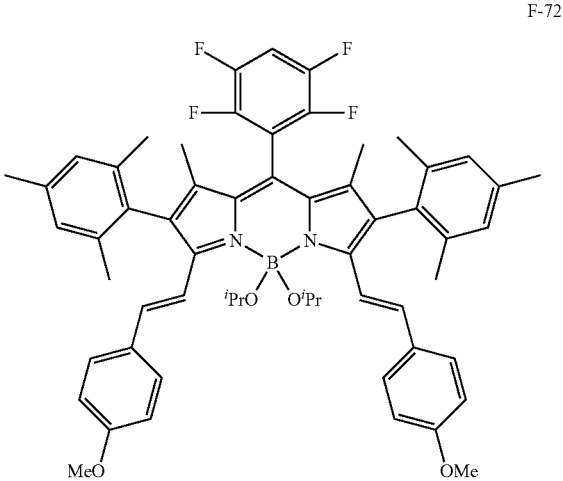

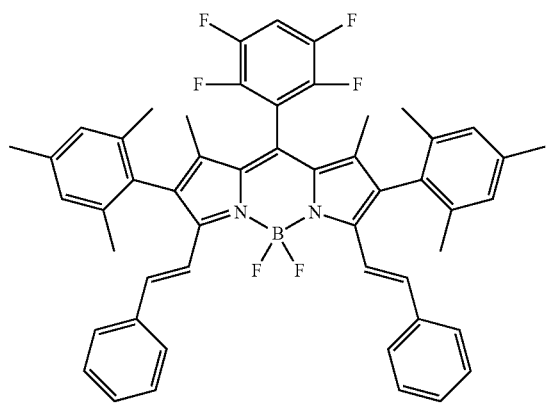
73
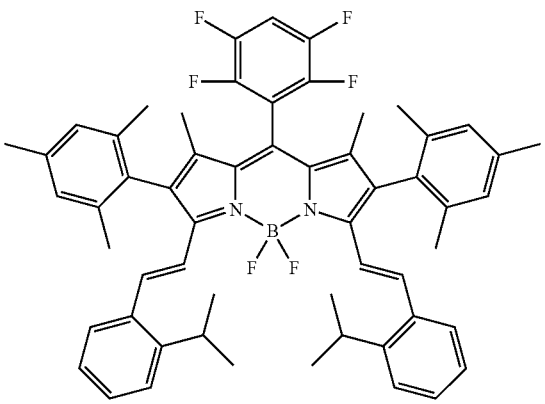
73
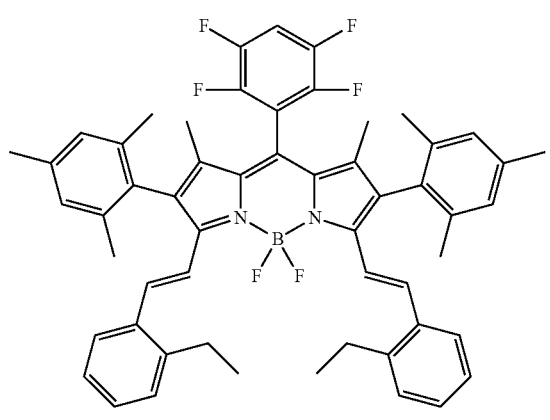
73
F-74
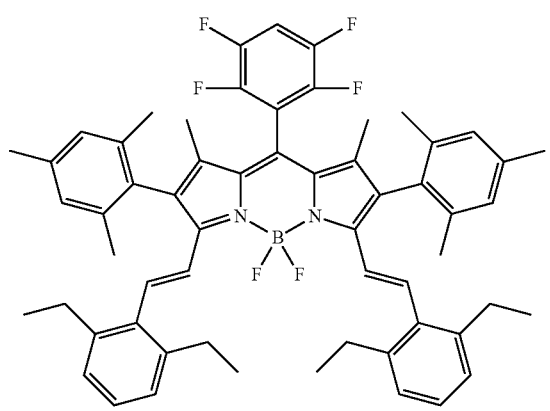
73
F-75

F-76
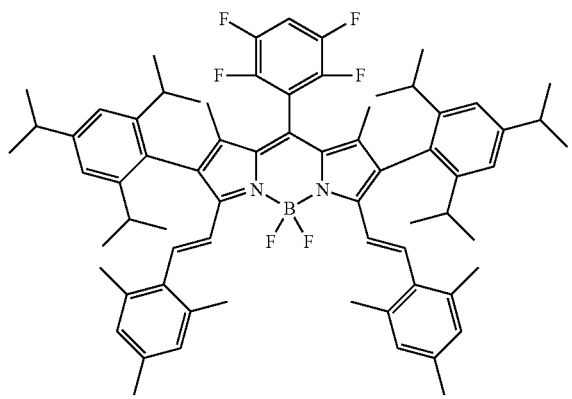
F-79
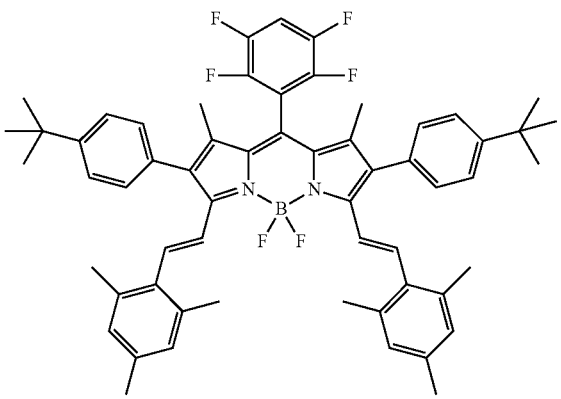
F-77
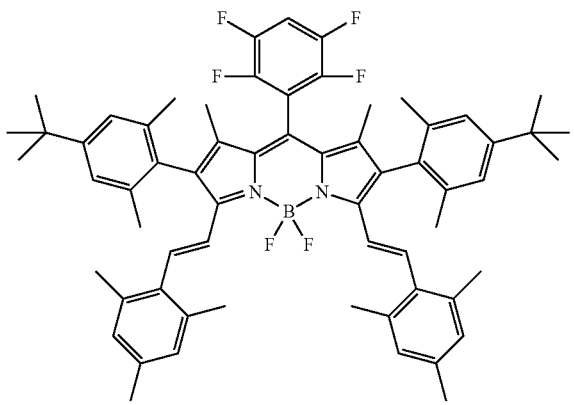
F-80
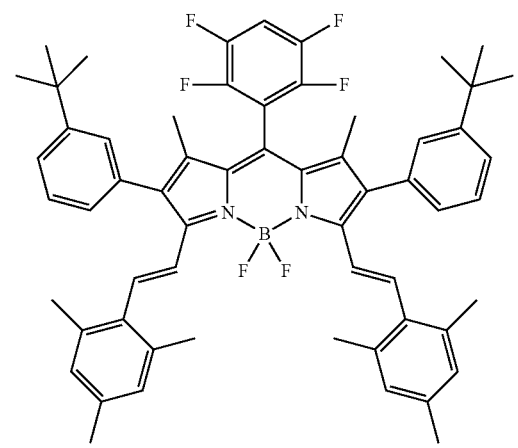
F-78
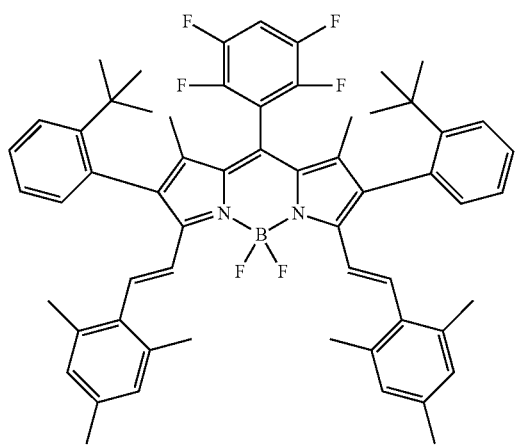
F-81
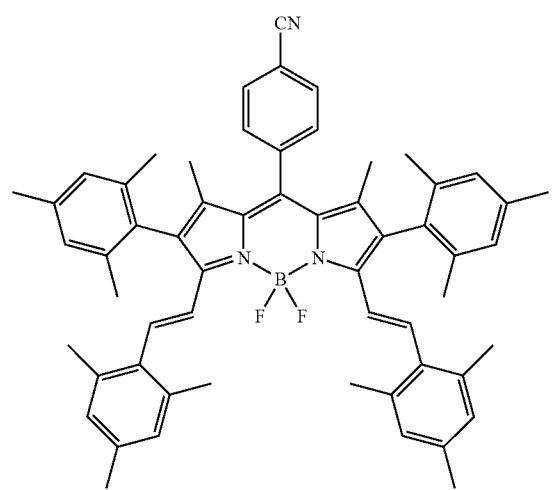

-continued
F-82
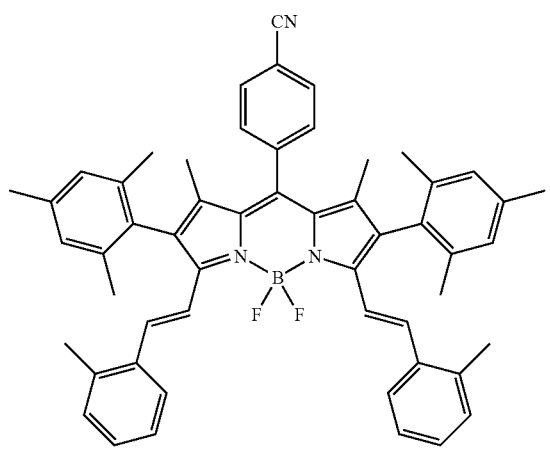
F-83
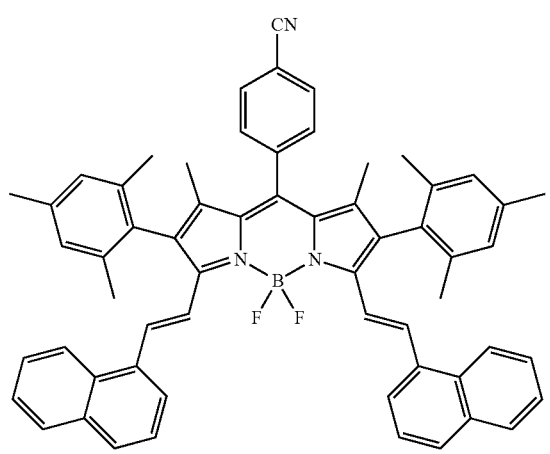
F-84
-continued
F-85
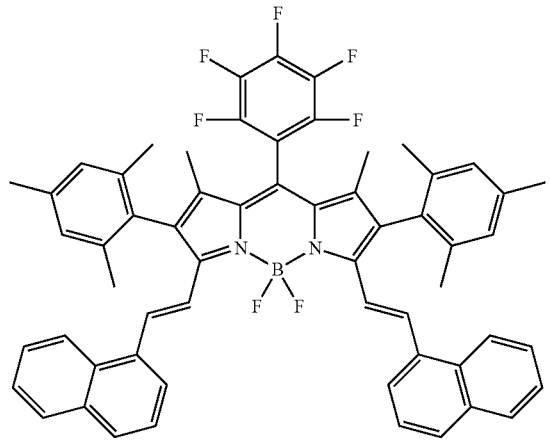
F-86
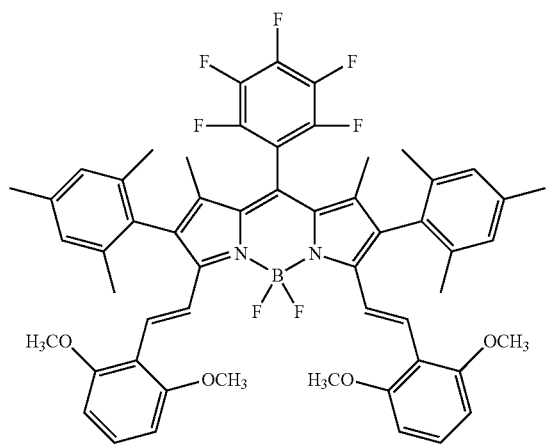
F-87
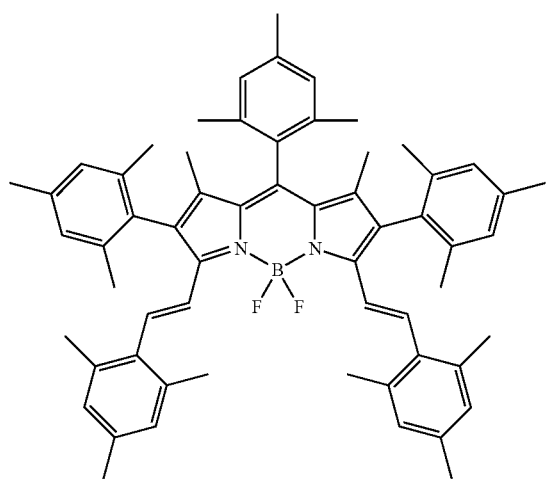

F-88
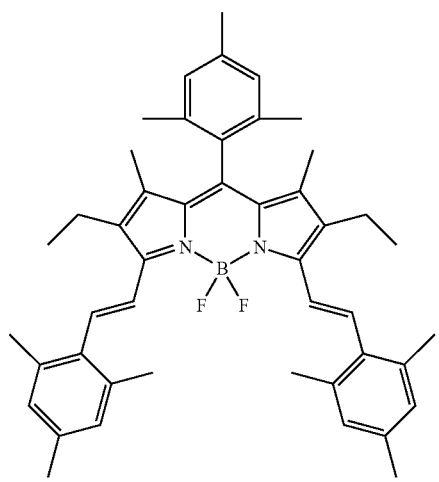
F-89
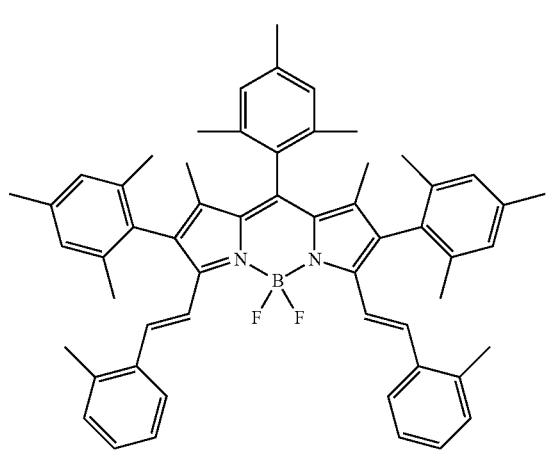
F-90
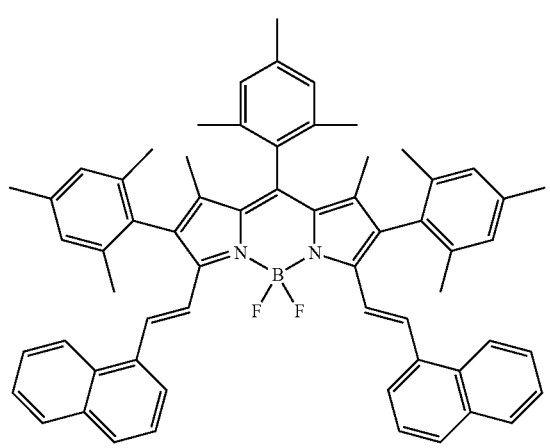
F-91
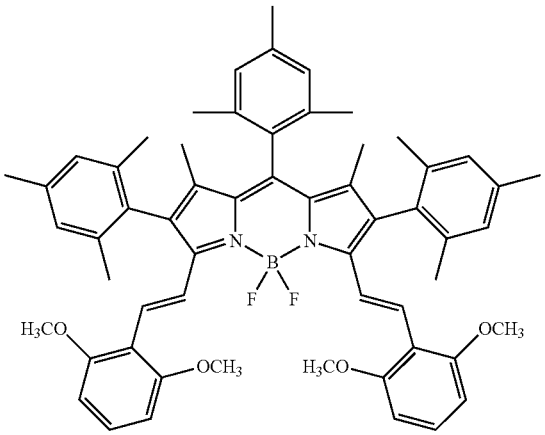
F-92
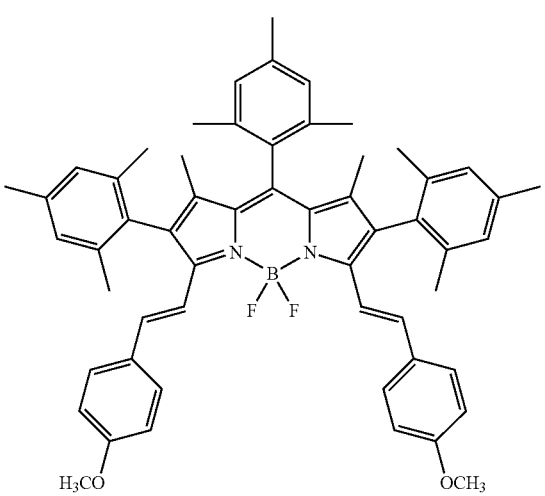
F-93
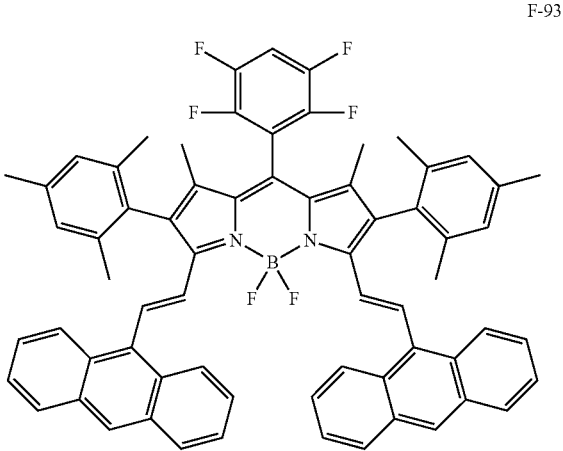

-continued

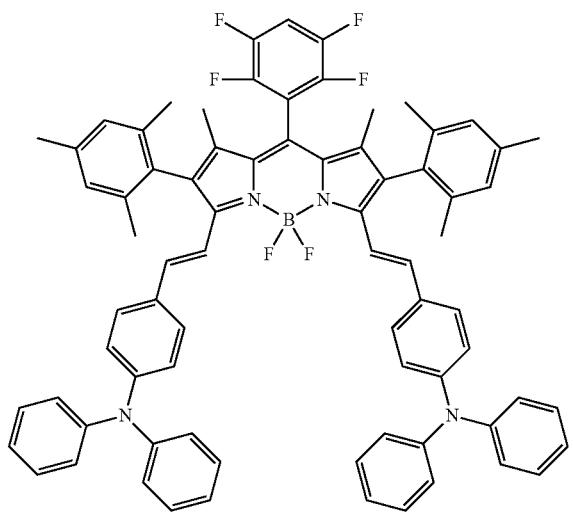

F-94

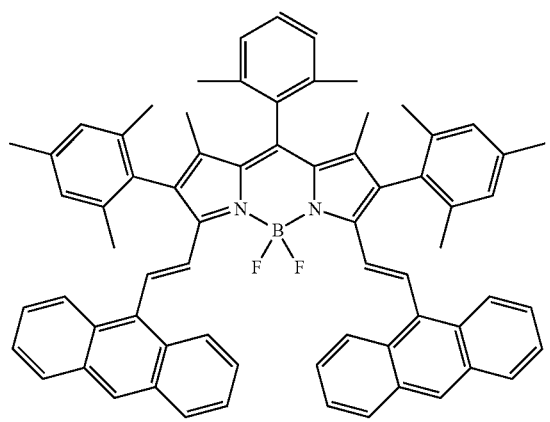

F-95

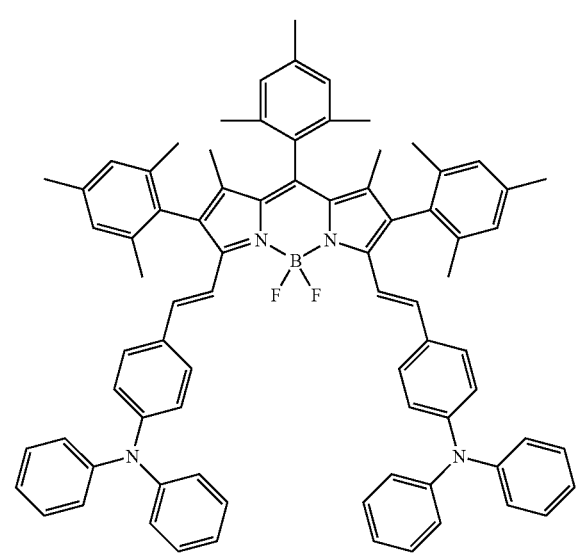

F-96

The labeled particle may be a labeled particle containing at least one kind of energy donor compound, at least one kind of energy acceptor compound, and a particle, and in such a case, at least one kind of the energy donor compound or the energy acceptor compound may be the compound represented by Formula (1).

In another example of the present invention, a luminescent particle contains the compound represented by Formula (1) as one of an energy donor compound or an energy acceptor compound, and a compound represented by Formula (10) as the other of an energy donor compound or an energy acceptor compound. That is, the luminescent particle may be a luminescent particle containing the compound represented by Formula (1) as the energy donor compound and the compound represented by Formula (10) as the energy acceptor compound, or may be a luminescent particle containing the compound represented by Formula (1) as the energy acceptor compound and the compound represented by Formula (10) as the energy donor compound.

<Compound Represented by Formula (10)>

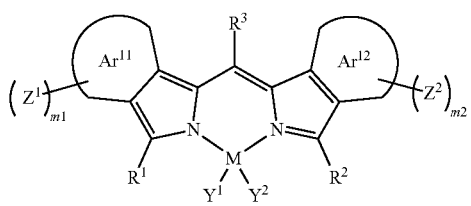

(10)

In Formula (10), m1 and m2 each independently represent an integer of 0 to 4, and any one of m1 or m2 is at least one. M represents a metalloid atom or a metal atom. $R^1$, $R^2$, and $R^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, each of which may have a substituent. $Y^1$ and $Y^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $Y^1$ and $Y^2$ may be linked to each other to form a ring. $Ar^{11}$ and $Ar^{12}$ each independently represent an aromatic ring which may have a substituent. $Z^1$ and $Z^2$ each independently represent an aryl group, a heterocyclic group, or an amino group, each of which may have a substituent. In a case where m1 is two or more, a plurality of $Z^1$'s may be the same group or different groups, and in a case where m2 is two or more, a plurality of $Z^2$'s may be the same group or different groups.

In Formula (10), m1 and m2 each independently represent an integer of 0 to 4, and preferably both m1 and m2 are one or more. m1 and m2 may be the same integer or different integers, and are preferably the same integer. Preferably, m1 and m2 are each independently one or two, more preferably, both m1 and m2 are one or two, and particularly preferably both m1 and m2 are one.

In Formula (10), M represents a metalloid atom or a metal atom, preferably a metalloid atom, and particularly preferably a boron atom.

In Formula (10), $R^1$, $R^2$, and $R^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, each of which may have a substituent.

Preferably, $R^1$ and $R^2$ each independently represent an aryl group or a heterocyclic group, each of which may have a substituent.

$R^1$ and $R^2$ may be the same as or different from each other, and are preferably the same as each other.

$R^1$ and $R^2$ are not linked to each other to form a ring.

Preferably, $R^3$ represents a hydrogen atom, an alkyl group, an aryl group, or a heterocyclic group, each of which may have a substituent. More preferably, $R^3$ is a hydrogen atom.

In Formula (10), $Y^1$ and $Y^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $Y^1$ and $Y^2$ may be linked to each other to form a ring.

Preferably, $Y^1$ and $Y^2$ each independently represent a halogen atom, an alkyl group, an aryl group, a hydroxy group, an alkoxy group, or an aryloxy group, each of which may have a substituent, and $Y^1$ and $Y^2$ may be linked to each other to form a ring.

More preferably, $Y^1$ and $Y^2$ are each independently halogen atoms.

Still more preferably, $Y^1$ and $Y^2$ are fluorine atoms.

$Y^1$ and $Y^2$ may be the same as or different from each other, and are preferably the same as each other.

In Formula (10), $Ar^{11}$ and $Ar^{12}$ each independently represent an aromatic ring which may have a substituent.

Preferably, $Ar^{11}$ and $Ar^{12}$ each represent a benzene ring.

In Formula (10), $Z^1$ and $Z^2$ each independently represent an aryl group, a heterocyclic group, or an amino group, each of which may have a substituent. In a case where m1 is two or more, a plurality of $Z^1$'s may be the same group or different groups, and in a case where m2 is two or more, a plurality of $Z^2$'s may be the same group or different groups.

Preferably, $Z^1$ and $Z^2$ each independently represent an aryl group which may have a substituent.

More preferably, $Z^1$ and $Z^2$ each independently represent a phenyl group, a naphthyl group, or an anthryl group, each of which may have a substituent.

Preferably, in a case where m1 is two or more, a plurality of Z's are the same group.

Preferably, in a case where m2 is two or more, a plurality of $Z^2$'s are the same group.

It is preferable that the compound represented by Formula (10) does not have acidic groups, such as a carboxylic acid group, a phosphoric acid group, and a sulfonic acid group, in the molecule.

<As to Compound Represented by Formula (10A)>

A preferred example of the compound represented by Formula (10) is a compound represented by Formula (10A).

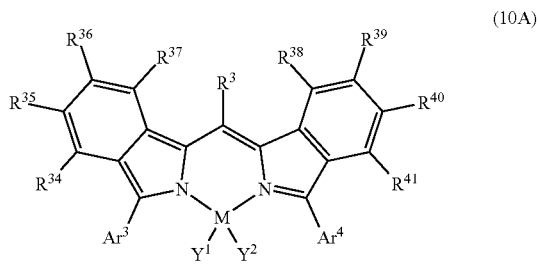

In Formula (10A), $Y^1$ to $Y^2$ each independently represent a halogen atom, an alkyl group, an aryl group, a heterocyclic group, a hydroxy group, an alkoxy group, an aryloxy group, an alkylthio group, or an arylthio group, an ethenyl group, or an ethynyl group, each of which may have a substituent. Examples of the substituent include the substituents described in the Substituent group A.

Preferably, $Y^1$ and $Y^2$ each independently represent halogen atoms.

Particularly preferably, $Y^1$ and $Y^2$ are fluorine atoms.

In Formula (10A), $R^3$ represents a hydrogen atom, an alkyl group, an aryl group, a heterocyclic group, an ethenyl group, an ethynyl group, or an acyl group, each of which may have a substituent.

Preferably, $R^3$ represents a hydrogen atom, an alkyl group, an aryl group, or a heterocyclic group, each of which may have a substituent.

More preferably, $R^3$ is a hydrogen atom.

In Formula (10A), $Ar^3$ and $Ar^4$ each independently represent an aryl group or a heterocyclic group, each of which may have a substituent. Examples of the substituent include the substituents described in the Substituent group A.

In Formula (10A), $R^{34}$ to $R^{41}$ each independently represent a hydrogen atom, a halogen atom, an alkyl group, an aryl group, a heterocyclic group, an ethenyl group, an ethynyl group, an acyl group, an alkoxy group, an aryloxy group, an alkylthio group, an arylthio group, or an amino group, each of which may have a substituent. Examples of the substituent include the substituents described in the Substituent group A.

In Formula (10A), at least one of $R^{34}$, ..., or $R^{41}$ is preferably an aryl group which may have a substituent.

More preferably, at least one of $R^{34}$, ..., or $R^{37}$ is an aryl group which may have a substituent, and at least one of $R^{38}$, ..., or $R^{41}$ is an aryl group which may have a substituent.

More preferably, at least one of $R^{34}$, ..., or $R^{41}$ is a group represented by Formula (11). Still more preferably, at least one of $R^{34}$, ..., or $R^{37}$ is a group represented by Formula (11), and at least one of $R^{38}$, ..., or $R^{41}$ is a group represented by Formula (11).

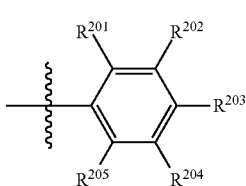

(11)

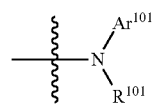

(12)

In Formula (11), $R^{201}$ to $R^{205}$ are each a hydrogen atom, a halogen atom, an alkyl group, an aryl group, a heterocyclic group, an ethenyl group, an ethynyl group, an acyl group, an alkoxy group, an aryloxy group, an alkylthio group, an arylthio group, or an amino group, and at least one of $R^{201}, \ldots,$ or $R^{205}$, is an atom or group other than a hydrogen atom. $R^{201}$ and $R^{202}$ may be linked to each other to form a ring, $R^{202}$ and $R^{203}$ may be linked to each other to form a ring, $R^{203}$ and $R^{204}$ may be linked to each other to form a ring, and $R^{204}$ and $R^{205}$ may be linked to each other to form a ring.

According to another preferred aspect, at least one of $R^{34}, \ldots,$ or $R^{41}$ is a group represented by Formula (12). Still more preferably, at least one of $R^{34}, \ldots,$ or $R^{37}$ is a group represented by Formula (12), and at least one of $R^{38}, \ldots,$ or $R^{41}$ is a group represented by Formula (12).

In Formula (12), $R^{101}$ represents a hydrogen atom, an alkyl group, an aryl group, a heterocyclic group, an ethenyl group, an ethynyl group, or an acyl group, each of which may have a substituent. Examples of the substituent include the substituents described in the Substituent group A. $Ar^{101}$ represents an aryl group or a heterocyclic group, each of which may have a substituent. Examples of the substituent include the substituents described in the Substituent group A. $Ar^{101}$ and $R^{101}$ may be linked to each other to form a ring.

It is preferable that the compound represented by Formula (10A) does not have acidic groups, such as a carboxylic acid group, a phosphoric acid group, and a sulfonic acid group, in the molecule.

<Specific Examples of Compound Represented by Formula (10) or Formula (10A)>

Specific examples of the compound represented by Formula (10) or Formula (10A) are shown below. Me represents a methyl group, Bu represents an n-butyl group, and Ph represents a phenyl group.

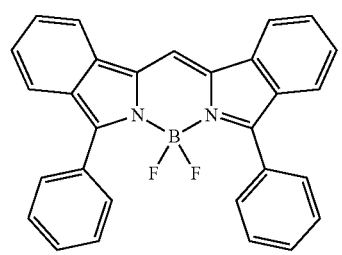

E-1

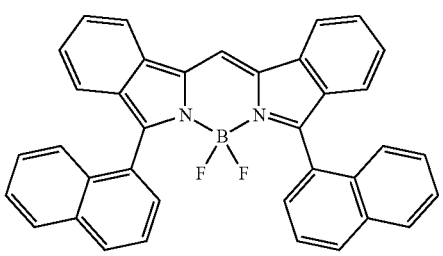

E-2

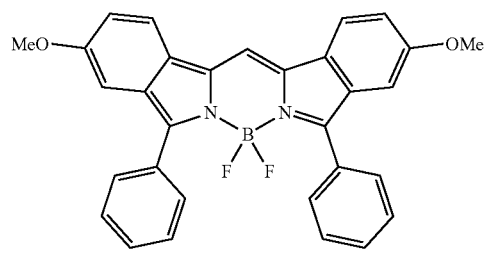

E-3

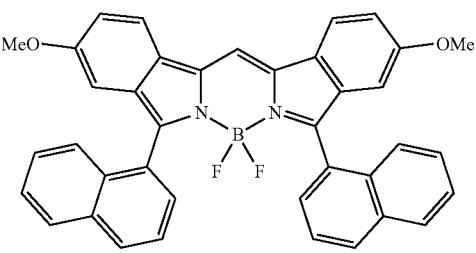

E-4

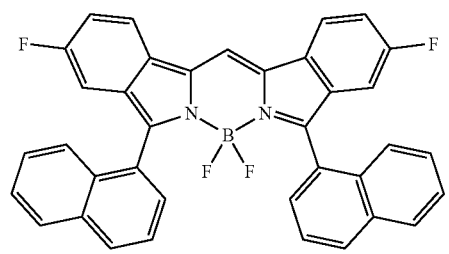

E-5

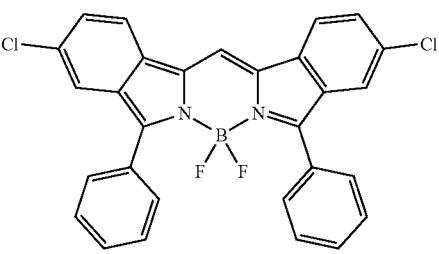

E-6

-continued
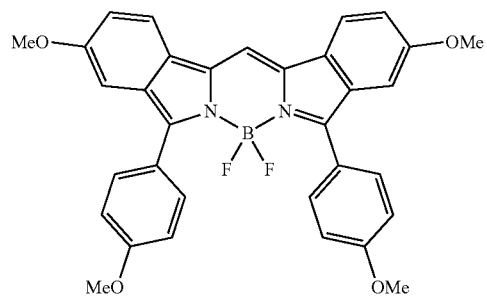
E-7
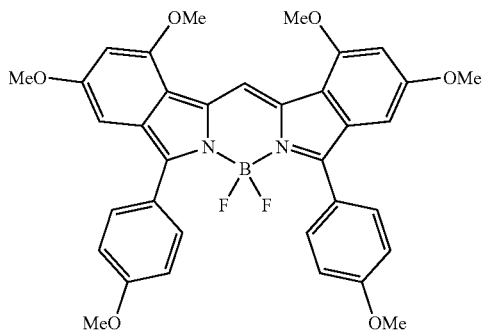
E-8
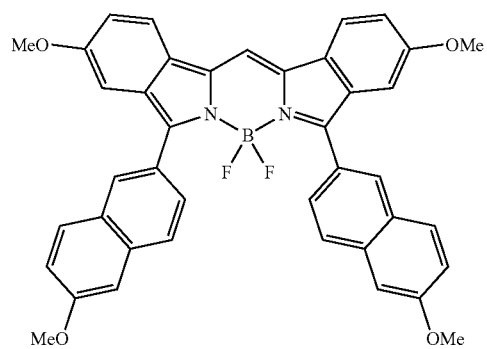
E-9
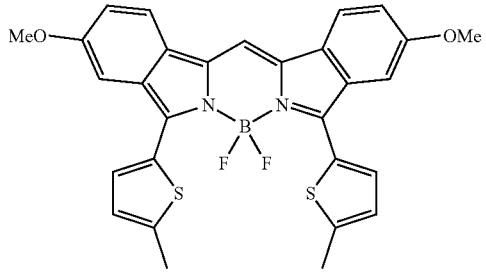
E-10
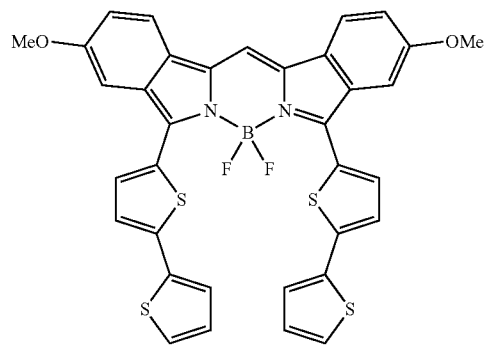
E-11
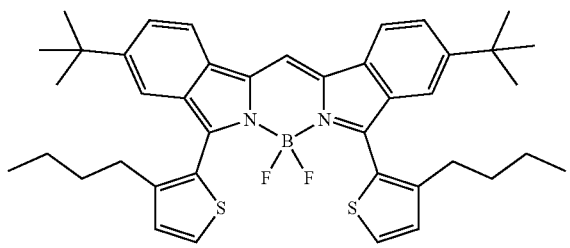
E-12
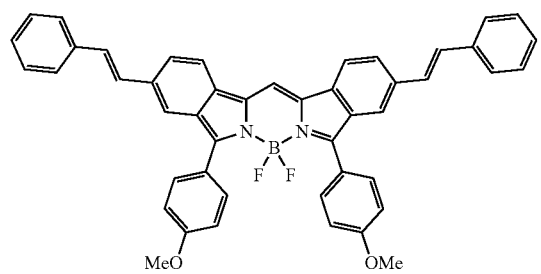
E-13
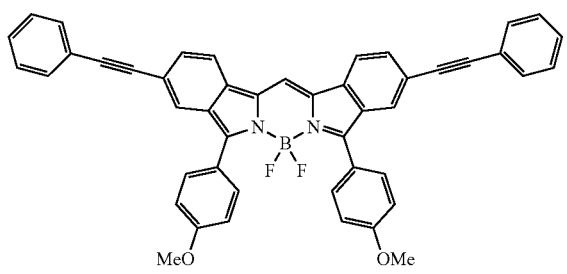
E-14
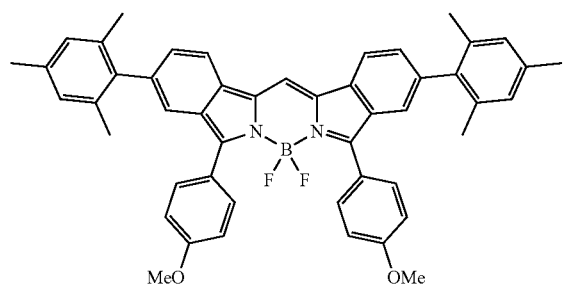
E-15
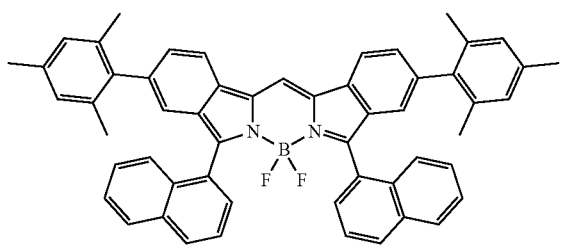
E-16

-continued
E-17
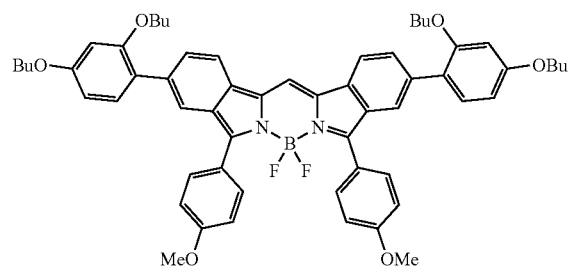
E-18
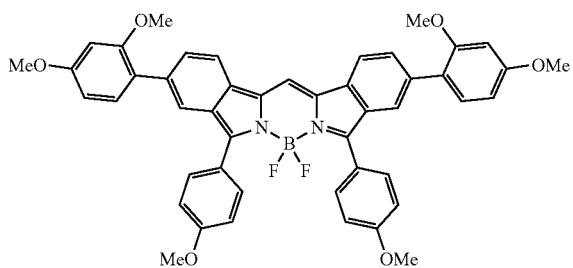
E-19
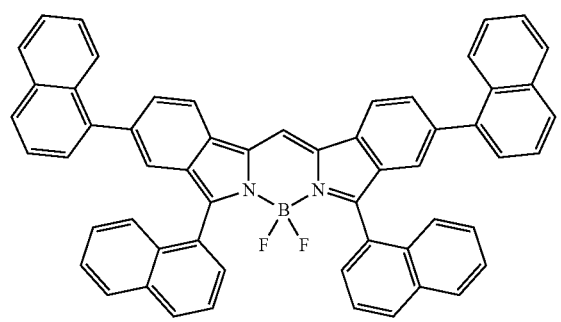
E-20
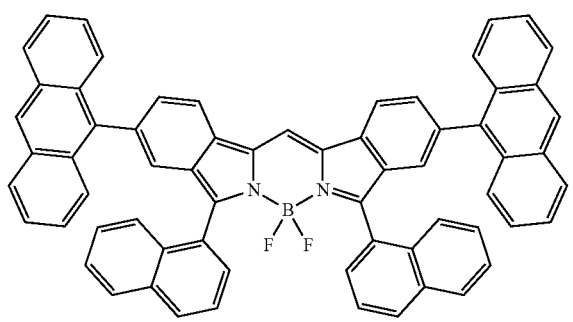
E-21
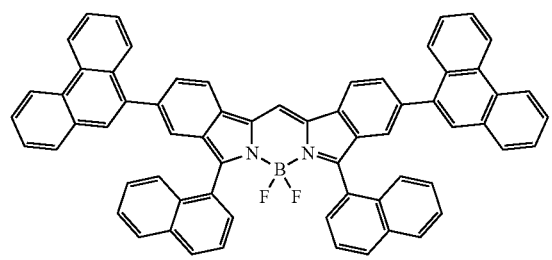
E-22
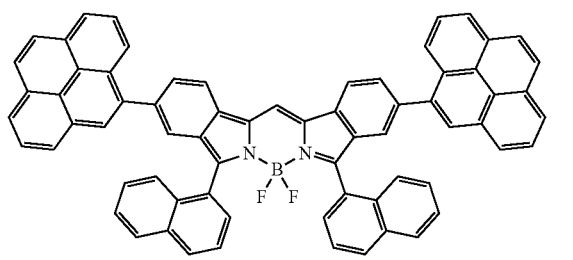
E-23
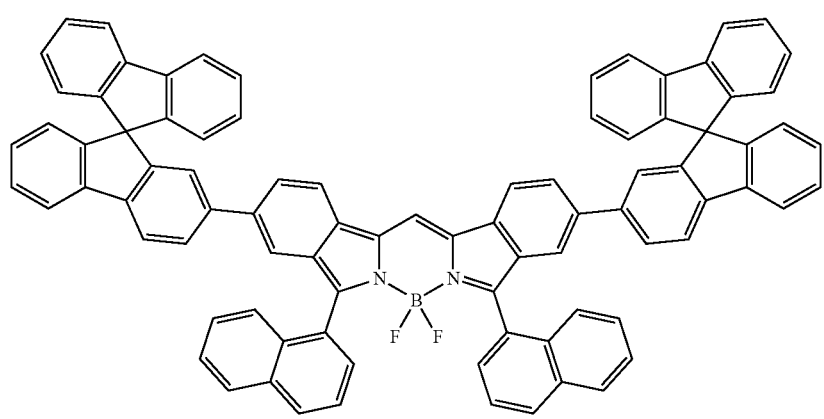

-continued
E-24
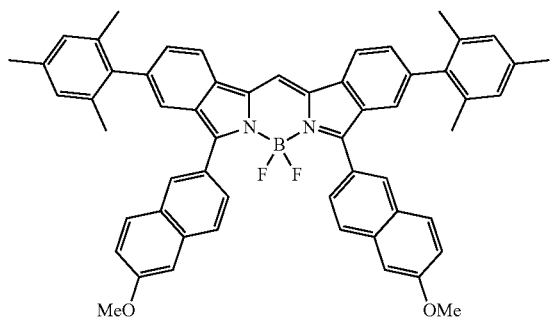
E-25
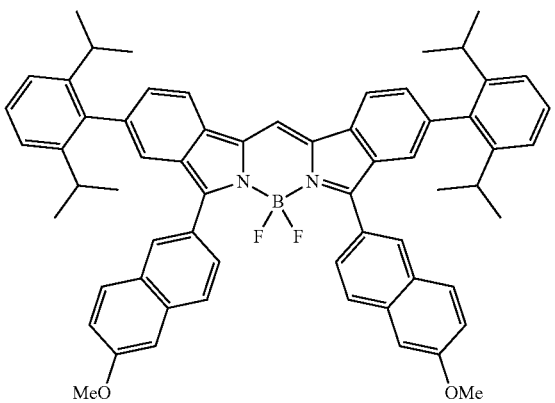
E-26
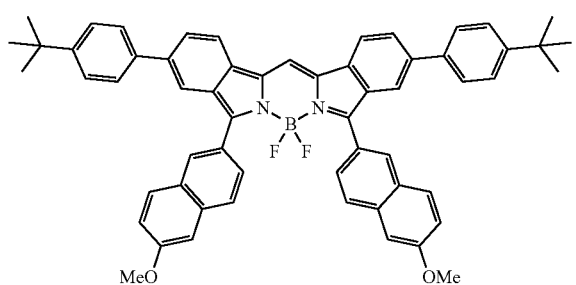
E-27
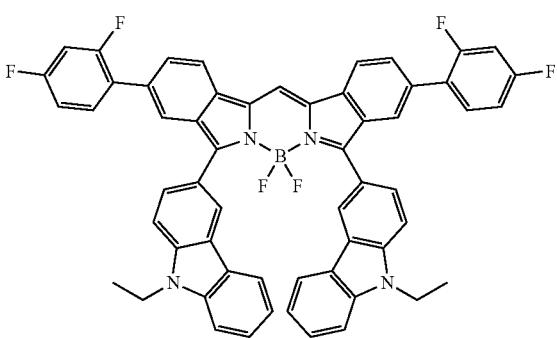
E-28
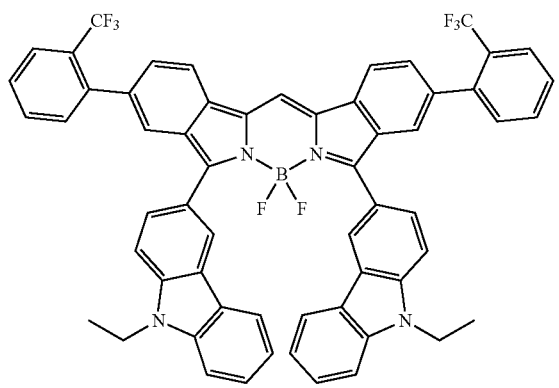
E-29
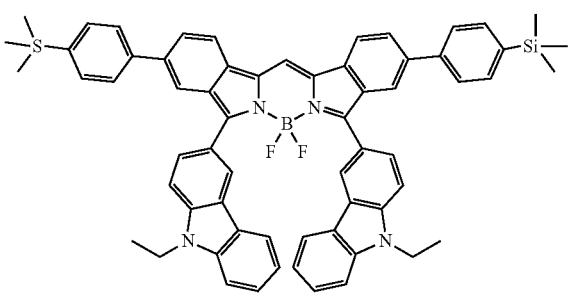
E-30
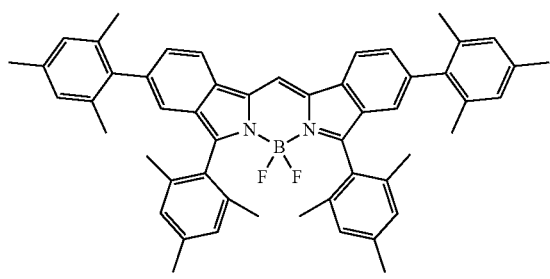
E-31
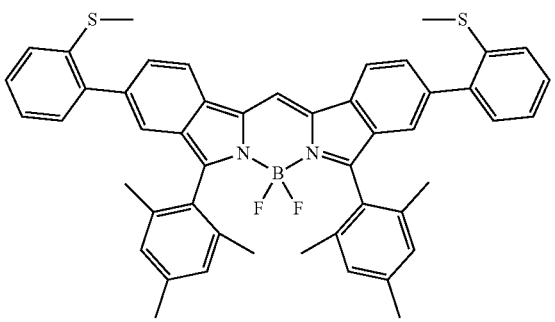

-continued
E-32
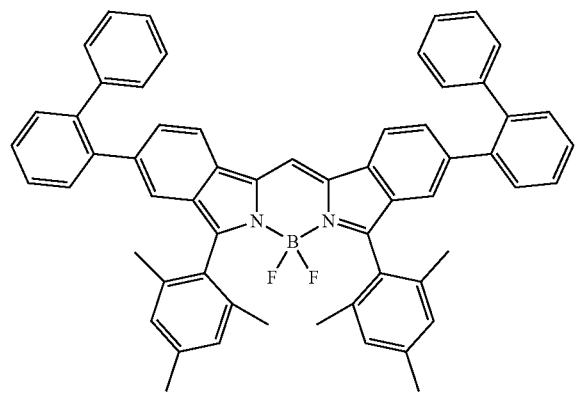
E-33
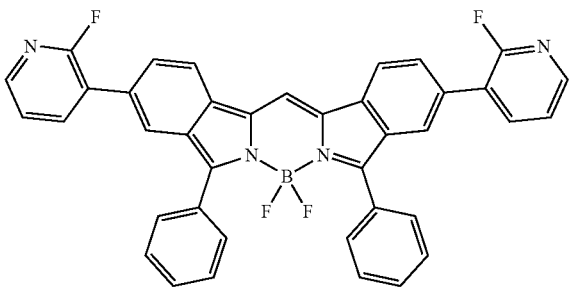
E-34
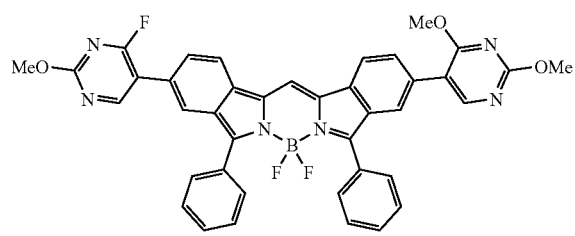
E-35
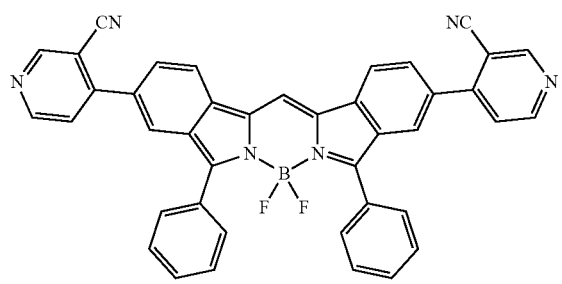
E-36
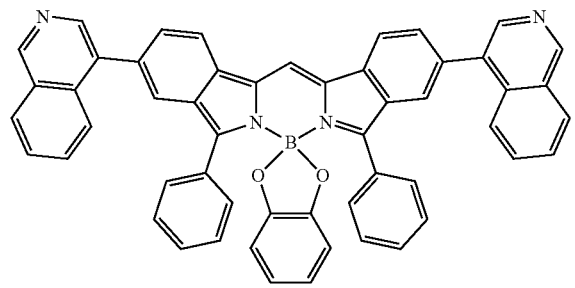
E-37
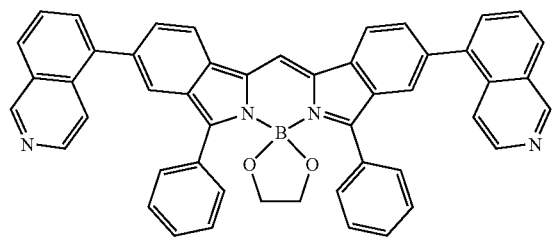
E-38
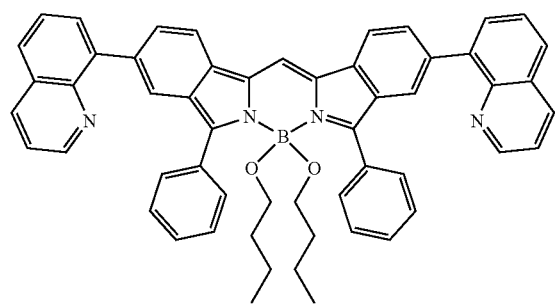
E-39
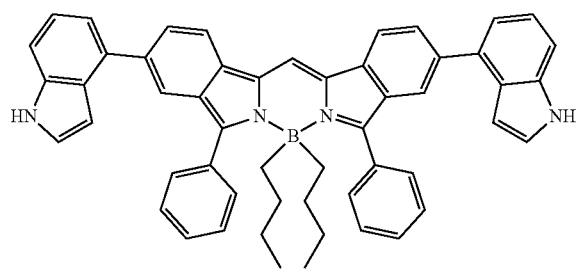
E-40
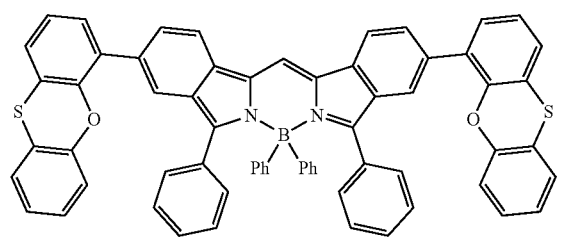
E-41
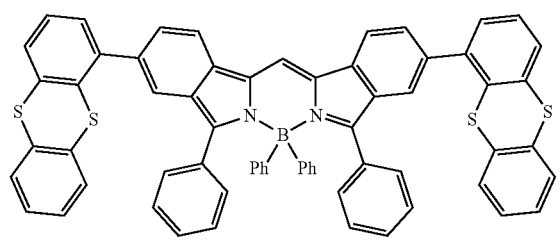

-continued
E-42
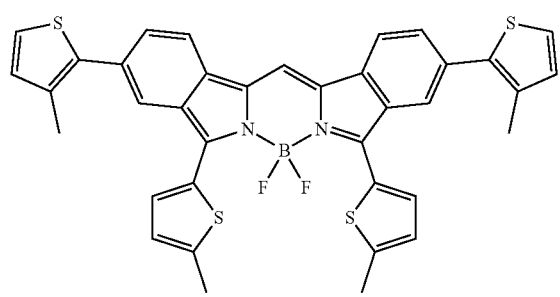
E-43
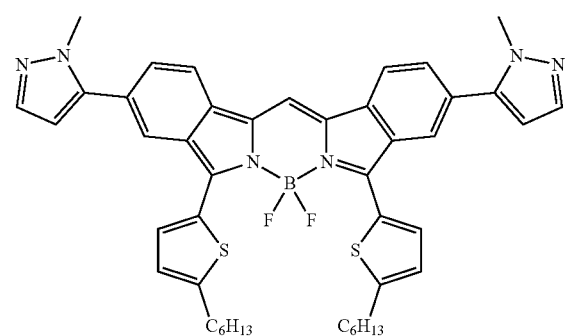
E-44
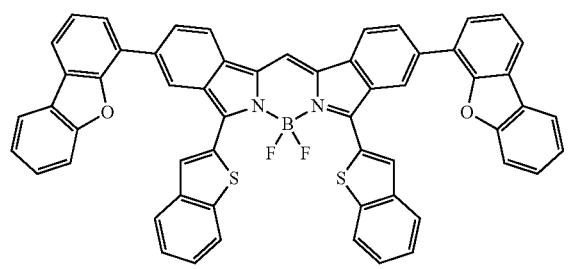
E-45
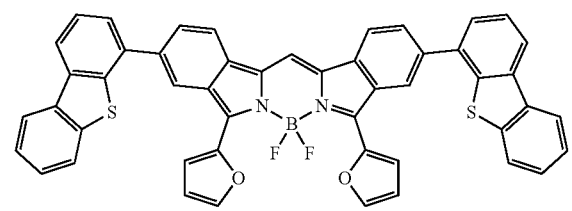
E-46
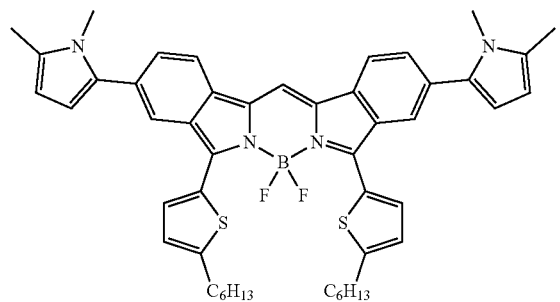
E-47
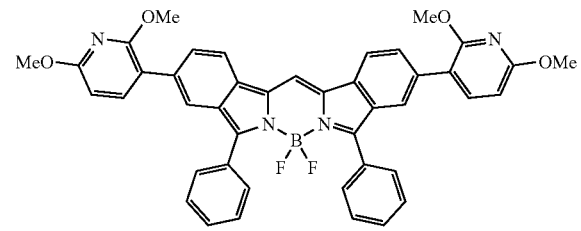
E-48
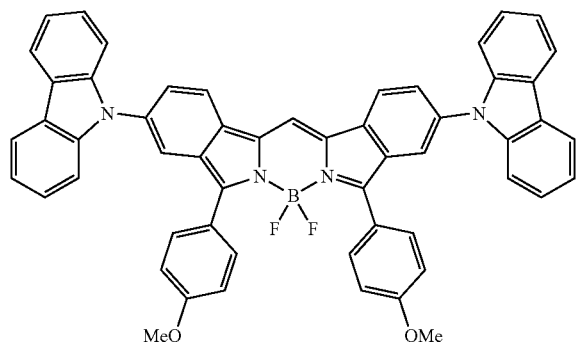
E-49
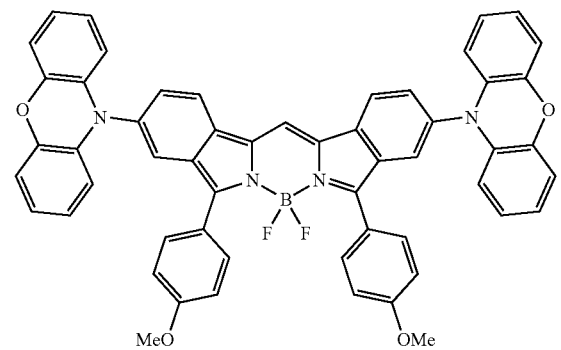

-continued
E-50
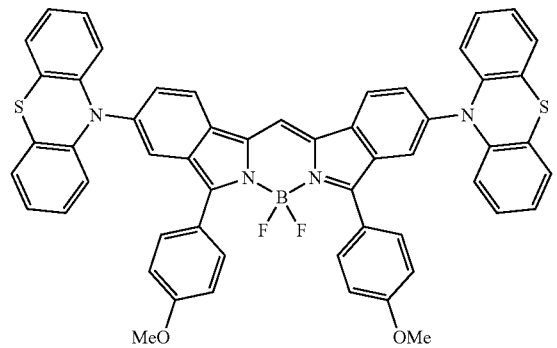
E-51
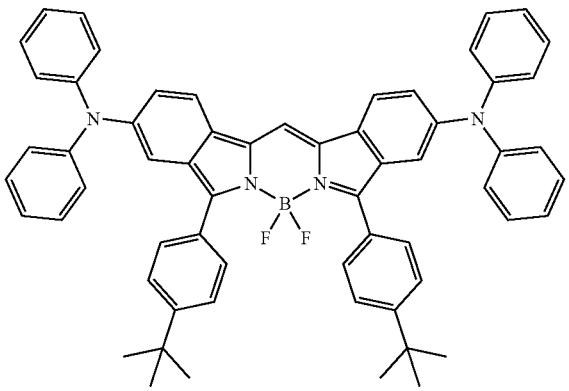
E-52
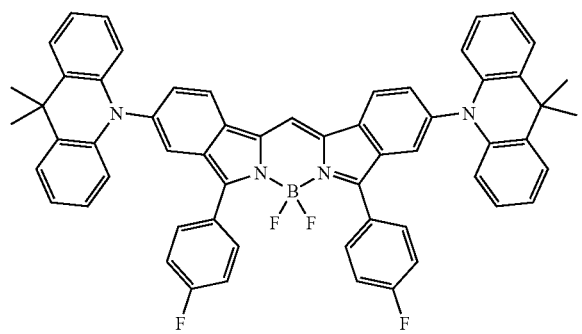
E-53
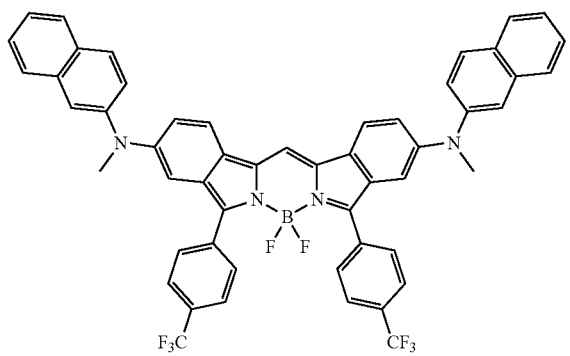
E-54
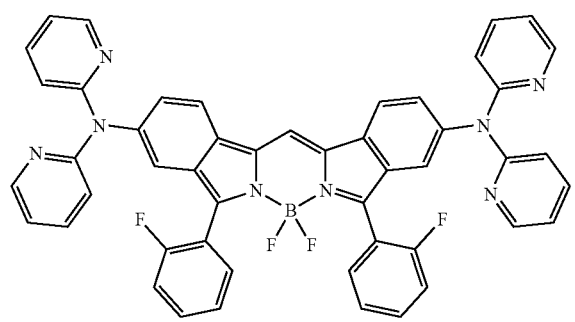
E-55
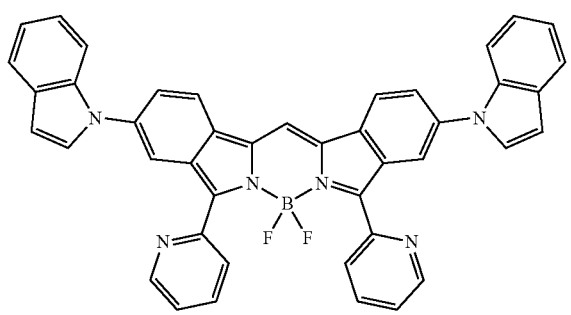
E-56
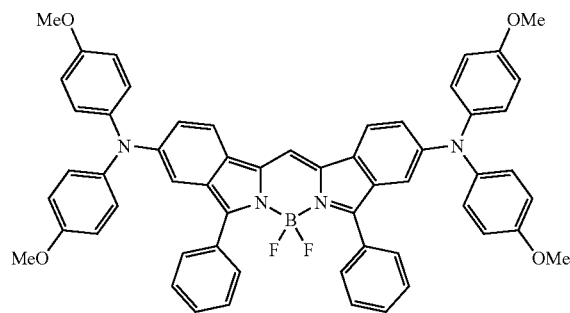
E-57
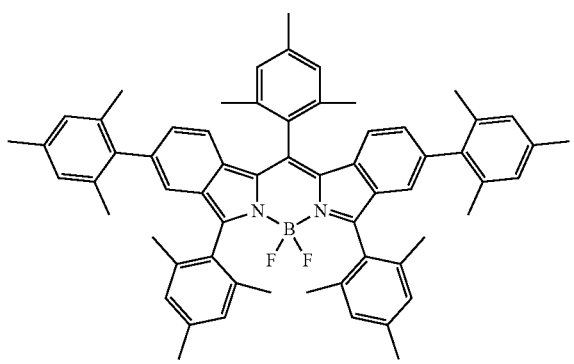

-continued
E-58
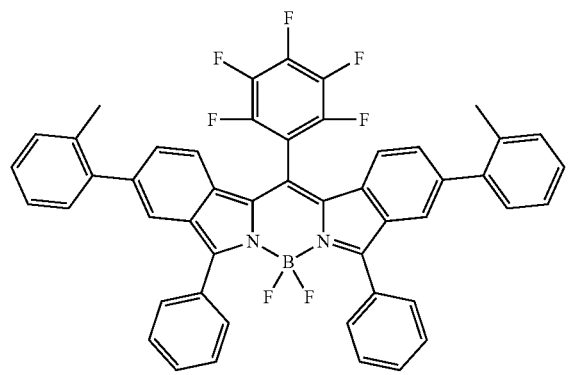
E-59
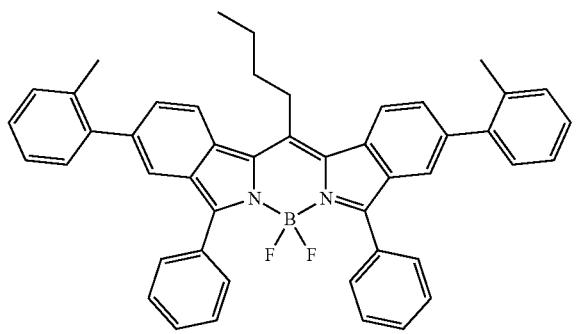
E-60
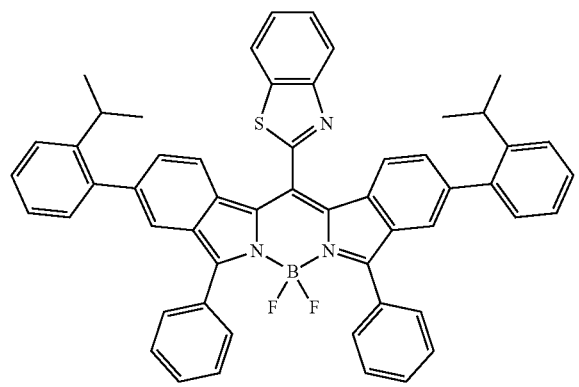
E-61
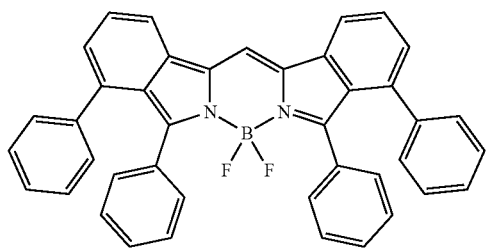
E-62
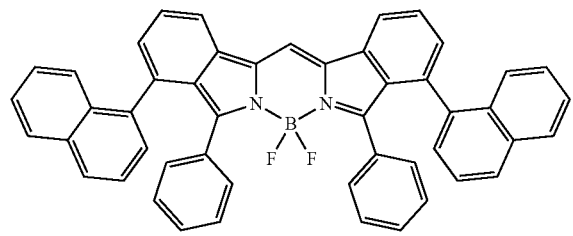
E-63
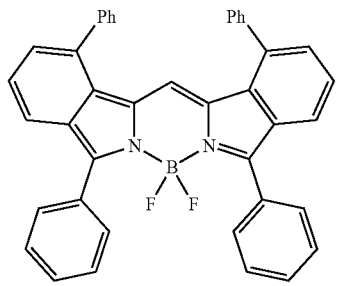
E-64
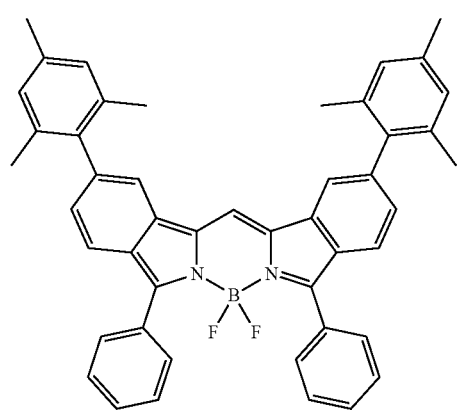
E-65
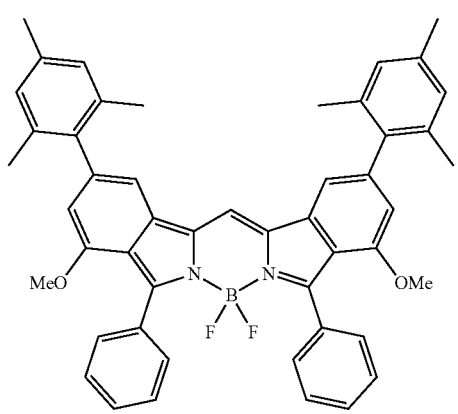

<As to Specific Examples of Combination of Energy Donor Compound and Energy Acceptor Compound>

Specific examples of a combination of an energy donor compound and an energy acceptor compound are shown below.

TABLE 1

| Donor | Acceptor |
|---|---|
| F-2 | F-43 |
| F-2 | F-44 |
| F-2 | F-46 |
| F-2 | F-51 |
| F-2 | F-55 |
| F-2 | F-69 |
| F-16 | F-38 |
| F-16 | F-39 |
| F-16 | F-41 |
| F-16 | F-42 |
| F-16 | F-43 |
| F-16 | F-45 |
| F-16 | F-46 |
| F-16 | F-48 |
| F-16 | F-49 |
| F-16 | F-50 |
| F-16 | F-51 |
| F-16 | F-52 |
| F-16 | F-53 |
| F-16 | F-54 |
| F-16 | F-55 |
| F-16 | F-56 |
| F-16 | F-57 |
| F-16 | F-58 |
| F-16 | F-59 |
| F-16 | F-60 |
| F-16 | F-61 |
| F-16 | F-62 |
| F-16 | F-63 |
| F-16 | F-64 |
| F-16 | F-69 |
| F-16 | F-70 |
| F-16 | F-71 |
| F-16 | F-72 |
| F-24 | F-43 |
| F-24 | F-44 |
| F-24 | F-46 |
| F-24 | F-51 |
| F-24 | F-55 |
| F-24 | F-69 |
| F-27 | F-43 |
| F-27 | F-44 |
| F-27 | F-46 |
| F-27 | F-51 |
| F-27 | F-55 |
| F-27 | F-69 |
| F-29 | F-43 |
| F-29 | F-44 |
| F-29 | F-46 |
| F-29 | F-51 |
| F-29 | F-55 |
| F-29 | F-69 |
| F-33 | F-43 |
| F-33 | F-44 |
| F-33 | F-46 |
| F-33 | F-51 |
| F-33 | F-55 |
| F-33 | F-69 |
| F-37 | F-43 |
| F-37 | F-44 |
| F-37 | F-46 |
| F-37 | F-51 |
| F-37 | F-55 |
| F-65 | F-43 |
| F-65 | F-44 |
| F-65 | F-46 |
| F-65 | F-51 |
| F-65 | F-55 |
| F-65 | F-69 |
| F-66 | F-43 |
| F-66 | F-44 |

TABLE 1-continued

| Donor | Acceptor |
|---|---|
| F-66 | F-46 |
| F-66 | F-51 |
| F-66 | F-55 |
| F-66 | F-69 |
| F-67 | F-43 |
| F-67 | F-44 |
| F-67 | F-46 |
| F-67 | F-51 |
| F-67 | F-55 |
| F-67 | F-69 |
| F-68 | F-43 |
| F-68 | F-44 |
| F-68 | F-46 |
| F-68 | F-51 |
| F-68 | F-55 |
| F-68 | F-69 |

TABLE 2

| Donor | Acceptor |
|---|---|
| E-4 | F-43 |
| E-4 | F-44 |
| E-4 | F-46 |
| E-4 | F-51 |
| E-4 | F-55 |
| E-4 | F-69 |
| E-16 | F-38 |
| E-16 | F-39 |
| E-16 | F-41 |
| E-16 | F-42 |
| E-16 | F-43 |
| E-16 | F-45 |
| E-16 | F-46 |
| E-16 | F-48 |
| E-16 | F-49 |
| E-16 | F-50 |
| E-16 | F-51 |
| E-16 | F-52 |
| E-16 | F-53 |
| E-16 | F-54 |
| E-16 | F-55 |
| E-16 | F-56 |
| E-16 | F-57 |
| E-16 | F-58 |
| E-16 | F-59 |
| E-16 | F-60 |
| E-16 | F-61 |
| E-16 | F-62 |
| E-16 | F-63 |
| E-16 | F-64 |
| E-16 | F-69 |
| E-16 | F-70 |
| E-16 | F-71 |
| E-16 | F-72 |
| E-20 | F-43 |
| E-20 | F-44 |
| E-20 | F-46 |
| E-20 | F-51 |
| E-20 | F-55 |
| E-20 | F-69 |
| E-57 | F-43 |
| E-57 | F-44 |
| E-57 | F-46 |
| E-57 | F-51 |
| E-57 | F-55 |
| E-57 | F-69 |
| F-1 | E-24 |
| F-2 | E-24 |
| F-3 | E-24 |

TABLE 2-continued

| Donor | Acceptor |
|---|---|
| F-4 | E-24 |
| F-5 | E-24 |
| F-6 | E-24 |
| F-7 | E-24 |
| F-8 | E-24 |
| F-12 | E-24 |
| F-13 | E-24 |
| F-14 | E-24 |
| F-15 | E-24 |
| F-16 | E-24 |
| F-19 | E-24 |
| F-20 | E-24 |
| F-21 | E-24 |
| F-23 | E-24 |
| F-24 | E-24 |
| F-25 | E-24 |
| F-26 | E-24 |
| F-27 | E-24 |
| F-28 | E-24 |
| F-29 | E-24 |
| F-30 | E-24 |
| F-31 | E-24 |
| F-32 | E-24 |
| F-33 | E-24 |
| F-34 | E-24 |
| F-36 | E-24 |
| F-37 | E-24 |
| F-65 | E-24 |
| F-66 | E-24 |
| F-67 | E-24 |
| F-68 | E-24 |
| F-2 | E-17 |
| F-16 | E-17 |
| F-33 | E-17 |
| F-65 | E-17 |
| F-66 | E-17 |
| F-67 | E-17 |
| F-68 | E-17 |

Regarding the selection of an energy donor compound and an energy acceptor compound, a compound with absorption in a short wavelength is the energy donor compound, a compound with absorption in a long wavelength is the energy acceptor compound, and in a case where the emission of the energy donor compound and the absorption of the energy acceptor compound overlap each other even a little, the compounds may be usable in the particle of the embodiment of the present invention. It is preferable that an absorption maximum wavelength of the energy acceptor compound is on the longer wavelength side by about 10 to 100 nm than an absorption wavelength of the energy donor compound. It is more preferable that an absorption maximum wavelength of the energy acceptor compound is on the longer wavelength side by about 10 to 70 nm than an absorption wavelength of the energy donor compound.

How longer the emission wavelength of the energy donor compound is than absorption wavelength (the size of the Stokes shift) varies depending on compounds, and thus it is difficult to be defined uniformly. However, since the compound represented by Formula (1) has maximum emission at a wavelength approximately 30 nm-longer than the absorption maximum wavelength, and has an emission spectrum in a range of a wavelength approximately 30 nm- to 100 nm-longer than the absorption maximum wavelength, it is assumed that an energy transfer system can be realized by combined use of an energy acceptor compound with absorption in the vicinity of the emission spectrum.

The absorption wavelength of each compound not only can be measured after synthesizing the compounds, but also can be predicted from calculation by Gaussian or the like.

In the present invention, the size of the Stokes shift is preferably 25 nm or more, more preferably 30 nm or more, still more preferably 35 nm or more, even more preferably 40 nm or more, even still more preferably 45 nm or more, particularly preferably 50 nm or more, and most preferably 60 nm or more. An upper limit of the size of the Stokes shift is not particularly limited but is generally 150 nm or less.

<Amount of Use of Compounds Represented by Formulae (1) to (6)>

There is no particular limitation on the content of the compound represented by Formulae (1) to (6) for the particles used in the present invention (that is, the particles before addition of the compound represented by Formulae (1) to (6)) as long as the effect of the present invention is not impaired, but the content is preferably 0.5 µmol/g to 400 µmol/g, more preferably 1 µmol/g to 300 µmol/g, still more preferably 2 µmol/g to 200 µmol/g, and particularly preferably 3 µmol/g to 100 µmol/g.

There is no particular limitation on the content of the compounds represented by Formulae (1) to (6) for the particles used in the present invention (that is, the particles before addition of the compounds represented by Formulae (1) to (6)) as long as the effect of the present invention is not impaired, but the content is preferably 0.1% by mass to 30% by mass, more preferably 0.2% by mass to 20% by mass, still more preferably 0.3% by mass to 10% by mass, and particularly preferably 0.4% by mass to 8% by mass.

In the luminescent particles of the present invention, at least one compound represented by Formulae (1) to (6) is used, but two or more compounds represented by Formulae (1) to (6) may be used. In a case where two or more kinds of compounds represented by Formulae (1) to (6) are used, it is preferable that the total amount of the compounds falls within the above range.

In a case of using the combination of the energy donor compound and the energy acceptor compound, the molar ratio of the energy donor compound to the energy acceptor compound is preferably 1:10 to 20:1, more preferably 1:10 to 10:1, and more preferably 1:5 to 10:1.

In a case where at least one kind of compound represented by Formula (1) is used as the energy donor compound and at least one kind of compound represented by Formula (1) is used as the energy acceptor compound, two or more kinds of compounds represented by Formula (1) may be used as the energy donor compound, and two or more kinds of compounds represented by Formula (1) may be used as the energy acceptor compound. In the above case, it is preferable that the total amount of the compounds represented by Formula (1) to be used falls within the above range.

<Method for Producing Compounds Represented by Formulae (1) to (6)>

The compounds represented by Formulae (1) to (6) can be produced, for example, according to a synthesis scheme shown in Examples which will be described later.

As an example, the synthesis of Compound (1) is outlined below. 3-ethyl-2,4-dimethylpyrrole and trifluoroacetic acid are added to a mixture of 3,5-bis(trifluoromethyl)benzaldehyde and dichloromethane while cooling with water, followed by stirring at room temperature, chloranil is added while cooling with water, followed by stirring at room temperature, boron trifluoride diethyl ether complex is added dropwise while cooling with water, followed by stirring at room temperature, and Compound (1-A) can be synthesized. Subsequently, Compound (1-A), 2,4,6-trimethylbenzaldehyde, and dehydrated toluene are mixed and stirred at room temperature. Piperidine and one piece of p-toluenesulfonic acid monohydrate are added, and the mixture is stirred while distilling off the solvent.

As another example, Compound (5) can be produced through Compound (5-A), Compound (5-B), and Compound (5-C) from 2,3,5,6-tetrafluorobenzaldehyde and 2,4-dimethylpyrrole as starting compounds according to the synthesis scheme in Examples which will be described later.

Compound (1) and Compound (5) are within the definition of the compound represented by Formula (1). The compound represented by Formula (1) other than Compound (1) and Compound (5) can also be produced by substituting the compound used in the reaction with a compound having a substituent corresponding to a desired target compound represented by Formula (1).

<Method for Producing Compound Represented by Formula (10)>

The compound represented by Formula (10) can be produced, for example, according to the following synthesis scheme.

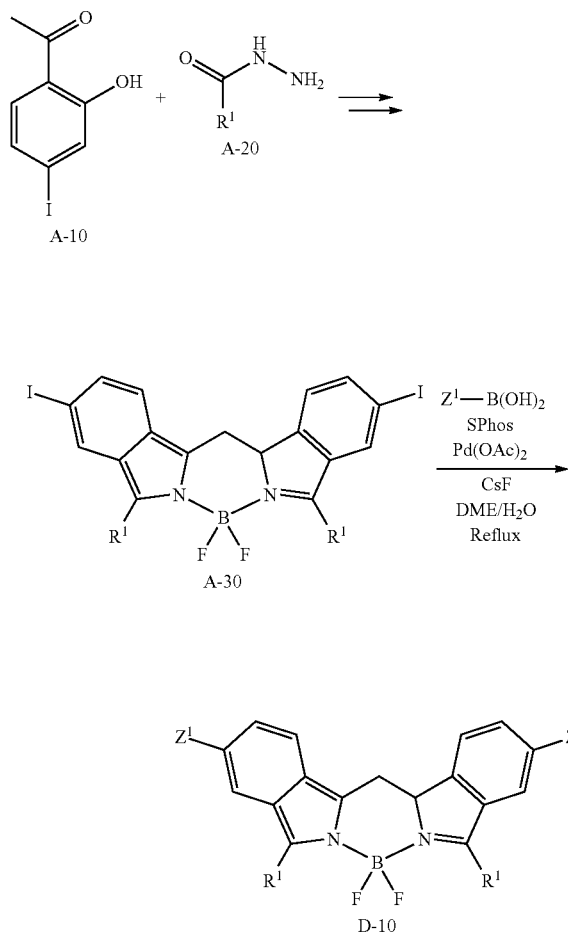

The definitions of $R^1$ and $Z^1$ in the above synthesis scheme are the same as the definitions of $R^1$ and $Z^1$ in formula (10).

Compound A-30 can be synthesized by reacting Compound A-10 with Compound A-20 according to the method described in Macromolecules 2010, 43, 193 to 200. Then, Compound A-30, a compound represented by a formula of $Z^1$—$B(OH)_2$, and cesium fluoride (CsF) are added to a mixed solution of dimethoxyethane (DME) and water, and vacuum drawing and nitrogen substitution are repeated for degassing. Compound D-10 can be produced by adding palladium acetate ($Pd(OAc)_2$) and 2-dicyclohexylphosphino-2',6'-dimethoxybiphenyl (SPhos) thereto, raising the temperature, and performing the reaction under reflux for a predetermined time (for example, 2 to 24 hours).

Compound D-10 is within the definition of the compound represented by Formula (10). The compound represented by Formula (10) other than Compound D-10 can also be produced by substituting any one or more of Compound A-10, Compound A-20, or the compound represented by a formula of $Z^1$—$B(OH)_2$ with corresponding compounds.

(First Particle Having Label)

The first particle having a label in the present invention exhibits high quantum yield and high luminance by including the compound represented by Formula (1).

An excitation maximum wavelength of the particle having a label is a wavelength with the largest fluorescence intensity in the excitation spectrum. An fluorescence maximum wavelength of the particle having a label is a wavelength with the largest fluorescence intensity in the fluorescence spectrum. In addition, the excitation spectrum exhibits the excitation wavelength dependency of the fluorescence label intensity, and the fluorescence spectrum exhibits the fluorescence wavelength dependency of the fluorescence intensity.

The excitation maximum wavelength of the particle having a label is preferably 640 nm to 900 nm, more preferably 640 nm to 800 nm, and still more preferably 650 nm to 750 nm.

The fluorescence maximum wavelength of the particle having a label is preferably 660 nm to 900 nm, more preferably 660 nm to 800 nm, and still more preferably 670 nm to 750 nm.

The fluorescence intensity of the particle having a label is fluorescence intensity in a case of being measured under a certain measurement condition, and since the fluorescence intensity depends on the measurement condition, the fluorescence intensity is generally used to make a relative comparison.

The excitation maximum wavelength, fluorescence maximum wavelength, and fluorescence intensity of the particle having a label can be measured using a commercially available fluorescence spectrophotometer, and for example, can be measured using a fluorescence spectrophotometer RF-5300PC manufactured by Shimadzu Corporation.

The quantum yield of the particle having a label is the ratio of the number of photons emitted as fluorescence to the number of photons absorbed by the particle having a label.

The quantum yield of the particle having a label is preferably 0.25 or more, more preferably 0.30 or more, and still more preferably 0.40 or more. An upper limit of the quantum yield is not particularly limited but generally is 1.0 or less.

The quantum yield of the particle having a label can be measured using a commercially available quantum yield measuring apparatus, and for example, can be measured using an absolute PL quantum yield spectrometer C9920-02 manufactured by Hamamatsu Photonics K.K.

(Method for Producing First Particle Having Label)

A method for producing the particle having a label is not particularly limited, but the particles having a label can be produced by mixing particles with at least one kind of compound represented by Formula (1). For example, the particles having a label can be prepared by adding the compound represented by Formula (1) to particles such as latex particles. More specifically, the particles having a label can be produced by adding a solution containing the compound represented by Formula (1) to a solution of particles containing at least one of water or a water-soluble organic solvent (tetrahydrofuran, methanol, or the like) and stirring the mixture.

In the present invention, a dispersion liquid containing the above-described particles having a label may be prepared.

The dispersion liquid can be produced by dispersing the particles having a label, in a dispersion medium. Examples of the dispersion medium include water, an organic solvent, and a mixture of water and an organic solvent. An alcohol such as methanol, ethanol, or isopropanol, an ether-based solvent such as tetrahydrofuran, or the like can be used as the organic solvent.

The concentration of the solid content of the particles having a label, in the dispersion liquid, is not particularly limited, but is generally 0.1% to 20% by mass, preferably 0.5% to 10% by mass, and more preferably 1% to 5% by mass.

(Modification of Particle Having a Label by First Binding Substance)

The method for immobilizing the first binding substance on the particle having a label is described, for example, in JP2000-206115A or the protocol attached to FluoSpheres (registered trademark) polystyrene microsphere F8813 of Thermo Fisher Scientific Inc., and any known method for preparing a reagent for an immunoagglutination reaction can be used. In addition, as a principle of immobilizing an antibody as a binding substance on particles, any principle of physical adsorption or a chemical bond by a covalent bond can be adopted. As a blocking agent (that is, the first blocking agent) covering a particle surface which is not coated with the antibody after immobilizing the antibody on the particle, for example, albumin (such as BSA), skim milk, casein, a soybean-derived component, a fish-derived component, polyethylene glycol, or the like, and commercially available blocking agents for an immune reaction or the like containing the substances as well as substances having the same property as that of the substances can be used. These blocking agents can be subjected to pretreatment such as partial modification with heat, acid, alkali, or the like, as necessary. Furthermore, as the first blocking agent, an antibody (globulin) which is incapable of binding to progesterone or a protein (Protein A and Protein G) which is not used in a test area can be used.

A specific method for immobilizing an antibody on particles is exemplified below. An antibody solution of which concentration is adjusted to 0.01 to 20 mg/mL is added to a liquid in which the particles are dispersed such that the concentration of the solid content of the particles becomes 0.1% to 10% by mass, and mixing is performed. Stirring is continued for 5 minutes to 48 hours under a condition of a temperature of 4° C. to 50° C. Next, the particle and the solution are separated by centrifugation or other methods to sufficiently remove antibodies not bound to the particle contained in the solution. Then, an operation of washing the particle with a buffer solution is repeated 0 to 10 times. It is preferable that after carrying out an operation of mixing the particle and the antibody and binding the antibody to the particle, a portion of the particle surface to which the antibody is not bound is protected using a blocking agent such as the components which do not participate in the antigen-antibody reaction, preferably protein, and more preferably globulin, albumin, BLOCKACE (registered trademark), skim milk, and casein.

In a case where the antigen, the antibody, or the like is immobilized on the particle, a stabilizer can be added, as necessary. The stabilizer is not particularly limited as long as the stabilizer stabilizes an antigen or an antibody, like a synthetic polymer or a natural polymer, such as polysaccharides or sucrose, and commercially available stabilizers such as Immunoassay Stabilizer (Advanced Biotechnologies Inc.) can also be used.

The particle having a label and modified with the first binding substance is contained in the kit according to the embodiment of the present invention, and an aspect in which the labeled particle is contained in a container, for example, a cup, which is a part of the kit is preferable. In this case, progesterone in the biological sample can be bound to the first binding substance by injecting the biological sample that includes progesterone into a container that contains the particle having a label, and by mixing and stirring components.

(Second Binding Substance)

A second particle having no label in the present invention is modified with a second binding substance incapable of specifically binding to progesterone. As the second binding substance, for example, there is no particular limitation as long as the substance is a compound incapable of specifically binding to progesterone, such as a binding substance (antibody) or a protein (Protein A or Protein G) which binds to the binding substance (antibody), and not having an affinity for a first binding substance, and any compound can be preferably used. In a case where the second binding substance is an antibody, an antiserum prepared from a serum of an immunized animal, an immunoglobulin fraction purified from the antiserum, a monoclonal antibody obtained by cell fusion using spleen cells of an immunized animal, or a fragment thereof [for example, F(ab')$_2$, Fab, Fab', or Fv] can be used. Preparation of these antibodies can be performed by a conventional method. Furthermore, the antibody may be modified as in the case of a chimeric antibody or the like, or a commercially available antibody or an antibody prepared from an animal serum or culture supernatant by known methods can be used.

The method for immobilizing the second binding substance such as an antibody on the particle is described, for example, in JP2000-206115A or the protocol attached to FluoSpheres (registered trademark) polystyrene microsphere F8813 of Molecular Probes Inc., and any known method for preparing a reagent for an immunoagglutination reaction can be used. In addition, as a principle of immobilizing an antibody as a binding substance on particles, any principle of physical adsorption or a chemical bond by a covalent bond can be adopted. As a blocking agent covering a particle surface which is not coated with the antibody after immobilizing the antibody on the particle, known substances, for example, BSA, skim milk, casein, a soybean-derived component, a fish-derived component, polyethylene glycol, or the like, and commercially available blocking agents for an immune reaction or the like containing the substances as well as substances having the same property as that of the substances can be used. These blocking agents can be subjected to pretreatment such as partial modification with heat, acid, alkali, or the like, as necessary.

(First Particle and Second Particle)

As for a usage ratio of a second particle to a first particle, a mass ratio of the second particle to the first particle is generally 1 to 20, preferably 1 to 10, more preferably 2 to 8, and still more preferably 4 to 6.

In the present invention, an average particle diameter of the first particles is 50 to 250 nm, an average particle diameter of the second particles is 70 to 500 nm, and the average particle diameter of the second particles is larger than the average particle diameter of the first particles.

The average particle diameter of the first particles is preferably 70 to 130 nm, more preferably 80 to 120 nm, and still more preferably 85 to 110 nm.

The average particle diameter of the second particles is preferably 130 to 300 nm, more preferably 135 to 260 nm, and still more preferably 140 to 200 nm.

As a method for measuring the average particle diameter, optical microscopy, confocal laser microscopy, electron microscopy, atomic force microscopy, static light scattering method, laser diffraction method, dynamic light scattering method, centrifugal sedimentation method, electric pulse measurement method, chromatography method, ultrasonic attenuation method, and the like are known, and apparatuses corresponding to the respective principles are commercially available. Among these measurement methods, it is preferred to measure the average particle diameter of the fluorescent particles using a dynamic light scattering method from the viewpoint of the particle diameter range and ease of measurement. Examples of commercially available measuring apparatuses using dynamic light scattering include NANOTRAC UPA (Nikkiso Co., Ltd.), dynamic light-scattering particle size analyzer LB-550 (HORIBA, Ltd.), fiber-optics particle analyzer FPAR-1000 (Otsuka Electronics Co., Ltd.), and the like. In the present invention, the average particle diameter is obtained as a median diameter (d=50) measured at 25° C. under the conditions of a viscosity of 0.8872 cP (here, 1 Pa·s=1,000 cP) and a refractive index of water of 1.330.

The first particle (particle having a label) and the second particle used in the present invention may be stored in a dry state and may be used by mixing with a biological sample containing progesterone at the time of measurement. In a case where the first particles and the second particles are stored in a solution state, the particles may become larger due to aggregation or fusion between the particles, and the measurement precision may change. Particles stored in a dry state are also referred to as dry particles. Dry particles refer to particles in a state where an amount of moisture contained is removed until a mass of the moisture (water content) to a mass of a solid content of particles which contain a labeled substance not containing moisture is preferably 30% by mass or less, more preferably 25% by mass or less, and still more preferably 20% by mass or less. Means for performing drying is not particularly limited and known drying means, for example, a drying method using a dehumidifying agent, a reduced-pressure drying method, a freeze-drying method, or the like can be used. In the present invention, the first particles and the second particles may be separately dried to obtain dry particles or may be mixed in a desired mass ratio in a solution state and then dried to obtain dry particles.

(Flow Channel)

The kit of the embodiment of the present invention includes a flow channel for flowing first particles and second particles. In the present invention, a liquid mixture obtained by mixing a biological sample that may contain progesterone, the first particle having a label, and the second particle is applied onto a substrate and developed into a flow channel. The flow channel is not particularly limited as long as the flow channel is a passage that allows the biological sample, the first particle having a label, and the second particle to flow down to the reaction site. A preferred aspect of the flow channel is a flow channel having a structure in which a spotting port for spotting a biological sample liquid containing the first particles having a label and the second particles, a metal thin film as a reaction site on which a third binding substance is immobilized, and a flow channel beyond the metal thin film are provided and the biological sample can pass over the metal thin film. Preferably, a suction port can be provided on a side opposite to the spotting port with respect to the metal thin film.

(Substrate)

In the present invention, in order to achieve high-sensitive measurement, it is preferable to adopt a measurement method for performing surface plasmon fluorescence (SPF) detection described later. As a substrate in this case, it is preferable to use a substrate having a metal film on a surface. A metal constituting the metal film is not particularly limited as long as the metal can cause surface plasmon resonance. Preferably, free-electron metals such as gold, silver, copper, aluminum, or platinum can be mentioned, and gold is particularly preferable. In a case where gold is used, the detection area described later is on the gold film. The metals can be used alone or in a combination thereof. Further, in consideration of the adhesiveness to the substrate, an intervening layer including chromium or the like may be provided between the substrate and the layer including metal. The thickness of the metal film is randomly determined, but for example, is preferably 1 nm or more and 500 nm or less, and particularly preferably 10 nm or more and 200 nm or less. In a case where the thickness exceeds 500 nm, a surface plasmon phenomenon of a medium cannot be detected sufficiently. Moreover, in a case of providing an intervening layer which includes chromium or the like, it is preferable that thickness of the intervening layer is 0.1 nm or more and 10 nm or less.

The formation of the metal film may be carried out by a conventional method, and can be carried out, for example, by a sputtering method, a vapor deposition method, an ion plating method, an electroplating method, a non-electrolytic plating method, or the like. In this case, the thickness of the mixed layer of the substrate material and the metal film is not particularly limited as long as sufficient adhesiveness can be ensured, and 10 nm or less is preferable.

The metal film is preferably disposed on the substrate. Herein, "disposed on the substrate" includes a case where the metal film is disposed to be in direct contact with the substrate, and a case where the metal film is disposed not in direct contact with the substrate but in contact with the substrate through other layers. The material of the substrate that can be used in the present invention is, for example, optical glass such as BK7 (borosilicate glass), which is a type of general optical glass, or synthetic resin, specifically a substance formed of a material transparent to laser light, such as polymethyl methacrylate, polyethylene terephthalate, polycarbonate, or a cycloolefin polymer can be used. Such a material of the substrate is preferably a material that does not exhibit anisotropy with respect to polarization and has excellent processability.

As a preferred aspect of the substrate for SPF detection, a substrate in which a gold film is formed on polymethyl methacrylate (PMMA) by a sputtering method or the like can be mentioned.

The substrate includes a detection area having a substance capable of binding to the first binding substance.

A method for immobilizing a substance capable of binding to the first binding substance on a substrate is described in, for example, Tech Notes Vols. 2 to 12 provided by Nunc Corporation and all known methods for preparing a general Enzyme-linked immunosorbent assay (ELISA) reagent can be used. The surface may be modified by disposing a self-assembled monolayer (SAM) on the substrate. In addition, as a principle of immobilizing a substance capable of binding to the first binding substance, on the substrate, any principle of physical adsorption or a chemical bond by a covalent bond can be adopted. As a blocking agent covering a substrate surface which is not coated with a substance capable of binding to the first binding substance after immobilizing, on the substrate, a substance capable of binding to the first binding substance, known substances, for example, BSA, skim milk, casein, a soybean-derived component, a fish-derived component, polyethylene glycol, or the like, and commercially available blocking agents for an immune reaction or the like containing the substances as well as substances having the same property as that of the substances can be used. These blocking agents can be subjected to pretreatment such as partial modification with heat, acid, alkali, or the like, as necessary.

(Detection Area<Test Area>)

In the present invention, a test area can be provided on the substrate to detect the presence or absence of progesterone in the biological sample. In the test area, the antigen can be quantified by a method in which only the labels bound to the antigen is caused not to be bound, only labels not bound to the antigen is captured, and the amount of labels bound to the antigen is calculated. This detection method is referred to as a competition method and herein, the substrate related to the competition method will be described.

It is preferable that the test area of the substrate has a site for reacting with the binding substance (for example, antibody) present on the labeled particle. As a preferred aspect of the present invention, an aspect in which progesterone present in the biological sample is on the test area of the substrate is preferable. In this case, progesterone and BSA are reacted in the presence of a condensing agent to prepare an progesterone-BSA conjugate, and a test area can be prepared by adsorbing the conjugate onto the test area. The progesterone-BSA conjugate which is the measurement target substance can be bound to the test area on a substrate by a method in which the conjugate is dissolved in a buffer solution, and the resultant is spotted on the substrate and left to stand for a predetermined time, the supernatant is sucked, and drying is performed.

(Reference Area<Control Area>)

In the present invention, in order to minimize influence of the measurement environment, particularly the measurement temperature, as much as possible, a control area is provided on the substrate, and the information on the test area is standardized by the information on the control area, thereby enabling the environmental dependency to be suppressed extremely low. The control area is preferably designed to be capable of binding to all the labels regardless of the amount of progesterone present in the biological sample to be used. It is preferable to provide an antibody that interacts with all the antibodies present on the labeled particle. By designing in this manner to standardize the information on the test area by the information on the control area, for example, even in a case where the flow of the biological sample or the reaction rate is affected in the low temperature environment, such influence can be cancelled by the standardization, and thus it becomes possible to obtain a result that is always precise and not affected by the measurement environment.

An antibody present in the control area preferably has a function of recognizing a binding substance (for example, antibody) present on the labeled particle, in a case where the antibody is derived from a mouse, an anti-mouse antibody is preferable, and in a case where the antibody on the labeled particle is derived from a goat, an anti-goat antibody is preferable. These antibodies on the control area can be bound to a substrate by a method in which the antibodies are dissolved in a buffer solution, and the resultant is spotted on the substrate and left to stand for a predetermined time, the supernatant is sucked, and drying is performed.

(Blocking Agent)

For example, in a case of a competition method, not only a negative biological sample which does not contain progesterone but also a biological sample which becomes negative by reacting to even a positive biological sample which contains progesterone are present, and the solution to the problem of deviation at a high value is recognized as an issue. The causes of the false negative are not clear, but one of the causes is considered to be that labeled particles which are originally not desired to bind to the detection area but which bind to the detection area are present due to nonspecific interaction between the labeled particle surface not covered with the antibody and the detection area (test area). Moreover, in a case where the same substance as the substance present on the test area is present on the surface of the labeled particle, and a free antibody or the like is present in the biological sample, even in the measurement of a positive biological sample containing progesterone, the positive biological sample may be detected as negative by binding of the antibody to both of the substance present on the test area and the substance on the surface of the labeled particle. In general, blocking with BSA is used to suppress nonspecific adsorption onto a solid phase surface (for example, a labeled particle surface, and a gold film surface of a substrate).

(Antibody)

In the present invention, antibodies can be used regardless of animal species or subclasses thereof. For example, an antibody that can be used in the present invention is an antibody derived from an organism in which an immune reaction can occur, such as mice, rats, hamsters, goats, rabbits, sheep, cows, or chickens, specific examples thereof include mouse IgG, mouse IgM, rat IgG, rat IgM, hamster IgG, hamster IgM, rabbit IgG, rabbit IgM, goat IgG, goat IgM, sheep IgG, sheep IgM, bovine IgG, bovine IgM, chicken IgY, and the like, and either polyclonal or monoclonal antibody can be used. A fragmented antibody is a molecule derived from a complete antibody, having at least one antigen binding site, and is specifically $F(ab')_2$, Fab, Fab', or the like. These fragmented antibodies are molecules obtained by an enzyme or chemical treatment or by using genetic engineering techniques.

(Other Elements of Kit)

The kit of the embodiment of the present invention is used for a method for measuring progesterone. The kit of the embodiment of the present invention includes a first particle having a label and a second particle having no label, and further includes a flow channel for flowing the first particle and the second particle and a substrate having a substance capable of binding to the first binding substance. The kit of the embodiment of the present invention may further include various instruments or devices used for measuring progesterone, such as a surface plasmon excitation device and a fluorescence measurement device. Furthermore, a sample containing a known amount of progesterone, an instruction manual, or the like may be included as an element of the kit.

[Progesterone Measuring Method]

According to the present invention, a progesterone measuring method is provided, the method including:
  a step (i) of mixing a first particle (a) having a label and modified with a first binding substance capable of specifically binding to progesterone, a second particle (b) having no label and modified with a second binding substance incapable of specifically binding to progesterone, and a test sample (c) containing progesterone to obtain a mixture;

a step (Ii) of applying the mixture obtained in the step (i) onto a substrate;

a step (Iii) of capturing the first binding substance at a reaction site on the substrate having a substance capable of binding to the first binding substance; and a step (iv) of detecting the first particle having a label and modified with the first binding substance captured on the reaction site, in which the first particle having a label contains at least one compound represented by Formula (1) that is described in the present specification and a particle, an average particle diameter of the first particles is 50 to 250 nm, an average particle diameter of the second particles is 70 to 500 nm, and the average particle diameter of the second particles is larger than the average particle diameter of the first particles.

In the present invention, progesterone is measured by detecting a first particle having a label, modified with a first binding substance, and captured on a reaction site.

The measurement in the present invention is interpreted as the broadest concept as long as the measurement is measurement of the amount of progesterone. As a specific aspect of the measuring method, a competition method is preferable.

A case of quantifying progesterone is described below.

In the competition method, first, a progesterone immunoassay substrate on which a progesterone-albumin conjugate is immobilized is brought into contact with a biological sample containing progesterone and an anti-progesterone antibody-labeled fluorescent particle. In a case where progesterone is not present in the biological sample, an antigen-antibody reaction occurs on the substrate by the anti-progesterone antibody-labeled fluorescent particle and progesterone on the substrate (that is, progesteroneinaprogesterone-albumin conjugate). On the other hand, in the case where progesterone is present in the biological sample, an antigen-antibody reaction occurs between progesterone in the biological sample and the anti-progesterone antibody-labeled fluorescent particle, and an antigen-antibody reaction between the anti-progesterone antibody-labeled fluorescent particle and the progesterone on the substrate (that is, progesterone in the progesterone-albumin conjugate) is inhibited. After the above reaction is completed, anti-progesterone antibody-labeled fluorescent particles that do not bind to albumin on the substrate are removed. Then, by detecting a degree of formation of an immune complex (that is, the complex of the anti-progesterone antibody-labeled fluorescent particle and progesterone in the progesterone-albumin conjugate on the substrate) on the substrate as fluorescence intensity, the concentration of progesterone or the like in the biological sample can be measured.

The measurement form of the fluorescence in the competition method can adopt either plate reader measurement or flow measurement, and for example, measurement can be performed by the following method. In advance, a plurality of samples with known amounts of progesterone having different progesterone concentrations are prepared, and these samples and the anti-progesterone antibody-labeled fluorescent particles are mixed in advance. This liquid mixture is brought into contact with an area where the progesterone-albumin conjugate is immobilized. The fluorescence signal from the area where the progesterone-albumin conjugate is immobilized is measured as a plurality of fluorescence signals while the liquid mixture is in contact with the conjugate at specific time intervals. From the plurality of fluorescence signals, temporal change (slope) in the fluorescence amount is acquired at each progesterone concentration. The temporal change is plotted as a Y axis and the progesterone concentration is plotted as an X axis, and a relational expression of the progesterone concentration with respect to the temporal change in the fluorescence amount is acquired using an appropriate fitting method such as the least squares method. The amount of progesterone contained in the biological sample can be quantified using the result of the temporal change in the fluorescence amount using the biological sample to be tested based on the relational expression thus acquired.

It is preferable to perform this quantification of the amount of progesterone in a short time. Specifically, the quantification is preferably performed within 10 minutes, more preferably within 8 minutes, and still more preferably within 6 minutes. This quantification time preferably includes time required to convert the amount of progesterone which is contained in the biological sample, based on the result of the temporal change in the fluorescence amount acquired using the biological sample to be tested after the sample and the anti-progesterone antibody-labeled fluorescent particles are brought into contact with detection area where the progesterone-albumin conjugate is immobilized, by using the relational expression between the temporal change in the fluorescence amount and the progesterone concentration, which is acquired in advance using an appropriate fitting method such as the least squares method.

(Surface Plasmon Fluorescence Measurement)

The method for detecting a label such as fluorescence in the present invention is not particularly limited. For example, it is preferable that fluorescence intensity is detected using a device capable of detecting fluorescence intensity, specifically, a microplate reader or a biosensor for performing fluorescence detection by surface plasmon excitation (SPF). Preferably, label information related to the amount of progesterone can be acquired by fluorescence detection by using surface plasmon resonance.

A form of measurement of fluorescence may be plate reader measurement or flow measurement. In a fluorescence detection method by surface plasmon excitation (SPF method), the measurement can be performed with higher sensitivity than in a fluorescence detection method by epi-excitation (epi-fluorescence method).

As a surface plasmon fluorescence (SPF) biosensor, a sensor described in JP2008-249361A, comprising: an optical waveguide formed of a material which transmits excitation light of a predetermined wavelength; a metal film formed on one surface of the optical waveguide; a light source for generating a light beam; an optical system for passing the light beam through the optical waveguide and causing the light beam to be incident on an interface between the optical waveguide and the metal film at an incidence angle generating the surface plasmon; and fluorescence detection means for detecting fluorescence generated by being excited by an evanescent wave enhanced due to the surface plasmon can be used.

The fluorescence detection (SPF) system by surface plasmon excitation using the fluorescent particles of the present invention is preferably an assay method for detecting fluorescence from the fluorescent substance depending on the amount of progesterone immobilized on the metal film on the substrate, and for example, is a method different from a so-called latex agglutination method in which a change in optical transparency by the progress of a reaction in a solution is detected as turbidity. In the latex agglutination method, an antibody-sensitized latex in a latex reagent and an antigen in a biological sample are bound to be agglutinated by an antibody reaction. The latex agglutination method is a method in which the agglutinate increases over time, and the antigen concentration is quantified from the change in absorbance per unit time obtained by irradiating the agglutinate with near-infrared light. In the present invention, it is possible to provide a substantially simple method for detecting progesterone, as compared with the latex agglutination method.

(Standardization)

Furthermore, the method according to the embodiment of the present invention may be a method including: a labeled particle-related label information acquisition step of acquiring label information related to the amount of the labeled particle; and a standardization step of standardizing label information acquired in a progesterone-related label information acquisition step of acquiring label information related to the amount of progesterone, by the label information acquired in the labeled particle-related label information acquisition step.

In a step of bringing a liquid mixture containing a biological sample and a labeled particle having a first binding substance capable of binding to progesterone into contact with a substrate having a detection area (test area) and a reference area (control area) to generate the surface plasmon on the detection area and the reference area, and measuring intensity of emitted fluorescence, a step of measuring intensity of the fluorescence by the surface plasmon generated on the detection area is the progesterone-related label information acquisition step of acquiring label information related to the amount of progesterone, and a step of measuring intensity of the fluorescence by the surface plasmon generated on the reference area is the labeled particle-related label information acquisition step. A step of acquiring an increase rate in the unit time of the fluorescence intensity acquired in these two steps as change rate of fluorescence signal values and dividing a change rate of signal values of the detection area by a change rate of the signal value of the reference area is a standardization step.

[Progesterone Measuring Reagent]

According to the present invention, a progesterone measuring reagent are provide, the reagent including a first particle (a) having a label and modified with a first binding substance capable of specifically binding to progesterone; and a second particle (b) having no label and modified with a second binding substance incapable of specifically binding to progesterone, in which the first particle having a label contains at least one compound represented by Formula (1) that is described in the present specification and a particle, and an average particle diameter of the first particles is 50 to 250 nm, an average particle diameter of the second particles is 70 to 500 nm, and the average particle diameter of the second particles is larger than the average particle diameter of the first particles.

The progesterone measuring method according to the embodiment of the present invention can be performed by using the above-mentioned progesterone measuring reagent.

Hereinafter, the present invention will be described in more detail with reference to the Examples of the present invention. The materials, amounts of use, proportions, treatment contents, treatment procedures, and the like shown in the following Examples can be appropriately modified without departing from the spirit and scope of the present invention.

Therefore, the scope of the present invention should not be interpreted restrictively by the following specific examples.

EXAMPLES

<1> Preparation of Latex Particles

<1-1> Preparation of Latex Particles with Average Particle Diameter of 303 nm 30 g (288 mmol) of styrene (manufactured by Wako Pure Chemical Industries, Ltd.) and 1 g (12 mmol) of acrylic acid (manufactured by Wako Pure Chemical Industries, Ltd.) were suspended in 330 mL of ultrapure water, the mixture was heated to 85° C., an aqueous solution in which 1 g of potassium persulfate (KPS, manufactured by Wako Pure Chemical Industries, Ltd.) was dissolved in 25 mL of water was added thereto, and the mixture was stirred at 85° C. and 250 rpm for 6 hours. Then, centrifugation was performed three times at 10,000 rpm for 6 hours to obtain latex particles. Finally, the obtained latex particles were re-dispersed in ultrapure water. Pure water was added thereto to prepare a diluted solution so that a concentration of the solid content was 1% by mass. The average particle diameter of the latex particles, which was obtained as a median diameter (d=50) measured at a temperature of 25° C. using a particle analyzer FPAR-1000 (Otsuka Electronics Co., Ltd.), was 303 nm.

<1-2> Preparation of Latex Particles with Average Particle Diameter of 220 nm 30 g (288 mmol) of styrene (manufactured by Wako Pure Chemical Industries, Ltd.) and 2 g (24 mmol) of acrylic acid (manufactured by Wako Pure Chemical Industries, Ltd.) were suspended in 330 mL of ultrapure water, the mixture was heated to 85° C., an aqueous solution in which 1 g of potassium persulfate (KPS, manufactured by Wako Pure Chemical Industries, Ltd.) was dissolved in 25 mL of water was added thereto, and the mixture was stirred at 85° C. and 250 rpm for 6 hours. Then, centrifugation was performed three times at 10,000 rpm for 6 hours to obtain latex particles. Finally, the obtained latex particles were re-dispersed in ultrapure water. Pure water was added thereto to prepare a diluted solution so that a concentration of the solid content was 1% by mass. The average particle diameter of the latex particles, which was obtained as a median diameter (d=50) measured at a temperature of 25° C. using a particle analyzer FPAR-1000 (Otsuka Electronics Co., Ltd.), was 220 nm.

<1-3> Preparation of Latex Particles with Average Particle Diameter of 151 nm 30 g (288 mmol) of styrene (manufactured by Wako Pure Chemical Industries, Ltd.) and 3 g (42 mmol) of acrylic acid (manufactured by Wako Pure Chemical Industries, Ltd.) were suspended in 440 mL of ultrapure water, the mixture was heated to 95° C., an aqueous solution in which 1 g of potassium persulfate (KPS, manufactured by Wako Pure Chemical Industries, Ltd.) was dissolved in 10 mL of water was added thereto, and the mixture was stirred at 95° C. and 250 rpm for 6 hours. Then, centrifugation was performed three times at 10,000 rpm for 6 hours to obtain latex particles. Finally, the obtained latex particles were re-dispersed in ultrapure water. Pure water was added thereto to prepare a diluted solution so that a concentration of the solid content was 1% by mass. The average particle diameter of the latex particles, which was obtained as a median diameter (d=50) measured at a temperature of 25° C. using a particle analyzer FPAR-1000 (Otsuka Electronics Co., Ltd.), was 151 nm.

<1-4> Preparation of Latex Particles with Average Particle Diameter of 129, 100, and 72 nm Latex particles with an average particle diameter of 129, 100, and 72 nm were prepared by appropriately adjusting the temperature at the time of raising the temperature, in preparing latex particles with an average particle diameter of 151 nm. The average particle diameter was measured in the same manner as in <1-1>.

<2> Preparation of Comparative Fluorescent Latex Particle 100 mL of methanol was added to 100 mL of an aqueous dispersion liquid of the latex particles having a concentration of solid content of 2% by mass prepared as described above, followed by stirring for 10 minutes at room temperature. On the other hand, a separately prepared fluorescent dye (comparative compound: Compound 5 described in JP3442777B) was gradually added dropwise into the latex solution over 60 minutes. After completion of the dropwise addition, an organic solvent was distilled off under reduced pressure with an evaporator, and then centrifugation and redispersion in an aqueous PBS solution were repeated three times to perform purification, thereby preparing six kinds of comparative fluorescent latex particles having an average particle diameter of 302 nm, 218 nm, 150 nm, 132 nm, 98 nm, and 71 nm.

<3> Preparation of Comparative Fluorescent Latex Particles Modified with Anti-Progesterone Antibody Fluorescent particles modified with an anti-progesterone antibody were prepared as follows.

375 μL of an aqueous solution in which the fluorescent latex particles with an average particle diameter of 150 nm, which was prepared in <2>, were contained at 2% by mass (solid content concentration) was prepared, and 117 μL of a buffer solution (pH of 6.0) of 50 mmol/L MES (2-morpholinoethanesulfonic acid, manufactured by Dojindo Molecular Technologies, Inc.) and 5 μL of an aqueous solution of 10 mg/mL water-soluble carbodiimide (WSC) were added thereto, followed by stirring at room temperature for 15 minutes. Subsequently, 182.4 L of a 0.5 mg/mL anti-progesterone monoclonal antibody (manufactured by GeneTex, Inc.) was added, followed by stirring at room temperature for 1.5 hours. 37.5 μL of an aqueous solution of 2 mol/L glycine (manufactured by Wako Pure Chemical Industries, Ltd.) was added, followed by stirring for 15 minutes, and then the fluorescent latex particles were precipitated by centrifugation (15,000 rpm, 4° C., 30 minutes). A supernatant liquid was removed, 750 μL of a phosphate buffered saline (PBS, manufactured by Wako Pure Chemical Industries, Ltd.) solution (pH of 7.4) was added, and the fluorescent latex particles were re-dispersed with an ultrasonic cleaner. Centrifugation (15,000 rpm, 4° C., 15 minutes) was performed, a supernatant liquid was removed, followed by addition of 750 μL of a PBS (pH of 7.4) solution containing 1% by mass of BSA, and then the fluorescent latex particles were re-dispersed to obtain a solution of 1 mass % anti-progesterone antibody-bound fluorescent latex particles. Fluorescent latex particles having an average particle diameter of 303 nm, 220 nm, 129 nm, 100 nm, and 72 nm were modified with an anti-progesterone antibody in the same manner.

<4> Preparation of Latex Particles Having No Fluorescence Label

Latex particles modified with an anti-T4 antibody were prepared as follows.

250 μL of a 50 mmol/L MES buffer (pH of 6.0) solution was added to 250 μL of an aqueous solution in which latex particles with an average particle diameter of 151 nm, which was prepared in <1-3>, was contained at 2% by mass (solid content concentration) and 100 μL of a 5 mg/mL anti-T4 monoclonal antibody (Medix Biochemica, Anti-Thyroxine monoclonal antibody (6901)) was added thereto, followed by stirring at room temperature for 15 minutes. Thereafter, 5 μL of an aqueous solution of 10 mg/mL 1-ethyl-3-(3-dimethylaminopropyl) carbodiimide (EDC) was added and followed by stirring at room temperature for 2 hours. 25 μL of an aqueous solution of 2 mol/L glycine (manufactured by Wako Pure Chemical Industries, Ltd.) was added, followed by stirring for 30 minutes, and then the latex particles were precipitated by centrifugation (15,000 rpm, 4° C., 15 minutes). Thereafter, supernatant was removed, 500 μL of PBS solution (pH of 7.4) was added, and the latex particles were re-dispersed with an ultrasonic cleaner. Centrifugation (15,000 rpm, 4° C., 15 minutes) was performed again, supernatant was removed, followed by addition of 500 μL of a PBS (pH of 7.4) solution containing 1% by mass of BSA, and then the latex particles were re-dispersed to prepare a solution of 1 mass % anti-T4 antibody-bound latex particles. Other latex particles (302 nm, 218 nm, 132 nm, 98 nm, and 71 nm) were modified with the anti-T4 antibody in the same manner.

In the same manner, using an anti-hCG antibody (Medix Biochemica, anti-hCGbeta monoclonal antibody (5008)), anti-hCG antibody modification was performed on the latex particles having each average particle diameter.

As the notation of the type of the mouse antibody of the unlabeled particles, 1 indicates the anti-T4 antibody and 2 indicates the anti-hCG antibody in Table 3 below.

<5> Preparation of High Luminescent Fluorescent Latex Particles

<5-1> Synthesis of Compound

The terms have the following meanings.

MS: mass spectrometry

ESI: electrospray ionization

NMR: nuclear magnetic resonance rt: room temperature

Et: ethyl group

PL: photoluminescence

THF: tetrahydrofuran

Synthesis of Compound (1)

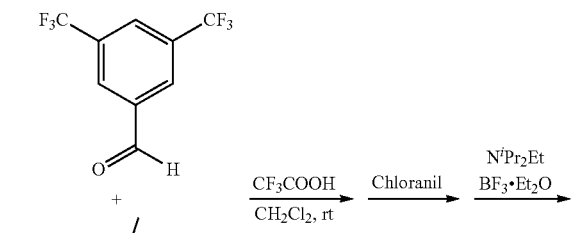

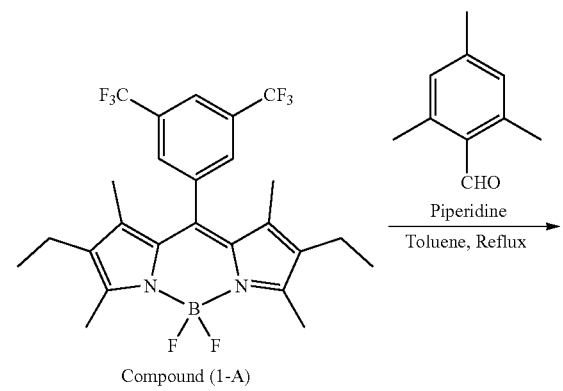

Compound (1-A)

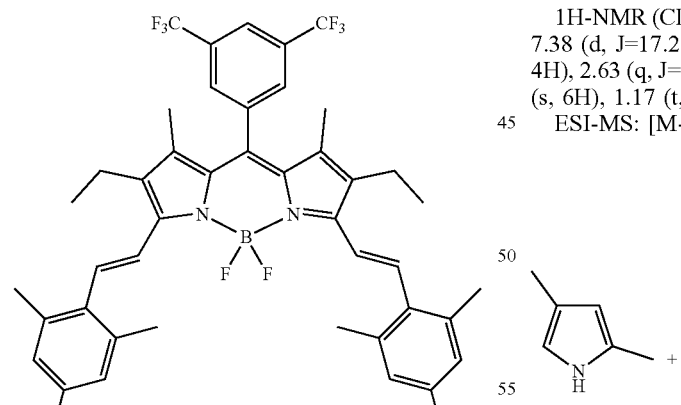

Compound (1)

Synthesis of Compound (1-A)

1.00 g of 3,5-bis(trifluoromethyl)benzaldehyde and 20 mL of dichloromethane were introduced into a 100 mL three-neck flask under a nitrogen atmosphere, followed by stirring at room temperature. While cooling with water, 0.98 g of 3-ethyl-2,4-dimethylpyrrole was added dropwise, followed by addition of two drops of trifluoroacetic acid and then stirring at room temperature for 30 minutes. 1.0 g of chloranil was added while cooling with water, followed by stirring at room temperature for 10 minutes, and then 3.67 g of diisopropylethylamine (N$^i$Pr$_2$Et) was added dropwise while cooling with water, followed by stirring at room temperature for 15 minutes. Subsequently, 5.6 mL of a boron trifluoride-diethyl ether complex was added dropwise while cooling with water, followed by stirring at room temperature for 30 minutes. Saturated sodium hydrogen carbonate and toluene were added dropwise, and an organic layer obtained by extraction and liquid separation was preliminarily dried over anhydrous sodium sulfate and then concentrated under reduced pressure. The resulting crude product was purified by silica gel column chromatography (developing solvent: hexane/ethyl acetate) and then recrystallized from methanol to obtain 1.28 g of Compound (1-A).

1H-NMR (CDCl$_3$, 400 MHz): δ 8.03 (s, 1H), 7.83 (s, 2H), 2.54 (s, 6H), 2.31 (q, J=7.6 Hz, 4H), 1.21 (s, 6H), 1.00 (t, J=7.6 Hz, 6H).

Synthesis of Compound (1)

100 mg of Compound (1-A), 115 mg of 2,4,6-trimethylbenzaldehyde, and 5 mL of dehydrated toluene were introduced into a 100 mL three-neck flask, followed by stirring at room temperature. 1 mL of piperidine and one piece of p-toluenesulfonic acid monohydrate (manufactured by Wako Pure Chemical Industries, Ltd., special grade chemical) were added thereto, followed by stirring for 1 hour while distilling off the solvent at 140° C., and after cooling, 5 ml of dehydrated toluene was added thereto, followed by stirring for 1 hour while distilling off the solvent at 140° C. The crude product obtained by concentrating the reaction liquid under reduced pressure was purified by preparative TLC (developing solvent: hexane/ethyl acetate) and then recrystallized from methanol to obtain 71 mg of Compound (1). Identification of the compound was carried out by $^1$H-NMR and ESI-MS.

1H-NMR (CDCl$_3$, 400 MHz): δ 8.06 (s, 1H), 7.87 (s, 2H), 7.38 (d, J=17.2 Hz, 2H), 7.32 (d, J=17.2 Hz, 2H), 6.93 (s, 4H), 2.63 (q, J=7.6 Hz, 4H), 2.44 (s, 12H), 2.30 (s, 6H), 1.27 (s, 6H), 1.17 (t, J=7.6 Hz, 6H).

ESI-MS: [M-H]$^-$=775.8

Synthesis of Compound (5)

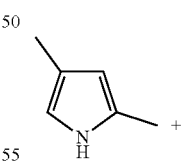

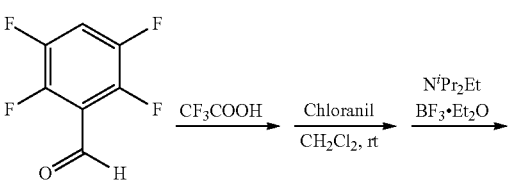

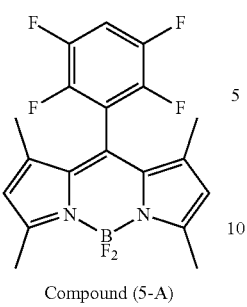

Compound (5-A)

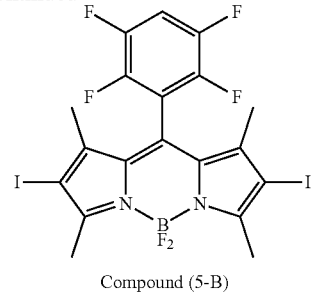

Compound (5-B)

Synthesis of Compound (5-A)

1.16 ml of 2,4-dimethylpyrrole and 140 mL of dichloromethane were introduced into a 500 mL three-neck flask under a nitrogen atmosphere, followed by stirring at room temperature. 1.0 g of 2,3,5,6-tetrafluorobenzaldehyde and one drop of trifluoroacetic acid were added, followed by stirring at room temperature for 15 minutes. 1.38 g of chloranil was added, followed by stirring at room temperature for 15 minutes, and then 6.8 mL of diisopropylethylamine ($N^i Pr_2 Et$) was added dropwise while cooling with water, followed by stirring at room temperature for 20 minutes. Subsequently, 7.8 mL of a boron trifluoride-diethyl ether complex ($BF_3.Et_2O$) was added dropwise while cooling with water, followed by stirring at room temperature for 30 minutes. 400 mL of saturated sodium hydrogen carbonate was added dropwise, and an organic layer obtained by dichloromethane extraction and liquid separation was preliminarily dried over anhydrous sodium sulfate and then concentrated under reduced pressure. The resulting crude product was purified by silica gel column chromatography (developing solvent: hexane/ethyl acetate) and then recrystallized from methanol to obtain 360 mg of Compound (5-A).

300 mg of Compound (5-A) and 8 mL of 1,1,1,3,3,3-hexafluoro-2-propanol were introduced into a 300 mL three-neck flask, followed by stirring at room temperature. 409 mg of N-iodosuccinimide was introduced, followed by stirring at room temperature for 1 hour. After concentrating the reaction liquid under reduced pressure, 40 mL of methylene chloride was added, and an organic layer obtained by extraction and liquid separation was preliminarily dried over anhydrous sodium sulfate, filtered, and concentrated under reduced pressure. Ethanol was added to the resulting crude product, followed by dispersion, washing, and filtration to obtain 382 mg of Compound (5-B).

Synthesis of Compound (5-C)

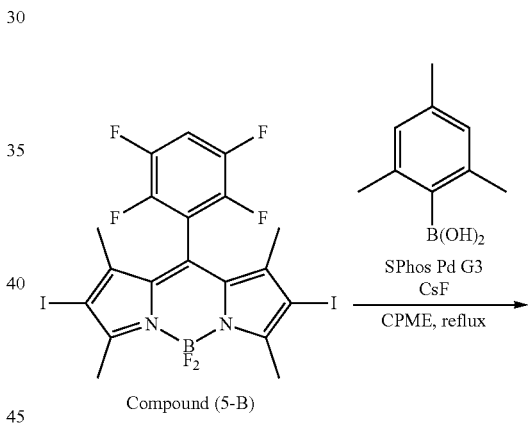

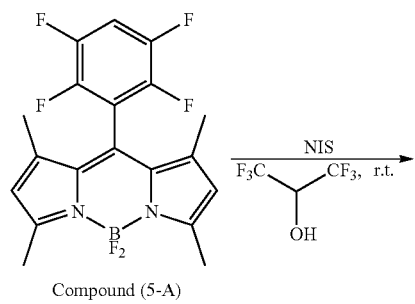

Compound (5-C)

278 mg of Compound (5-B), 564 mg of 2,4,6-trimethylphenylboronic acid, 653 mg of cesium fluoride, and 43 mL of methoxycyclopentane were introduced into a 100 mL three-neck flask, followed by degassing under reduced pressure while stirring at room temperature, and the reaction

Synthesis of Compound (5-B)

system was set to a nitrogen atmosphere. 269 mg of SPhos Pd G3 (manufactured by Sigma-Aldrich, Inc.) was added thereto, followed by heating under reflux for 1 hour. 250 mL of ethyl acetate was added, and an organic layer obtained by extraction and liquid separation was preliminarily dried over anhydrous sodium sulfate and then concentrated under reduced pressure. The resulting crude product was purified by silica gel column chromatography (developing solvent: hexane/ethyl acetate) and then dissolved in 5 ml of dichloromethane, 15 ml of methanol was further added, and then dichloromethane was distilled off, followed by reprecipitation. The precipitate was filtered to obtain 206 mg of Compound (5-C).

Synthesis of Compound (5)

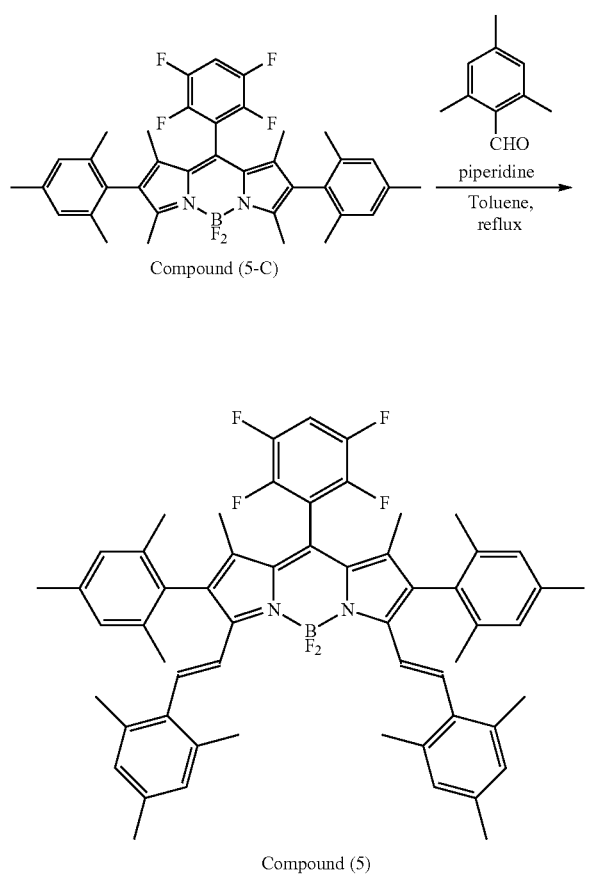

Compound (5-C)

Compound (5)

50 mg of Compound (5-C), 5 ml of toluene, 46 µl of 2,4,6-trimethylbenzaldehyde, 400 µl of piperidine, and one piece of p-toluenesulfonic acid were introduced into a 100 mL three-neck flask, followed by heating under reflux under nitrogen atmosphere for 1 hour. After further adding 46 µl of 2,4,6-trimethylbenzaldehyde, followed by heating under reflux for 1 hour, 200 µl of piperidine was further added, followed by heating under reflux for another 1 hour. After completion of the reaction, the reaction liquid was concentrated under reduced pressure. The resulting crude product was purified by silica gel column chromatography (developing solvent: hexane/toluene) and then dissolved in 3 ml of dichloromethane, 15 ml of methanol was added, and then dichloromethane was distilled off, followed by reprecipitation to obtain 16 mg of Compound (5). Identification of the compound was carried out by $^1$H-NMR and ESI-MS.

$^1$H-NMR (CDCl$_3$, 400 MHz): δ 7.43 (s, 1H), 7.39 (s, 1H), 7.29-7.21 (m, 1H), 6.94 (s, 4H), 6.80 (s, 4H), 6.69 (s, 1H), 6.65 (s, 1H), 2.29 (s, 6H), 2.23 (s, 6H), 2.08 (s, 12H), 2.03 (s, 12H), 1.33 (s, 6H).

ESI-MS: [M-H]$^-$=891.4

<5-2> Preparation of High Luminescent Fluorescent Latex Particles

THF (5 mL) was added dropwise to the dispersion liquid of latex particles having an average particle diameter of 151 nm, which was prepared in <1-3> and had the solid content concentration of 2% by mass (25 mL of latex dispersion liquid, 500 mg of solid content), and followed by stirring for 10 minutes. A THF solution (2.5 mL) containing 48 µmol/g of Compound (5) was added dropwise thereto over 15 minutes. A THF solution (2.5 mL) containing 48 µmol/g of Compound (1) was added dropwise thereto over 15 minutes. Completion of the dropwise addition of the compound was followed by stirring for 30 minutes and concentrating under reduced pressure to remove THF. Thereafter, the particles were precipitated by centrifugation, followed by addition of ultrapure water, and then dispersed again to prepare the high luminescent fluorescent latex particles having a solid content concentration of 2% by mass. In addition, the same operation was performed using Compound (5) instead of Compound (1) to produce a high luminescent fluorescent latex dispersion liquid having a solid content concentration of 2% and containing Compound (5).

Further, the same operation was performed using a mixture of 24 µmol/g of Compound (1) and 12 µmol/g of Compound (5) to produce a high luminescent fluorescent latex dispersion liquid having a solid content concentration of 2% by mass containing Compound (1) and Compound (5).

The same operation was performed for latex particles having other average particle diameters (303 nm, 220 nm, 129 nm, 100 nm, and 72 nm) to individually obtain high luminescent fluorescent latex dispersion liquids having a solid content concentration of 2% and containing only compound (1), only Compound (5), or both Compound (1) and Compound (5).

<5-3> Preparation of High Luminescent Fluorescent Latex Particles Modified with Anti-Progesterone Antibody 1% by mass solution of high luminescent fluorescent latex particles to which an anti-progesterone antibody was bound and which had average particle diameters of 303 nm, 220 nm, 151 nm, 129 nm, 100 nm, and 72 nm were prepared by performing the same operations as in <3>, using each of the high luminescent fluorescent latex particles, which was prepared in <5-2>, having a solid content concentration of 2% by mass.

<6> Preparation of Dry Particles of Particles Having a Fluorescence Label and Particles Having No Fluorescence Label 280 µL of ultrapure water, 427 µL of an aqueous solution of 12.5 mass % sucrose, 133 µL of an aqueous solution of 20 mass % BSA, 80 µL of 1 mass % fluorescent latex particles modified with an anti-progesterone antibody (average particle size of 150 nm), and a dispersion of 80 µL of 1 mass % latex particles modified with an anti-T4 antibody (average particle diameter of 150 nm) were mixed. A cup made of polypropylene (Prime Polymer Co., Ltd., Prime Polypro random PP grade) was prepared and 15 µL of the mixture was spotted thereon. Thereafter, the mixture was dried until the water content became 25% by mass or less over 12 hours using a SUPER DRY dryer (TOYO Living Co., Ltd., ULTRA SUPER DRY 00 SERIES), and dry particles were prepared. For the dry particles used in the other experimental examples, the average particle diameter of the latex particles and the mass ratio of the anti-progesterone antibody-modified fluorescent latex particles to the anti-T4 antibody-modified latex particles were appropriately changed as shown in Table 3 and dry particles were prepared.

<7> Preparation of Substrate

<7-1> Preparation of Solution of Progesterone-BSA Conjugate in Citrate Buffer Solution 150 g of a progesterone-BSA conjugate (manufactured by Bio-Rad Laboratories, Inc.) was added to and dissolved in 1 mL of a citrate buffer solution at a concentration of 50 mmol/L (pH of 5.2, 150 mmol/L NaCl), thereby obtaining a solution of a progesterone-BSA conjugate in a citrate buffer solution.

<7-2> Preparation of Anti-Mouse Antibody

Immunization (subcutaneous immunization) on goat was performed four times at two-week intervals by a method in which mouse-derived globulin (manufactured by LAMPIRE Biological Laboratories, Inc., catalog number 7404302, Mouse Gamma Globulin Salt Fractionation, 500 mg) was prepared, an emulsion obtained by mixing with the complete Freund's adjuvant (CFA) was administered to a goat for a first immunization, and an emulsion obtained by mixing with an incomplete Freund's adjuvant (IFA) was administered to a goat for second to fourth immunizations. Thereafter, ELISA measurement was performed to confirm a rise in the antibody titer, then whole blood was collected, and centrifugation was performed to obtain an antiserum. Then, purification was performed with a Protein A column (manufactured by Thermo Fisher Scientific, Inc., Pierce Protein A Columns, catalog number 20356) to obtain a target anti-mouse antibody.

<7-3> Preparation of Progesterone-BSA Conjugate-Immobilized Substrate

A polymethyl methacrylate (PMMA) substrate (manufactured by Mitsubishi Rayon Co., Ltd., ACRYPET VH) was prepared, a gold film having thickness of 45 nm was prepared on one side of the substrate at two places of a detection area and a reference area so as to have a width of 4 mm and a length of 3 mm, and thus a chip for constituting a substrate was prepared by a magnetron sputtering method. The solution of the progesterone-BSA conjugate in the citrate buffer solution prepared in <7-1> was spotted on the gold film surface of the detection area of this chip, and dried to prepare a substrate on which the progesterone-BSA conjugate is immobilized. In addition, a solution containing the anti-mouse antibody prepared in <7-2> (concentration: 50 µg/mL in 50 mmol/L of MES buffer solution, pH of 6, 150 mmol/L NaCl) was spotted on the reference area of each substrate and dried.

<8> Washing and Blocking of Substrate

Before attaching the substrate prepared as described to a flow channel of a sensor chip, the substrate was repeatedly washed three times with 300 µL of a solution for washing (PBS solution (pH of 7.4) containing 0.05% by mass of Tween (registered trademark) 20 (polyoxyethylene (20) sorbitan monolaurate, Wako Pure Chemical Industries, Ltd.)) prepared in advance. After completion of the washing, in order to block a portion on the thin gold film, which was not adsorbed with an antibody, 300 µL of a PBS solution (pH of 7.4) containing 1% by mass of casein (manufactured by Thermo Fisher Scientific Inc.) was added, followed by being left to stand for 1 hour at room temperature. After washing with the solution for washing, 300 µL of Immunoassay Stabilizer (manufactured by Advanced Biotechnologies Inc.) was added as a stabilizer, followed by being left to stand for 30 minutes at room temperature. Then, the solution was removed and the moisture was completely removed using a drier.

<9> Preparation of Sensor Chip

Figure 2:
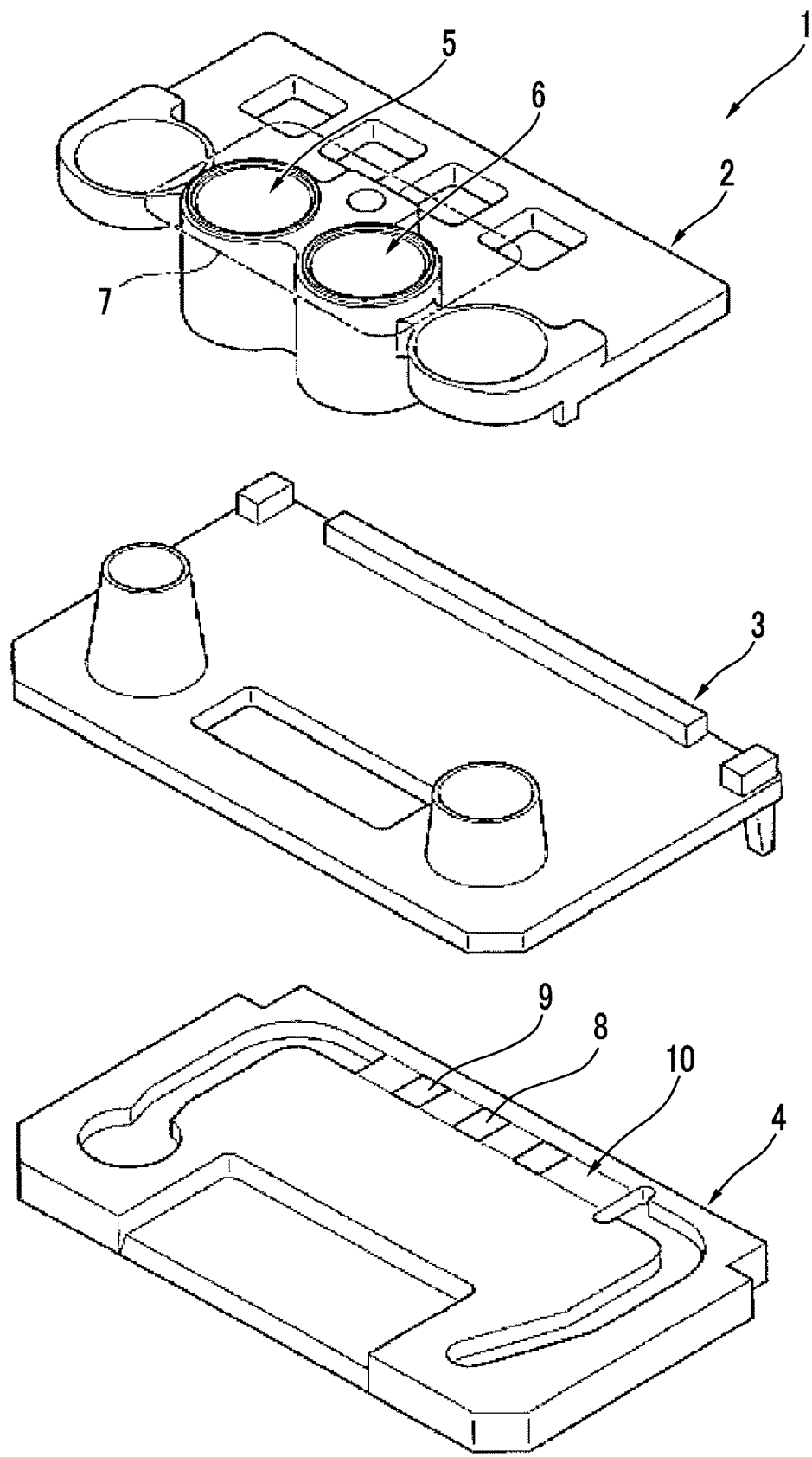
FIG. 2 shows an exploded view of the sensor chip.

The prepared substrate was enclosed in the flow channel and a flow channel-type sensor chip was prepared to have the configuration of the second embodiment in JP2010-190880A. The schematic views thereof are shown in FIG. 1 and FIG. 2. FIG. 1 is a schematic view of a sensor chip 1, and FIG. 2 is an exploded view of the sensor chip 1. The sensor chip 1 includes an upper member 2, an intermediate member 3, and a substrate 4. The upper member 2 is provided with a first container 5 and a second container 6. The first container 5 and the second container 6 are collectively referred to as a container group 7. A flow channel 10 is formed in the substrate 4, and a detection area 8 and a reference area 9 are formed on the flow channel 10.

<10> Preparation of Test Sample

For evaluating a calibration curve, samples containing progesterone having various concentrations (0.00 ng/mL, 0.5 ng/mL, 2.0 ng/mL, 15.0 ng/mL, 30.0 ng/mL, and 45.0 ng/mL) were prepared.

In addition, for evaluating the performance, test samples (specimens) Nos. 1 to 11 were prepared using the sera of Toyo beagle dogs purchased from Kitayama Labes Co., Ltd., as dog sera.

<11> Immunoassay of Progesterone Using Fluorescent Particle

After storing the dry particles in the cup, which were prepared in <6>, in an environment of 25° C. and 50% relative humidity (RH) for 15 days, a mixed sample prepared by thoroughly mixing 100 µL of each of the samples containing progesterone of various concentrations prepared in <10> and the test samples (specimens) with 44 µmol of magnesium chloride was spotted in this cup, and mixed while stirring for 10 minutes to obtain a liquid mixture. Then, on the flow channel-type sensor chip which was prepared in <9> and in which the substrate was enclosed, a predetermined amount of the obtained liquid mixture was spotted. After spotting was completed, the liquid mixture was allowed to flow down at a rate of 10 µL/min while pump suction was performed. The fluorescence intensity on the thin gold film surface on which the progesterone-BSA conjugate was immobilized was continuously measured for 1.5 minutes. The rate of increase in the obtained fluorescence intensity per unit time was determined as a fluorescence signal value.

<12> Creation of Calibration Curve

Literature "The Immunoassay Handbook Third Edition Edited by David Wild (2005)" describes that a four-parameter logistic curve model of a sigmoid function can be applied as a calibration curve of a competition method, and according to this method, a four-parameter logistic curve passing the nearest neighbor of each point of the fluorescence signal values, which were measured in <11>, in various concentrations (0.00 ng/mL, 0.5 ng/mL, 2.0 ng/mL, 15.0 ng/mL, 30.0 ng/mL, 45.0 ng/mL) of the samples including progesterone was acquired for each of Comparative examples and Examples described in Table 3 below, by using the least squares method generally known as a method for obtaining an approximate line, and the curve was set as a calibration curve.

From the calibration curve acquired as described above, the measurement value of each of the progesterone concentrations of the test samples (specimens) Nos. 1 to 11 was calculated.

The performance of the measurement was determined according to whether to satisfy the standard of the calibration curve. The calibration curve determined the standard by two points. A first point was a slope of the calibration curve in a low concentration range of the progesterone, and a case where a reciprocal of the slope was within 1.4 was set as a standard. A second point was a deviation from the calibration curve at the measurement point in a high concentration range of the progesterone, and a case where the deviation was within 2% was set as a standard. Within the range of the standards, it is possible to achieve the coefficient of variation of the measurement value within 10% and the precision within 10%. In addition, since it is possible to realize that the accuracy is within 10%, it is possible to perform highly accurate measurement from the low concentration region to the high concentration region.

In a case of the concentration of progesterone in a low concentration range, which was determined as the standard, a slope of a calibration curve at 0.5 ng/mL as the minimum concentration of progesterone which is clinically meaningful was acquired. In addition, in a case of the concentration of progesterone in a high concentration range, which was determined as the standard, deviations from the calibration curve at progesterone concentrations of 30.0 ng/mL and 45.0 ng/mL were respectively acquired, and an average value thereof was calculated and evaluated. The results are summarized in Table 3.

<13> Measurement by Control Apparatus

In immunoassay, measurement of the test substance in the test sample was performed by using an IMMULYZE 1000 automated immunochemiluminescence analyzer (Siemens Healthcare K.K.), which is a large-scale apparatus widely used by those skilled in the art and according to the instruction manual. The measurement was performed on the test samples (specimens) Nos. 1 to 11 prepared in <10>. The present invention enables quick and simple measurement based on a measurement value measured by a control device and requires a small difference in measurement value from the control device. Therefore, using a measurement value of progesterone in test sample (specimen) No. 1, which was obtained from a large-scale apparatus, and measurement values of progesterone (progesterone measurement values of the present invention) determined from the calibration curve prepared in <12>, evaluation was performed according to the following criteria, and the results are shown in Table 3.

Calculation expression for calculating deviation width (%) from large-scale apparatus $$\frac{|(\text{Measured value of progesterone in large-scale apparatus}) - (\text{Measured value of progesterone in the present invention})|}{(\text{Measured value of progesterone in large-scale apparatus})} \times 100 \quad \text{(Calculation expression 1)}$$

<Evaluation Criteria>

Regarding the reciprocal of the slope of the calibration curve in the low concentration range, the determination was set as A in a case where the reciprocal thereof was within 1.4, the determination was set as B in a case where the reciprocal thereof was larger than 1.5, and the determinations of A were regarded as an allowable range.

Regarding the deviations from the calibration curve in the high concentration region, the determination was set as A in a case where the deviation was less than 1.5%, the determination was set as B in a case where the deviation was 1.5% or more and 2% or less, the determination was set as C in a case where the deviation was more than 2%, and the determinations of A and B were regarded as an allowable range.

Regarding the deviation widths (%) from a large-scale apparatus, the determination was set as A in a case where the deviation width was less than 2.0%, the determination was set as B in a case where the deviation width was 2.0% or more and less than 5.0%, the determination was set as C in a case where the deviation width was 5.0% or more, and the determinations of A and B were regarded as an acceptable range.

<14> Measurement of Particle Fluorescence Intensity (Relative Value)

The fluorescence latex dispersion liquid having a solid content concentration of 2% by mass was diluted 200 times with ultrapure water, the excitation light of a fluorescence spectrophotometer RF-5300PC (manufactured by Shimadzu Corporation) was set to 658 nm, and measurement was performed. In a case where the fluorescence intensity of the fluorescent latex dispersion liquid was high enough to exceed the measurement range, dilution was performed with ultrapure water to a range in which the maximum value of the fluorescence intensity was measurable. An integrated value of the fluorescence intensity of the emission spectrum of the fluorescent latex dispersion liquid with respect to an integrated value of the fluorescence intensity of the emission spectrum of the fluorescent latex dispersion liquid prepared in <6> was taken as the particle fluorescence intensity (relative value). A calculation expression used for the calculation is shown below.

Fluorescence intensity (relative value)=(Integrated value of fluorescence intensity of emission spectrum of fluorescent latex dispersion liquid)/(Integrated value of fluorescence intensity of emission spectrum of fluorescent latex dispersion liquid prepared in <6>)

The results are shown in Table 3.

TABLE 3

| Compound | Particle fluorescence intensity (relative value) | Average particle size of labeled particles/nm | Average particle size of unlabeled particles/nm | Ratio of labeled particle/unlabeled particle | Type of mouse antibody of unlabeled particle | Reciprocal of slope of calibration curve in low concentration range (Criteria: 1.4 or less) | Determination | Deviation from calibration curve in high concentration range (Criteria: within 2%) |
|---|---|---|---|---|---|---|---|---|
| (1), (5) | 12.1 | 72 | 71 | 1/1 | 1 | 1.4 | A | 1.4% |
| (1), (5) | 12.1 | 303 | 302 | 1/1 | 1 | 1.1 | A | 2.4% |
| (1), (5) | 12.1 | 100 | 150 | 1/1 | 1 | 1.3 | A | 1.4% |
| (1), (5) | 12.1 | 100 | 132 | 1/1 | 1 | 1.3 | A | 1.7% |
| (1), (5) | 12.1 | 100 | 302 | 1/1 | 1 | 1.3 | A | 1.8% |
| (1), (5) | 12.1 | 72 | 132 | 1/1 | 1 | 1.4 | A | 1.4% |
| (1), (5) | 12.1 | 72 | 302 | 1/1 | 1 | 1.4 | A | 1.5% |
| (1), (5) | 12.1 | 129 | 150 | 1/1 | 1 | 1.3 | A | 1.8% |
| (1), (5) | 12.1 | 129 | 302 | 1/1 | 1 | 1.3 | A | 1.9% |
| (1), (5) | 12.1 | 220 | — | 1/0 | — | 1.7 | B | 1.4% |
| (1), (5) | 12.1 | 151 | — | 1/0 | — | 1.4 | A | 2.4% |
| (1), (5) | 12.1 | 220 | 218 | 1/1 | 1 | 1.4 | A | 2.5% |
| (1), (5) | 12.1 | 220 | 150 | 1/1 | 1 | 1.3 | A | 2.7% |
| (1), (5) | 12.1 | 151 | 150 | 1/1 | 1 | 1.2 | A | 2.9% |
| (1), (5) | 12.1 | 151 | 150 | 1/2 | 1 | 1.1 | A | 3.6% |
| (1), (5) | 12.1 | 151 | 150 | 1/4 | 1 | 1.2 | A | 2.1% |
| (1), (5) | 12.1 | 151 | 150 | 1/6 | 1 | 1.3 | A | 3.1% |
| (1), (5) | 12.1 | 100 | 98 | 1/4 | 1 | 1.5 | B | 2.6% |
| (1), (5) | 12.1 | 220 | 218 | 1/4 | 1 | 1.3 | A | 3.1% |
| (1), (5) | 12.1 | 151 | 150 | 1/4 | 2 | 1.2 | A | 3.3% |
| (1) | 5.8 | 72 | 71 | 1/1 | 1 | 1.4 | A | 1.5% |
| (1) | 5.8 | 303 | 302 | 1/1 | 1 | 1.2 | A | 2.3% |
| (1) | 5.8 | 100 | 150 | 1/1 | 1 | 1.4 | A | 1.4% |
| (1) | 5.8 | 100 | 130 | 1/1 | 1 | 1.3 | A | 1.8% |
| (1) | 5.8 | 100 | 302 | 1/1 | 1 | 1.4 | A | 1.9% |
| (1) | 5.8 | 72 | 130 | 1/2 | 1 | 1.3 | A | 1.6% |
| (1) | 5.8 | 72 | 302 | 1/4 | 1 | 1.4 | A | 1.4% |
| (1) | 5.8 | 100 | 150 | 1/6 | 1 | 1.3 | A | 1.1% |
| (1) | 5.8 | 129 | 302 | 1/4 | 1 | 1.4 | A | 1.8% |
| (1) | 5.8 | 220 | — | 1/0 | — | 1.8 | B | 1.1% |
| (1) | 5.8 | 151 | — | 1/0 | — | 1.7 | B | 3.2% |
| (1) | 5.8 | 220 | 218 | 1/1 | 1 | 1.6 | B | 2.6% |
| (1) | 5.8 | 220 | 150 | 1/1 | 1 | 1.5 | B | 2.5% |
| (1) | 5.8 | 151 | 150 | 1/1 | 1 | 1.4 | A | 3.1% |
| (1) | 5.8 | 151 | 150 | 1/2 | 1 | 1.3 | A | 3.4% |
| (1) | 5.8 | 151 | 150 | 1/4 | 1 | 1.3 | A | 2.7% |
| (1) | 5.8 | 151 | 150 | 1/6 | 1 | 1.2 | A | 3.6% |
| (1) | 5.8 | 100 | 98 | 1/4 | 1 | 1.6 | B | 3.3% |
| (1) | 5.8 | 220 | 218 | 1/4 | 1 | 1.4 | A | 3.5% |
| (1) | 5.8 | 151 | 150 | 1/4 | 2 | 1.3 | A | 3.3% |
| (5) | 7.0 | 72 | 71 | 1/1 | 1 | 1.3 | A | 1.6% |
| (5) | 7.0 | 303 | 302 | 1/1 | 1 | 1.2 | A | 2.6% |
| (5) | 7.0 | 100 | 150 | 1/1 | 1 | 1.2 | A | 1.9% |
| (5) | 7.0 | 100 | 130 | 1/1 | 1 | 1.4 | A | 1.8% |
| (5) | 7.0 | 100 | 302 | 1/1 | 1 | 1.3 | A | 1.9% |
| (5) | 7.0 | 72 | 130 | 1/2 | 1 | 1.2 | A | 1.3% |
| (5) | 7.0 | 72 | 150 | 1/2 | 1 | 1.1 | A | 1.1% |
| (5) | 7.0 | 72 | 150 | 1/4 | 1 | 1.1 | A | 1.1% |
| (5) | 7.0 | 72 | 150 | 1/6 | 1 | 1.1 | A | 1.0% |
| (5) | 7.0 | 72 | 302 | 1/4 | 1 | 1.3 | A | 1.4% |
| (5) | 7.0 | 129 | 150 | 1/6 | 1 | 1.4 | A | 1.3% |
| (5) | 7.0 | 129 | 302 | 1/4 | 1 | 1.4 | A | 1.4% |
| (5) | 7.0 | 220 | — | 1/0 | — | 1.9 | B | 1.7% |
| (5) | 7.0 | 151 | — | 1/0 | — | 1.6 | B | 3.1% |
| (5) | 7.0 | 220 | 218 | 1/1 | 1 | 1.5 | B | 2.8% |
| (5) | 7.0 | 220 | 150 | 1/1 | 1 | 1.6 | B | 2.6% |
| (5) | 7.0 | 151 | 150 | 1/1 | 1 | 1.5 | B | 3.4% |
| (5) | 7.0 | 151 | 150 | 1/2 | 1 | 1.5 | B | 3.8% |
| (5) | 7.0 | 151 | 150 | 1/4 | 1 | 1.4 | A | 2.4% |
| (5) | 7.0 | 151 | 150 | 1/6 | 1 | 1.6 | B | 3.5% |
| (5) | 7.0 | 100 | 98 | 1/4 | 1 | 1.7 | B | 3.1% |
| (5) | 7.0 | 220 | 218 | 1/4 | 1 | 1.4 | A | 3.6% |
| (5) | 7.0 | 151 | 150 | 1/4 | 2 | 1.2 | A | 3.4% |
| Comparative compound | 1.0 | 72 | 71 | 1/1 | 1 | 1.5 | B | 1.6% |
| Comparative compound | 1.0 | 303 | 302 | 1/1 | 1 | 1.6 | B | 6.6% |
| Comparative compound | 1.0 | 100 | 150 | 1/1 | 1 | 1.3 | A | 3.6% |

TABLE 3-continued

| | | | | | | | | |
|---|---|---|---|---|---|---|---|---|
| Comparative compound | 1.0 | 100 | 130 | 1/1 | 1 | 1.3 | A | 33% |
| Comparative compound | 1.0 | 100 | 302 | 1/1 | 1 | 1.3 | A | 3.2% |
| Comparative compound | 1.0 | 72 | 130 | 1/2 | 1 | 1.4 | A | 2.6% |
| Comparative compound | 1.0 | 72 | 302 | 1/4 | 1 | 1.4 | A | 3.1% |
| Comparative compound | 1.0 | 129 | 150 | 1/6 | 1 | 1.3 | A | 3.8% |
| Comparative compound | 1.0 | 129 | 302 | 1/4 | 1 | 1.3 | A | 3.9% |
| Comparative compound | 1.0 | 220 | — | 1/0 | — | 1.8 | B | 7.2% |
| Comparative compound | 1.0 | 151 | — | 1/0 | — | 1.5 | B | 4.5% |
| Comparative compound | 1.0 | 220 | 218 | 1/1 | 1 | 1.4 | A | 8.8% |
| Comparative compound | 1.0 | 220 | 150 | 1/1 | 1 | 1.3 | A | 5.2% |
| Comparative compound | 1.0 | 151 | 150 | 1/1 | 1 | 1.2 | A | 4.4% |
| Comparative compound | 1.0 | 151 | 150 | 1/2 | 1 | 1.1 | A | 4.6% |
| Comparative compound | 1.0 | 151 | 150 | 1/4 | 1 | 1.3 | A | 4.9% |
| Comparative compound | 1.0 | 151 | 150 | 1/6 | 1 | 1.3 | A | 4.5% |
| Comparative compound | 1.0 | 100 | 98 | 1/4 | 1 | 1.4 | A | 5.2% |
| Comparative compound | 1.0 | 220 | 218 | 1/4 | 1 | 1.2 | A | 7.2% |
| Comparative compound | 1.0 | 151 | 150 | 1/4 | 2 | 1.1 | A | 63% |

| Compound | Deviation from calibration curve in high concentration range Determination | Measured value of progesterone in large-scale apparatus | Measured value of progesterone in present invention | Deviation width from large-scale apparatus (Criteria: within 5%) | Determination | Note |
|---|---|---|---|---|---|---|
| (1), (5) | A | 10.2 | 16.1 | 57.8% | C | Comparative Example 1 |
| (1), (5) | C | 10.2 | 15.0 | 47.1% | C | Comparative Example 2 |
| (1), (5) | A | 10.2 | 10.5 | 2.9% | B | Present invention 1 |
| (1), (5) | B | 10.2 | 10.1 | 1.0% | A | Present invention 2 |
| (1), (5) | B | 10.2 | 10.4 | 2.0% | B | Present invention 3 |
| (1), (5) | A | 10.2 | 9.9 | 2.9% | B | Present invention 4 |
| (1), (5) | B | 10.2 | 10.4 | 2.0% | B | Present invention 5 |
| (1), (5) | B | 10.2 | 10.2 | 2.9% | B | Present invention 6 |
| (1), (5) | B | 10.2 | 10.4 | 2.0% | B | Present invention 7 |
| (1), (5) | A | 10.2 | 15.1 | 48.0% | C | Comparative Example 3 |
| (1), (5) | C | 10.2 | 14.4 | 40.8% | C | Comparative Example 4 |
| (1), (5) | C | 10.2 | 10.5 | 2.9% | B | Comparative Example 5 |
| (1), (5) | C | 10.2 | 10.3 | 1.0% | A | Comparative Example 6 |
| (1), (5) | C | 10.2 | 10.1 | 1.0% | A | Comparative Example 7 |
| (1), (5) | C | 10.2 | 9.9 | 2.9% | B | Comparative Example 8 |
| (1), (5) | C | 10.2 | 10.1 | 1.0% | A | Comparative Example 9 |
| (1), (5) | C | 10.2 | 10.5 | 2.9% | B | Comparative Example 10 |
| (1), (5) | C | 10.2 | 10.6 | 3.9% | B | Comparative Example 11 |

TABLE 3-continued

| | | | | | | |
|---|---|---|---|---|---|---|
| (1), (5) | C | 10.2 | 10.0 | 2.0% | B | Comparative Example 12 |
| (1), (5) | C | 10.2 | 9.8 | 3.9% | B | Comparative Example 13 |
| (1) | B | 10.2 | 17.1 | 67.6% | C | Comparative Example 14 |
| (1) | C | 10.2 | 16.5 | 61.8% | C | Comparative Example 15 |
| (1) | A | 10.2 | 10.4 | 2.0% | B | Present invention 8 |
| (1) | B | 10.2 | 10.2 | 0.0% | A | Present invention 9 |
| (1) | B | 10.2 | 10.4 | 2.0% | B | Present invention 10 |
| (1) | B | 10.2 | 10.1 | 1.0% | A | Present invention 11 |
| (1) | A | 10.2 | 9.9 | 2.9% | B | Present invention 12 |
| (1) | A | 10.2 | 10.2 | 0.0% | A | Present invention 13 |
| (1) | B | 10.2 | 10.3 | 1.0% | A | Present invention 14 |
| (1) | A | 10.2 | 16.1 | 57.8% | C | Comparative Example 16 |
| (1) | C | 10.2 | 15.0 | 47.1% | C | Comparative Example 17 |
| (1) | C | 10.2 | 10.6 | 3.9% | B | Comparative Example 18 |
| (1) | C | 10.2 | 10.7 | 4.9% | B | Comparative Example 19 |
| (1) | C | 10.2 | 10.5 | 2.9% | B | Comparative Example 20 |
| (1) | C | 10.2 | 10.4 | 2.0% | B | Comparative Example 21 |
| (1) | C | 10.2 | 10.3 | 1.0% | A | Comparative Example 22 |
| (1) | C | 10.2 | 10.1 | 1.0% | A | Comparative Example 23 |
| (1) | C | 10.2 | 10.2 | 0.0% | A | Comparative Example 24 |
| (1) | C | 10.2 | 10.4 | 2.0% | B | Comparative Example 25 |
| (1) | C | 10.2 | 10.3 | 1.0% | A | Comparative Example 26 |
| (5) | B | 10.2 | 18.2 | 78.4% | C | Comparative Example 27 |
| (5) | C | 10.2 | 17.3 | 69.6% | C | Comparative Example 28 |
| (5) | B | 10.2 | 10.1 | 1.0% | A | Present invention 15 |
| (5) | B | 10.2 | 10.3 | 1.0% | A | Present invention 16 |
| (5) | B | 10.2 | 10.0 | 2.0% | B | Present invention 17 |
| (5) | A | 10.2 | 10.0 | 2.0% | B | Present invention 18 |
| (5) | A | 10.2 | 10.0 | 2.0% | B | Present invention 19 |
| (5) | A | 10.2 | 10.2 | 0.0% | A | Present invention 20 |
| (5) | A | 10.2 | 10.2 | 0.0% | A | Present invention 21 |
| (5) | A | 10.2 | 10.0 | 2.0% | B | Present invention 22 |
| (5) | A | 10.2 | 9.9 | 2.9% | B | Present invention 23 |
| (5) | A | 10.2 | 9.8 | 3.9% | B | Resent invention 24 |
| (5) | B | 10.2 | 15.6 | 52.9% | C | Comparative Example 29 |
| (5) | C | 10.2 | 14.9 | 46.1% | C | Comparative Example 30 |
| (5) | C | 10.2 | 10.7 | 4.9% | B | Comparative Example 31 |
| (5) | C | 10.2 | 10.5 | 2.9% | B | Comparative Example 32 |
| (5) | C | 10.2 | 10.4 | 2.0% | B | Comparative Example 33 |
| (5) | C | 10.2 | 10.1 | 1.0% | A | Comparative Example 34 |

TABLE 3-continued

| | | | | | | |
|---|---|---|---|---|---|---|
| (5) | C | 10.2 | 9.8 | 3.9% | B | Comparative Example 35 |
| (5) | C | 10.2 | 10.1 | 1.0% | A | Comparative Example 36 |
| (5) | C | 10.2 | 10.3 | 1.0% | A | Comparative Example 37 |
| (5) | C | 10.2 | 10.5 | 2.9% | B | Comparative Example 38 |
| (5) | C | 10.2 | 10.6 | 3.9% | B | Comparative Example 39 |
| Comparative compound | B | 10.2 | 20.1 | 97.1% | C | Comparative Example 40 |
| Comparative compound | C | 10.2 | 19.9 | 95.1% | C | Comparative Example 41 |
| Comparative compound | C | 10.2 | 10.3 | 1.0% | A | Comparative Example 42 |
| Comparative compound | C | 10.2 | 10.5 | 2.9% | B | Comparative Example 43 |
| Comparative compound | C | 10.2 | 10.4 | 2.0% | B | Comparative Example 44 |
| Comparative compound | C | 10.2 | 10.6 | 3.9% | B | Comparative Example 45 |
| Comparative compound | C | 10.2 | 9.8 | 3.9% | B | Comparative Example 46 |
| Comparative compound | C | 10.2 | 9.9 | 2.9% | B | Comparative Example 47 |
| Comparative compound | C | 10.2 | 10.3 | 2.9% | B | Comparative Example 48 |
| Comparative compound | C | 10.2 | 15.4 | 51.0% | C | Comparative Example 49 |
| Comparative compound | C | 10.2 | 16.3 | 59.8% | C | Comparative Example 50 |
| Comparative compound | C | 10.2 | 10.4 | 2.0% | B | Comparative Example 51 |
| Comparative compound | C | 10.2 | 10.6 | 3.9% | B | Comparative Example 52 |
| Comparative compound | C | 10.2 | 10.1 | 1.0% | A | Comparative Example 53 |
| Comparative compound | C | 10.2 | 9.9 | 2.9% | B | Comparative Example 54 |
| Comparative compound | C | 10.2 | 10.4 | 2.0% | B | Comparative Example 55 |
| Comparative compound | C | 10.2 | 9.7 | 4.9% | B | Comparative Example 56 |
| Comparative compound | C | 10.2 | 10.7 | 4.9% | B | Comparative Example 57 |
| Comparative compound | C | 10.2 | 10.3 | 1.0% | A | Comparative Example 58 |
| Comparative compound | C | 10.2 | 10.1 | 1.0% | A | Comparative Example 59 |

From the results in Table 3, it has been found that a high precise measurement can be performed over the entire measurement range by using the high luminescent particles of the embodiment of the present invention and the unlabeled particles, and the effect of the present invention has been confirmed.

EXPLANATION OF REFERENCES

1 Sensor chip
2 Upper member
3 Intermediate member
4 Substrate
5 First container
6 Second container
7 Container group
8 Detection area
9 Reference area
10 Flow channel

What is claimed is:

1. A progesterone measuring kit, comprising:
   a first particle having a label and modified with a first binding substance capable of specifically binding to progesterone;
   a second particle having no label and modified with a second binding substance incapable of specifically binding to progesterone;
   a flow channel for flowing the first particle and the second particle; and
   a substrate having a substance capable of binding to the first binding substance,
   wherein the first particle having a label contains at least one compound represented by Formula (1) and a particle, and
   an average particle diameter of the first particles is 70 to 130 nm, and an average particle diameter of the second particles is 132 to 302 nm,

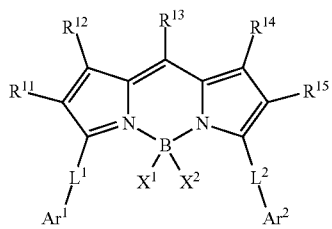

(1)

in the formula, both $R^{11}$ and $R^{15}$ represent an alkyl group or a phenyl group which may have an alkyl group; $R^{12}$ and $R^{14}$ represent an alkyl group; $R^{13}$ represents a phenyl group which may have a fluorine atom or $CF_3$; $X^1$ and $X^2$ represent a fluorine atom; $Ar^1$ and $Ar^2$ represent a phenyl group which may have an alkyl group; and $L^1$ and $L^2$ represent Formulae (L-1),

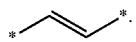

Formula (L-1)

2. The kit according to claim 1,
wherein the first particle and the second particle are latex particles.

3. The kit according to claim 1,
wherein the first particle having a label is a luminescent particle containing at least one kind of energy donor compound, at least one kind of energy acceptor compound, and a particle, and the at least one kind of the energy donor compound and the at least one kind of the energy acceptor compound is the compound represented by Formula (1).

4. The kit according to claim 3,
wherein a molar ratio of the energy donor compound to the energy acceptor compound is 1:10 to 10:1.

5. The kit according to claim 1,
wherein the first binding substance capable of specifically binding to progesterone is an antibody.

6. A progesterone measuring method comprising:
a step (i) of mixing a first particle (a) having a label and modified with a first binding substance capable of specifically binding to progesterone, a second particle (b) having no label and modified with a second binding substance incapable of specifically binding to progesterone, and a test sample (c) containing progesterone to obtain a mixture;
a step (Ii) of applying the mixture obtained in the step (i) onto a substrate;
a step (Iii) of capturing the first binding substance at a reaction site on the substrate having a substance capable of binding to the first binding substance; and
a step (iv) of detecting the first particle having a label and modified with the first binding substance captured on the reaction site,
wherein the first particle having a label contains at least one compound represented by Formula (1) and a particle,
an average particle diameter of the first particles is 70 to 130 nm, and an average particle diameter of the second particles is 132 to 302 nm,

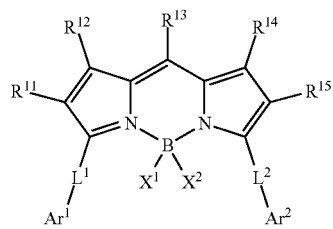

(1)

in the formula, both $R^{11}$ and $R^{15}$ represent an alkyl group or a phenyl group which may have an alkyl group; $R^{12}$ and $R^{14}$ represent an alkyl group; $R^{13}$ represents a phenyl group which may have a fluorine atom or $CF_3$; $X^1$ and $X^2$ represent a fluorine atom; $Ar^1$ and $Ar^2$ represent a phenyl group which may have an alkyl group; and $L^1$ and $L^2$ represent Formulae (L-1),

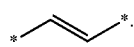

Formula (L-1)

7. The method according to claim 6,
wherein the first particle and the second particle are latex particles.

8. The method according to claim 6,
wherein the first particle having a label is a luminescent particle containing at least one kind of energy donor compound, at least one kind of energy acceptor compound, and a particle, and the at least one kind of the energy donor compound and the at least one kind of the energy acceptor compound is the compound represented by Formula (1).

9. The method according to claim 6,
wherein, in the step (iv), the first particle having a label and modified with the first binding substance captured on the reaction site is detected by a surface plasmon fluorescence method.

10. A progesterone measuring reagent comprising:
a first particle (a) having a label and modified with a first binding substance capable of specifically binding to progesterone; and
a second particle (b) having no label and modified with a second binding substance incapable of specifically binding to progesterone,
wherein the first particle having a label contains at least one compound represented by Formula (1) and a particle, and
an average particle diameter of the first particles is 70 to 130 nm, an average particle diameter of the second particles is 132 to 302 nm,

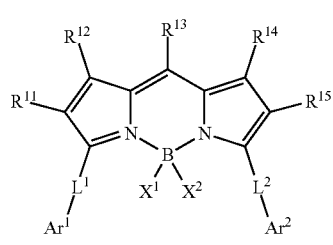

(1)

in the formula, both $R^{11}$ and $R^{15}$ represent an alkyl group or a phenyl group which may have an alkyl group; $R^{12}$ and $R^{14}$ represent an alkyl group; $R^{13}$ represents a phenyl group which may have a fluorine atom or $CF_3$; $X^1$ and $X^2$ represent a fluorine atom; $Ar^1$ and $Ar^2$ represent a phenyl group which may have an alkyl group; and $L^1$ and $L^2$ represent Formulae (L-1),

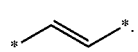

Formula (L-1)

11. The progesterone measuring reagent according to claim 10,
   wherein the first binding substance capable of specifically binding to the progesterone is an antibody.

12. The progesterone measuring reagent according to claim 10,
   wherein the first particle and the second particle are latex particles.

* * * * *